US008586046B2

(12) United States Patent
Baseman et al.

(10) Patent No.: US 8,586,046 B2
(45) Date of Patent: Nov. 19, 2013

(54) METHODS AND COMPOSITIONS FOR MYCOPLASMA PNEUMONIAE EXOTOXINS

(75) Inventors: Joel Barry Baseman, San Antonio, TX (US); Thirumalai Regasamy Kannan, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/339,866

(22) Filed: Dec. 29, 2011

(65) Prior Publication Data

US 2012/0276107 A1    Nov. 1, 2012

Related U.S. Application Data

(60) Continuation-in-part of application No. 12/612,173, filed on Nov. 4, 2009, now Pat. No. 8,088,894, which is a division of application No. 10/573,909, filed as application No. PCT/US2004/033037 on Oct. 1, 2004, now Pat. No. 7,622,571.

(60) Provisional application No. 60/508,607, filed on Oct. 3, 2003.

(51) Int. Cl.
*A61K 39/40* (2006.01)
*A61K 39/00* (2006.01)
*C07K 16/00* (2006.01)

(52) U.S. Cl.
USPC ............... 424/150.1; 424/139.1; 530/388.4; 530/387.9

(58) Field of Classification Search
None
See application file for complete search history.

(56) References Cited

U.S. PATENT DOCUMENTS

| | | |
|---|---|---|
| 5,534,413 A | 7/1996 | Lo et al. |
| 6,100,380 A | 8/2000 | Green et al. |
| 2003/0176331 A1 | 9/2003 | Rosenblum et al. |
| 2004/0191260 A1 | 9/2004 | Reiter et al. |
| 2006/0057155 A1 | 3/2006 | Masignani et al. |

FOREIGN PATENT DOCUMENTS

WO    WO 02/079242 A2    10/2002

OTHER PUBLICATIONS

Kabat et al. J. Exp. Med. 164: 642-654, 1986.*
Barile et al. "Experimentally induced septic arthritis in chimpanzees infected with *Mycoplasma hominis, Mycoplasma pneumoniae*, and *Ureaplasma urealyticum*" Clin Infect Dis. 18(5):694-703 (1994) (Abstract Only).
International Search Report for PCT/US05/12266; mailed Oct. 10, 2006.
Himmelreich et al. Accession No. P753409, Hypothetical protein MPN372 (Feb. 1, 1997).
Masignani et al. Accession No. AAE29374, *Mycoplasma pneumonia* ADP-ribosylating toxin protein (Jan. 27, 2003).
Sasaki et al. "The complete genomic sequence of *Mycoplasma penetrans*, an intracellular bacterial pathogen in humans" Nucleic Acids Research 30(23):5293-5300 (2002).
Dandekar et al. "Re-annotating the *Mycoplasma pneumoniae* genome sequence: adding value, function and reading frames" Nucleic Acids Research 28(17) 3278-3288 (2000).
Himmelreich et al. "Complete sequence analysis of the genome of the bacterium *Mycoplasma pneumoniae*" Nucleic Acids Research 24(22) 4420-4449 (1996).
Hott et al. "Skeletal muscle-specific immunotoxin for the treatment of focal muscle spasm" Neurology 50(2):485-491 (1998).
International Search Report and Written Opinion for PCT/US05/11897; Date of mailing Aug. 28, 2006.
International Search Report and Written Opinion for PCT/US04/33037; Date of mailing Oct. 11, 2005.
Kannan et al. "Identification and Characterization of Human Surfactant Protein A Binding Protein of *Mycoplasma pneumoniae*" Infection and Immunity 73(5):2828-2834, 2005.
Kannan et al. "ADP-ribosylating and vacuolating cytotoxin of *Mycoplasma pneumoniae* represents unique virulence determinant among bacterial pathogens" PNAS 103(17):6724-6729 (2006).
Pallen et al. "An abundance of bacterial ADP-ribosyltransferases—implications for the origin of oxotoxins and their human homologues" TRENDS in Microbiology 9(7):302-307 (2001).

* cited by examiner

*Primary Examiner* — S. Devi
(74) *Attorney, Agent, or Firm* — Myers Bigel Sibley & Sajovec, PA

(57) ABSTRACT

The present invention provides a *Mycoplasma pneumoniae* community acquired respiratory distress syndrome (CARDS) toxin, biologically active fragments/domains of the CARDS toxin, antibodies to the CARDS toxin and nucleic acids encoding the CARDS toxin. Also provided are methods of diagnosing, treating and/or preventing infection by *Mycoplasma pneumoniae* using the compositions provided herein.

5 Claims, 10 Drawing Sheets

A

B

| Antibody | Peptide/truncations of CARDS TX used for raising polyclonal antibody |
|---|---|
| 1 | 6-21 a.a. |
| 2 | 66-88 a.a. |
| 3 | 1-200 a.a. |
| 4 | 268-281 a.a. |
| 5 | 572-591 a.a. |
| 6 | rCARDS TX(1-591)a.a. |

FIGURE 5

| Immunoreactivity to TX truncations/peptides | Reactivity to D2 mAb | Reactivity to D3 mAb |
|---|---|---|
| rCARDS TX(1-200 a.a.) | - | - |
| rCARDS TX(1-249 a.a.) | - | - |
| rCARDS TX(1-268 a.a.) | + | - |
| rCARDS TX(1-307 a.a.) | + | - |
| rCARDS TX(1-359 a.a.) | + | - |
| rCARDS TX(345-591 a.a.) | - | + |
| rCARDS TX(264-438 a.a.) | - | + |
| rCARDS TX(439-591 a.a.) | - | - |
| 249-264 a.a. peptide | + | - |
| 420-438 a.a. peptide | - | + |

CARDS-FL 1 — 249 | 264 — 420 | 438 — 591

D2 mAb: aa 249-264
D3 mAb: aa 420-438

FIGURE 8

SEQUENCE LISTING

<160> NUMBER OF SEQ ID NOS: 160

<210> SEQ ID NO 1
<211> LENGTH: 591
<212> TYPE: PRT
<213> ORGANISM: Mycoplasma pneumoniae

<400> SEQUENCE: 1

Met Pro Asn Pro Val Arg Phe Val Tyr Arg Val Asp Leu Arg Ser Pro
1               5                   10                  15

Glu Glu Ile Phe Glu His Gly Phe Ser Thr Leu Gly Asp Val Arg Asn
            20                  25                  30

Phe Phe Glu His Ile Leu Ser Thr Asn Phe Gly Arg Ser Tyr Phe Ile
        35                  40                  45

Ser Thr Ser Glu Thr Pro Thr Ala Ala Ile Arg Phe Phe Gly Ser Trp
    50                  55                  60

Leu Arg Glu Tyr Val Pro Glu His Pro Arg Arg Ala Tyr Leu Tyr Glu
65                  70                  75                  80

Ile Arg Ala Asp Gln His Phe Tyr Asn Ala Arg Ala Thr Gly Glu Asn
                85                  90                  95

Leu Leu Asp Leu Met Arg Gln Arg Val Val Phe Asp Ser Gly Asp
            100                 105                 110

Arg Glu Met Ala Gln Met Gly Ile Arg Ala Leu Arg Thr Ser Phe Ala
        115                 120                 125

Tyr Gln Arg Glu Trp Phe Thr Asp Gly Pro Ile Ala Ala Asn Val
    130                 135                 140

Arg Ser Ala Trp Leu Val Asp Ala Val Pro Val Glu Pro Gly His Ala
145                 150                 155                 160

His His Pro Ala Gly Arg Val Val Glu Thr Thr Arg Ile Asn Glu Pro
                165                 170                 175

Glu Met His Asn Pro His Tyr Gln Glu Leu Gln Thr Gln Ala Asn Asp
            180                 185                 190

Gln Pro Trp Leu Pro Thr Pro Gly Ile Ala Thr Pro Val His Leu Ser
        195                 200                 205

Ile Pro Gln Ala Ala Ser Val Ala Asp Val Ser Glu Gly Thr Ser Ala

```
            210                 215                 220
Ser Leu Ser Phe Ala Cys Pro Asp Trp Ser Pro Ser Ser Asn Gly
225                 230                 235                 240

Glu Asn Pro Leu Asp Lys Cys Ile Ala Glu Lys Ile Asp Asn Tyr Asn
                    245                 250                 255

Leu Gln Ser Leu Pro Gln Tyr Ala Ser Ser Val Lys Glu Leu Glu Asp
                    260                 265                 270

Thr Pro Val Tyr Leu Arg Gly Ile Lys Thr Gln Lys Thr Phe Met Leu
                275                 280                 285

Gln Ala Asp Pro Gln Asn Asn Asn Val Phe Leu Val Glu Val Asn Pro
290                 295                 300

Lys Gln Lys Ser Ser Phe Pro Gln Thr Ile Phe Phe Trp Asp Val Tyr
305                 310                 315                 320

Gln Arg Ile Cys Leu Lys Asp Leu Thr Gly Ala Gln Ile Ser Leu Ser
                    325                 330                 335

Leu Thr Ala Phe Thr Thr Gln Tyr Ala Gly Gln Leu Lys Val His Leu
                340                 345                 350

Ser Val Ser Ala Val Asn Ala Val Asn Gln Lys Trp Lys Met Thr Pro
355                 360                 365

Gln Asp Ile Ala Ile Thr Gln Phe Arg Val Ser Ser Glu Leu Leu Gly
370                 375                 380

Gln Thr Glu Asn Gly Leu Phe Trp Asn Thr Lys Ser Gly Gly Ser Gln
385                 390                 395                 400

His Asp Leu Tyr Val Cys Pro Leu Lys Asn Pro Pro Ser Asp Leu Glu
                    405                 410                 415

Glu Leu Gln Ile Ile Val Asp Glu Cys Thr Thr His Ala Gln Phe Val
                420                 425                 430

Thr Met Arg Ala Ala Ser Thr Phe Phe Val Asp Val Gln Leu Gly Trp
                435                 440                 445

Tyr Trp Arg Gly Tyr Tyr Thr Pro Gln Leu Ser Gly Trp Ser Tyr
                450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Leu His Asn
                    485                 490                 495

Lys Leu Asn Lys Gln Thr Gly Tyr Ser Trp Asp Trp Val Glu Trp Leu
                500                 505                 510

Lys His Asp Met Asn Glu Asp Lys Asp Glu Asn Phe Lys Trp Tyr Phe
                515                 520                 525

Ser Arg Asp Asp Leu Thr Ile Pro Ser Val Glu Gly Leu Asn Phe Arg
530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                    565                 570                 575

Asn Val Glu Asp Lys Ile Leu Val Lys Asp Gly Phe Asp Arg Phe
                580                 585                 590

<210> SEQ ID NO 2
<211> LENGTH: 591
<212> TYPE: PRT
<213> ORGANISM: Mycoplasma pneumoniae

<400> SEQUENCE: 2

Met Pro Asn Pro Val Arg Phe Val Tyr Arg Val Asp Leu Arg Ser Pro
```

```
           1               5                  10                 15
Glu Glu Ile Phe Glu His Gly Phe Ser Thr Leu Gly Asp Val Arg Asn
                20                 25                 30

Phe Phe Glu His Ile Pro Ser Thr Asn Phe Gly Arg Ser Tyr Phe Ile
                35                 40                 45

Ser Thr Ser Glu Thr Pro Thr Ala Ala Ile Arg Phe Phe Gly Ser Trp
 50                 55                 60

Leu Arg Glu Tyr Val Pro Glu His Pro Arg Arg Ala Tyr Leu Tyr Glu
 65                 70                 75                 80

Ile Arg Ala Asp Gln His Phe Tyr Asn Ala Arg Ala Thr Gly Glu Asn
                85                 90                 95

Leu Leu Asp Leu Met Arg Gln Arg Gln Val Val Phe Asp Ser Gly Asp
                100                105                110

Arg Glu Met Ala Gln Met Gly Ile Arg Ala Leu Arg Thr Ser Phe Ala
                115                120                125

Tyr Gln Arg Glu Trp Phe Thr Asp Gly Pro Ile Ala Ala Ala Asn Val
                130                135                140

Arg Ser Ala Trp Leu Val Asp Ala Val Pro Val Glu Pro Gly His Ala
145                 150                155                160

His His Pro Ala Gly Arg Val Val Glu Thr Thr Arg Ile Asn Glu Pro
                165                170                175

Glu Met His Asn Pro His Tyr Gln Glu Leu Gln Thr Gln Ala Asn Asp
                180                185                190

Gln Pro Trp Leu Pro Thr Pro Gly Ile Ala Thr Pro Val His Leu Ser
                195                200                205

Ile Pro Gln Ala Ala Ser Val Ala Asp Val Ser Glu Gly Thr Ser Ala
                210                215                220

Ser Leu Ser Phe Ala Cys Pro Asp Trp Ser Pro Pro Ser Ser Asn Gly
225                 230                235                240

Glu Asn Pro Leu Asp Lys Cys Ile Ala Glu Lys Ile Asp Asn Tyr Asn
                245                250                255

Leu Gln Ser Leu Pro Gln Tyr Ala Ser Ser Val Lys Glu Leu Glu Asp
                260                265                270

Thr Pro Val Tyr Leu Arg Gly Ile Lys Thr Gln Lys Thr Phe Met Leu
                275                280                285

Gln Ala Asp Pro Gln Asn Asn Asn Val Phe Leu Val Glu Val Asn Pro
                290                295                300

Lys Gln Lys Ser Pro Phe Pro Gln Thr Ile Phe Phe Trp Asp Val Tyr
305                 310                315                320

Gln Arg Ile Cys Leu Lys Asp Leu Thr Gly Ala Gln Ile Ser Leu Ser
                325                330                335

Leu Thr Ala Phe Thr Thr Gln Tyr Ala Gly Gln Leu Lys Val His Leu
                340                345                350

Ser Val Ser Ala Val Asn Ala Val Asn Gln Lys Trp Lys Met Thr Pro
                355                360                365

Gln Asp Ser Ala Ile Thr Gln Phe Arg Val Ser Ser Glu Leu Leu Gly
                370                375                380

Gln Thr Glu Asn Gly Leu Ser Trp Asn Thr Lys Ser Gly Gly Ser Gln
385                 390                395                400

His Asp Leu Tyr Val Cys Pro Leu Lys Asn Pro Pro Ser Asp Leu Glu
                405                410                415

Glu Leu Gln Ile Ile Val Asp Glu Cys Thr Thr His Ala Gln Phe Val
                420                425                430
```

Thr Met Arg Ala Ala Ser Thr Phe Phe Val Asp Val Gln Leu Gly Trp
    435                 440                 445

Tyr Trp Arg Gly Tyr Tyr Thr Pro Gln Leu Ser Gly Trp Ser Tyr
    450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
                485                 490                 495

Lys Leu Asn Lys Gln Thr Gly Tyr Ser Trp Asp Trp Val Glu Trp Leu
                500                 505                 510

Lys His Asp Met Asn Glu Asp Lys Asp Glu Asn Phe Lys Trp Tyr Phe
                515                 520                 525

Ser Arg Asp Asp Leu Thr Ile Pro Ser Val Glu Gly Leu Asn Phe Arg
    530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                565                 570                 575

Asn Val Glu Asp Lys Ile Leu Val Lys Asp Gly Phe Asp Arg Phe
                580                 585                 590

<210> SEQ ID NO 3
<211> LENGTH: 591
<212> TYPE: PRT
<213> ORGANISM: Mycoplasma pneumoniae

<400> SEQUENCE: 3

Met Pro Asn Pro Val Arg Phe Val Tyr Arg Val Asp Leu Arg Ser Pro
1               5                   10                  15

Glu Glu Ile Phe Glu His Gly Phe Ser Thr Leu Gly Asp Val Arg Asn
                20                  25                  30

Phe Phe Glu His Ile Leu Ser Thr Asn Phe Gly Arg Ser Tyr Phe Ile
            35                  40                  45

Ser Thr Ser Glu Thr Pro Thr Ala Ala Ile Arg Phe Phe Gly Ser Trp
    50                  55                  60

Leu Arg Glu Tyr Val Pro Glu His Pro Arg Arg Ala Tyr Leu Tyr Glu
65              70                  75                  80

Ile Arg Ala Asp Gln His Phe Tyr Asn Ala Arg Ala Thr Gly Glu Asn
                85                  90                  95

Leu Leu Asp Leu Met Arg Gln Arg Gln Val Val Phe Asp Ser Gly Asp
                100                 105                 110

Arg Glu Met Ala Gln Met Gly Ile Arg Ala Leu Arg Thr Ser Phe Ala
            115                 120                 125

Tyr Gln Arg Glu Trp Phe Thr Asp Gly Pro Ile Ala Ala Ala Asn Val
    130                 135                 140

Arg Ser Ala Trp Leu Val Asp Ala Val Pro Val Glu Pro Gly His Ala
145                 150                 155                 160

His His Pro Ala Gly Arg Val Val Glu Thr Thr Arg Ile Asn Glu Pro
                165                 170                 175

Glu Met His Asn Pro His Tyr Gln Glu Leu Gln Thr Gln Ala Asn Asp
            180                 185                 190

Gln Pro Trp Leu Pro Thr Pro Gly Ile Ala Thr Pro Val His Leu Ser
    195                 200                 205

Ile Pro Gln Ala Ala Ser Val Ala Asp Val Ser Glu Gly Thr Ser Ala
    210                 215                 220

```
Ser Leu Ser Phe Ala Cys Pro Asp Trp Ser Pro Pro Ser Ser Asn Gly
225                 230                 235                 240

Glu Asn Pro Leu Asp Lys Cys Ile Ala Glu Lys Ile Asp Asn Tyr Asn
            245                 250                 255

Leu Gln Ser Leu Pro Gln Tyr Ala Ser Ser Val Lys Glu Leu Glu Asp
        260                 265                 270

Thr Pro Val Tyr Leu Arg Gly Ile Lys Thr Gln Lys Thr Phe Met Leu
    275                 280                 285

Gln Ala Asp Pro Gln Asn Asn Asn Val Phe Leu Val Glu Val Asn Pro
290                 295                 300

Lys Gln Lys Ser Ser Phe Pro Gln Thr Ile Phe Phe Trp Asp Val Tyr
305                 310                 315                 320

Gln Arg Ile Cys Leu Lys Asp Leu Thr Gly Ala Gln Ile Ser Leu Ser
            325                 330                 335

Leu Thr Ala Phe Thr Thr Gln Tyr Ala Gly Gln Leu Lys Val His Leu
        340                 345                 350

Ser Val Ser Ala Val Asn Ala Val Asn Gln Lys Trp Lys Met Thr Pro
    355                 360                 365

Gln Asp Ser Ala Ile Thr Gln Phe Arg Val Ser Ser Glu Leu Leu Gly
370                 375                 380

Gln Thr Glu Asn Gly Leu Phe Trp Asn Thr Lys Ser Gly Gly Ser Gln
385                 390                 395                 400

His Asp Leu Tyr Val Cys Pro Leu Lys Asn Pro Pro Ser Asp Leu Glu
            405                 410                 415

Glu Leu Gln Ile Ile Val Asp Glu Cys Thr Thr His Ala Gln Phe Val
        420                 425                 430

Thr Met Arg Ala Ala Ser Thr Phe Phe Val Asp Val Gln Leu Gly Trp
    435                 440                 445

Tyr Trp Arg Gly Tyr Tyr Tyr Thr Pro Gln Leu Ser Gly Trp Ser Tyr
450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
            485                 490                 495

Lys Leu Asn Lys Gln Thr Gly Tyr Ser Trp Asp Trp Val Glu Trp Leu
        500                 505                 510

Lys His Asp Met Asn Glu Asp Lys Asp Glu Asn Phe Lys Trp Tyr Phe
    515                 520                 525

Ser Arg Asp Asp Leu Thr Ile Pro Ser Val Glu Gly Leu Asn Phe Arg
530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
            565                 570                 575

Asn Val Glu Asp Lys Ile Leu Val Lys Asp Gly Phe Asp Arg Phe
        580                 585                 590

<210> SEQ ID NO 4
<211> LENGTH: 591
<212> TYPE: PRT
<213> ORGANISM: Mycoplasma pneumoniae

<400> SEQUENCE: 4

Met Pro Asn Pro Val Arg Phe Val Tyr Arg Val Asp Leu Arg Ser Pro
1               5                   10                  15
```

-continued

```
Glu Glu Ile Phe Glu His Gly Phe Ser Thr Leu Gly Asp Val Arg Asn
             20                  25                  30
Phe Phe Glu His Ile Leu Ser Thr Asn Phe Gly Arg Ser Tyr Phe Ile
             35                  40                  45
Ser Thr Ser Glu Thr Pro Thr Ala Ala Ile Arg Phe Phe Gly Ser Trp
 50                  55                  60
Leu Arg Glu Tyr Val Pro Glu His Pro Arg Arg Ala Tyr Leu Tyr Glu
 65                  70                  75                  80
Ile Arg Ala Asp Gln His Phe Tyr Asn Ala Arg Ala Thr Gly Glu Asn
                 85                  90                  95
Leu Leu Asp Leu Met Arg Gln Arg Gln Val Val Phe Ser Gly Asp
             100                 105                 110
Arg Glu Met Ala Gln Met Gly Ile Arg Ala Leu Arg Thr Ser Phe Ala
             115                 120                 125
Tyr Gln Arg Glu Trp Phe Thr Asp Gly Pro Ile Ala Ala Ala Asn Val
             130                 135                 140
Arg Ser Ala Trp Leu Val Asp Ala Val Pro Val Glu Pro Gly His Ala
145                 150                 155                 160
His His Pro Ala Gly Arg Val Val Glu Thr Thr Arg Ile Asn Glu Pro
                 165                 170                 175
Glu Met His Asn Pro His Tyr Gln Glu Leu Gln Thr Gln Ala Asn Asp
             180                 185                 190
Gln Pro Trp Leu Pro Thr Pro Gly Ile Ala Thr Pro Val His Leu Ser
             195                 200                 205
Ile Pro Gln Ala Ala Ser Val Ala Asp Val Ser Glu Gly Thr Ser Ala
 210                 215                 220
Ser Leu Ser Phe Ala Cys Pro Asp Trp Ser Pro Pro Ser Ser Asn Gly
225                 230                 235                 240
Glu Asn Pro Leu Asp Lys Cys Ile Ala Glu Lys Ile Asp Asn Tyr Asn
                 245                 250                 255
Leu Gln Ser Leu Pro Gln Tyr Ala Ser Ser Val Lys Glu Leu Glu Asp
             260                 265                 270
Thr Pro Val Tyr Leu Arg Gly Ile Lys Thr Gln Lys Thr Phe Met Leu
             275                 280                 285
Gln Ala Asp Pro Gln Asn Asn Asn Val Phe Leu Val Glu Val Asn Pro
 290                 295                 300
Lys Gln Lys Ser Ser Phe Pro Gln Thr Ile Phe Phe Trp Asp Val Tyr
305                 310                 315                 320
Gln Arg Ile Cys Leu Lys Asp Leu Thr Gly Ala Gln Ile Ser Leu Ser
                 325                 330                 335
Leu Thr Ala Phe Thr Thr Gln Tyr Ala Gly Gln Leu Lys Val His Leu
             340                 345                 350
Ser Val Ser Ala Val Asn Ala Val Asn Gln Lys Trp Lys Met Thr Pro
             355                 360                 365
Gln Asp Ser Ala Ile Thr Gln Phe Arg Val Ser Ser Glu Leu Leu Gly
 370                 375                 380
Gln Thr Glu Asn Gly Leu Phe Arg Asn Thr Lys Ser Gly Gly Ser Gln
385                 390                 395                 400
His Asp Leu Tyr Val Cys Pro Leu Lys Asn Pro Pro Ser Asp Leu Glu
                 405                 410                 415
Glu Leu Gln Ile Ile Val Asp Glu Cys Thr Thr His Ala Gln Phe Val
             420                 425                 430
Thr Met Arg Ala Ala Ser Thr Phe Phe Val Asp Val Gln Leu Gly Trp
             435                 440                 445
```

```
Tyr Trp Arg Gly Tyr Tyr Thr Pro Gln Leu Ser Gly Trp Ser Tyr
    450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
                485                 490                 495

Lys Leu Asn Lys Gln Thr Gly Tyr Ser Trp Asp Trp Val Glu Trp Leu
            500                 505                 510

Lys His Asp Met Asn Glu Asp Lys Asp Glu Asn Phe Lys Trp Tyr Phe
            515                 520                 525

Ser Arg Asp Asp Leu Thr Ile Pro Ser Val Glu Gly Leu Asn Phe Arg
            530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                565                 570                 575

Asn Val Glu Asp Lys Ile Leu Val Lys Asp Gly Phe Asp Arg Phe
            580                 585                 590

<210> SEQ ID NO 5
<211> LENGTH: 591
<212> TYPE: PRT
<213> ORGANISM: Mycoplasma pneumoniae

<400> SEQUENCE: 5

Met Pro Asn Pro Val Arg Phe Val Tyr Arg Val Asp Leu Arg Ser Pro
1               5                   10                  15

Glu Glu Ile Phe Glu His Gly Phe Ser Thr Leu Gly Asp Val Arg Asn
            20                  25                  30

Phe Phe Glu His Ile Leu Ser Thr Asn Phe Gly Arg Ser Tyr Phe Ile
        35                  40                  45

Ser Thr Ser Glu Thr Pro Thr Ala Ala Ile Arg Phe Phe Gly Ser Trp
    50                  55                  60

Leu Arg Glu Tyr Val Pro Glu His Pro Arg Arg Ala Tyr Leu Tyr Glu
65                  70                  75                  80

Ile Arg Ala Asp Gln His Phe Tyr Asn Ala Arg Ala Thr Gly Glu Asn
                85                  90                  95

Leu Leu Asp Leu Met Arg Gln Arg Gln Val Val Phe Asp Ser Gly Asp
            100                 105                 110

Arg Glu Met Ala Gln Met Gly Ile Arg Ala Leu Arg Thr Ser Phe Ala
        115                 120                 125

Tyr Gln Arg Glu Trp Phe Thr Asp Gly Pro Ile Ala Ala Ala Asn Val
    130                 135                 140

Arg Ser Ala Trp Leu Val Asp Ala Val Pro Val Glu Pro Gly His Ala
145                 150                 155                 160

His His Pro Ala Gly Arg Val Val Glu Thr Thr Arg Ile Asn Glu Pro
                165                 170                 175

Glu Met His Asn Pro His Tyr Gln Glu Leu Gly Thr Gln Ala Asn Asp
            180                 185                 190

Gln Pro Trp Leu Pro Thr Pro Gly Ile Ala Thr Pro Val His Leu Ser
        195                 200                 205

Ile Pro Gln Ala Ala Ser Val Ala Asp Val Ser Glu Gly Thr Ser Ala
    210                 215                 220

Ser Leu Ser Phe Ala Cys Pro Asp Trp Ser Pro Pro Ser Ser Asn Gly
225                 230                 235                 240
```

Glu Asn Pro Leu Gly Lys Cys Ile Ala Glu Lys Ile Asp Asn Tyr Asn
            245                 250                 255

Leu Gln Ser Leu Pro Gln Tyr Ala Ser Ser Val Lys Glu Leu Glu Asp
        260                 265                 270

Thr Pro Val Tyr Leu Arg Gly Ile Lys Thr Gln Lys Thr Phe Met Leu
            275                 280                 285

Gln Ala Asp Pro Gln Asn Asn Asn Val Phe Leu Val Glu Val Asn Pro
290                 295                 300

Lys Gln Lys Ser Ser Phe Pro Gln Thr Ile Phe Phe Trp Asp Val Tyr
305                 310                 315                 320

Gln Arg Ile Cys Leu Lys Asp Leu Thr Gly Ala Gln Ile Ser Leu Ser
                325                 330                 335

Leu Thr Ala Phe Thr Thr Gln Tyr Ala Gly Gln Leu Lys Val His Leu
            340                 345                 350

Ser Val Ser Ala Val Asn Ala Val Asn Gln Lys Trp Lys Met Thr Pro
        355                 360                 365

Gln Asp Ser Ala Ile Thr Gln Phe Arg Val Ser Ser Glu Leu Leu Gly
370                 375                 380

Gln Thr Glu Asn Gly Leu Phe Trp Asn Thr Lys Ser Gly Gly Ser Gln
385                 390                 395                 400

His Asp Leu Tyr Val Cys Pro Leu Lys Asn Pro Pro Ser Asp Leu Glu
                405                 410                 415

Glu Leu Gln Ile Ile Val Asp Glu Cys Thr Thr His Ala Gln Phe Val
            420                 425                 430

Thr Met Arg Ala Ala Ser Thr Phe Phe Val Asp Val Gln Leu Gly Trp
        435                 440                 445

Tyr Trp Arg Gly Tyr Tyr Tyr Thr Pro Gln Leu Ser Gly Trp Ser Tyr
        450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
                485                 490                 495

Lys Leu Asn Lys Gln Thr Gly Tyr Ser Trp Asp Trp Val Glu Trp Leu
            500                 505                 510

Lys His Asp Met Asn Glu Asp Lys Asp Glu Asn Phe Lys Trp Tyr Phe
        515                 520                 525

Ser Arg Asp Asp Leu Thr Ile Pro Ser Val Glu Gly Leu Asn Phe Arg
530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                565                 570                 575

Asn Val Glu Asp Lys Ile Leu Lys Asp Gly Phe Asp Arg Phe
            580                 585                 590

<210> SEQ ID NO 6
<211> LENGTH: 591
<212> TYPE: PRT
<213> ORGANISM: Artificial
<220> FEATURE:
<223> OTHER INFORMATION: Composite amino acid sequence

<400> SEQUENCE: 6

Met Pro Asn Pro Val Arg Phe Val Tyr Arg Val Asp Leu Arg Ser Pro
1               5                   10                  15

```
Glu Glu Ile Phe Glu His Gly Phe Ser Thr Leu Gly Asp Val Arg Asn
                20              25                  30
Phe Phe Glu His Ile Pro Ser Thr Asn Phe Gly Arg Ser Tyr Phe Ile
            35              40                  45
Ser Thr Ser Glu Thr Pro Thr Ala Ala Ile Arg Phe Phe Gly Ser Trp
50              55                  60
Leu Arg Glu Tyr Val Pro Glu His Pro Arg Arg Ala Tyr Leu Tyr Glu
65              70                  75                          80
Ile Arg Ala Asp Gln His Phe Tyr Asn Ala Arg Ala Thr Gly Glu Asn
                85                  90                  95
Leu Leu Asp Leu Met Arg Gln Arg Gln Val Val Phe Ser Gly Asp
                100                 105                 110
Arg Glu Met Ala Gln Met Gly Ile Arg Ala Leu Arg Thr Ser Phe Ala
                115                 120                 125
Tyr Gln Arg Glu Trp Phe Thr Asp Gly Pro Ile Ala Ala Ala Asn Val
        130                 135                 140
Arg Ser Ala Trp Leu Val Asp Ala Val Pro Val Glu Pro Gly His Ala
145                 150                 155                 160
His His Pro Ala Gly Arg Val Val Glu Thr Thr Arg Ile Asn Glu Pro
                165                 170                 175
Glu Met His Asn Pro His Tyr Gln Glu Leu Gln Thr Gln Ala Asn Asp
                180                 185                 190
Gln Pro Trp Leu Pro Thr Pro Gly Ile Ala Thr Pro Val His Leu Ser
        195                 200                 205
Ile Pro Gln Ala Ala Ser Val Ala Asp Val Ser Glu Gly Thr Ser Ala
        210                 215                 220
Ser Leu Ser Phe Ala Cys Pro Asp Trp Ser Pro Pro Ser Ser Asn Gly
225                 230                 235                 240
Glu Asn Pro Leu Gly Lys Cys Ile Ala Glu Lys Ile Asp Asn Tyr Asn
                245                 250                 255
Leu Gln Ser Leu Pro Gln Tyr Ala Ser Ser Val Lys Glu Leu Glu Asp
                260                 265                 270
Thr Pro Val Tyr Leu Arg Gly Ile Lys Thr Gln Lys Thr Phe Met Leu
        275                 280                 285
Gln Ala Asp Pro Gln Asn Asn Asn Val Phe Leu Val Glu Val Asn Pro
290                 295                 300
Lys Gln Lys Pro Ser Phe Pro Gln Thr Ile Phe Phe Trp Asp Val Tyr
305                 310                 315                 320
Gln Arg Ile Cys Leu Lys Asp Leu Thr Gly Ala Gln Ile Ser Leu Ser
                325                 330                 335
Leu Thr Ala Phe Thr Thr Gln Tyr Ala Gly Gln Leu Lys Val His Leu
                340                 345                 350
Ser Val Ser Ala Val Asn Ala Val Asn Gln Lys Trp Lys Met Thr Pro
                355                 360                 365
Gln Asp Ser Ala Ile Thr Gln Phe Arg Val Ser Ser Glu Leu Leu Gly
                370                 375                 380
Gln Thr Glu Asn Gly Leu Ser Arg Asn Thr Lys Ser Gly Gly Ser Gln
385                 390                 395                 400
His Asp Leu Tyr Val Cys Pro Leu Lys Asn Pro Pro Ser Asp Leu Glu
                405                 410                 415
Glu Leu Gln Ile Ile Val Asp Glu Cys Thr Thr His Ala Gln Phe Val
                420                 425                 430
Thr Met Arg Ala Ala Ser Thr Phe Phe Val Asp Val Gln Leu Gly Trp
                435                 440                 445
```

Tyr Trp Arg Gly Tyr Tyr Tyr Thr Pro Gln Leu Ser Gly Trp Ser Tyr
    450                 455                 460

Gln Met Lys Thr Pro Asp Gly Gln Ile Phe Tyr Asp Leu Lys Thr Ser
465                 470                 475                 480

Lys Ile Phe Phe Val Gln Asp Asn Gln Asn Val Phe Phe Leu His Asn
                485                 490                 495

Lys Leu Asn Lys Gln Thr Gly Tyr Ser Trp Asp Trp Val Glu Trp Leu
            500                 505                 510

Lys His Asp Met Asn Glu Asp Lys Asp Glu Asn Phe Lys Trp Tyr Phe
            515                 520                 525

Ser Arg Asp Asp Leu Thr Ile Pro Ser Val Glu Gly Leu Asn Phe Arg
            530                 535                 540

His Ile Arg Cys Tyr Ala Asp Asn Gln Gln Leu Lys Val Ile Ile Ser
545                 550                 555                 560

Gly Ser Arg Trp Gly Gly Trp Tyr Ser Thr Tyr Asp Lys Val Glu Ser
                565                 570                 575

Asn Val Glu Asp Lys Ile Leu Val Lys Asp Gly Phe Asp Arg Phe
            580                 585                 590

<210> SEQ ID NO 7
<211> LENGTH: 1860
<212> TYPE: DNA
<213> ORGANISM: Mycoplasma pneumoniae

<400> SEQUENCE: 7
tttttaattt gtaaaatttc attttttaaa aatgccaaat cctgttagat ttgtttaccg      60
tgttgatttg agaagccctg aagaaatttt tgaacatggc ttttcaactt taggtgatgt     120
gagaaatttc tttgaacaca ttctctccac taattttggt agaagctatt ttatttccac     180
ttcagaaaca cccacagcag ctattcgctt ctttggtagc tggttacggg aatatgtacc     240
agagcacccc agaagggctt acttatatga aattcgtgcc gaccaacact tttacaatgc     300
ccgcgccact ggggagaact tgttagattt aatgcgtcaa agacaagtag tatttgactc     360
tggtgatcga gaaatggcac aaatgggaat tagagcttta cgcacttcct ttgcgtatca     420
acgtgaatgg tttaccgatg gtccaattgc agcagctaat gtccgtagtg cttgactagt     480
agatgctgtt cccgttgaac ctggtcatgc tcaccacccg gctggtcgtg ttgtagagac     540
tactagaatt aatgaaccgg aaatgcacaa ccctcattat caagagctgc aaacccaagc     600
caatgatcaa ccatgattgc caacaccagg aatagctact cctgtacatt tatcaattcc     660
ccaagcagct tccgttgctg atgtttcgga aggtacttcc gcttcgctat cgtttgcgtg     720
ccctgattga agtccacctt ctagtaatgg tgaaaatccg ctagacaaat gcattgcgga     780
aaagattgat aactataacc tacaatcctt accacagtac gctagcagtg taaaggaact     840
ggaagataca ccagtatacc taaggggaat taaaacgcaa aaaaccttta tgttacaagc     900
agatccgcaa aataacaatg tcttttttggt cgaagtaaac cccaaacaaa gtccagctt     960 tccccaaacc atcttctttt gggatgttta tcaacgaatt tgtctcaagg atttaactgg    1020
tgcacaaatc agtctttcgc ttactgcctt tactactcag tatgctggtc agctcaaagt    1080
gcaccttagt gttagcgcgg ttaatgccgt gaaccaaaag tgaaaaatga caccgcaaga    1140
cattgcaata actcagtttc gggtctcctc tgaactgtta ggtcaaactg aaaatggctt    1200
gttctgaaat accaagagtg gtggttcaca cacgatttg tatgtatgtc ctttgaaaaa    1260
tccacctagt gatttggaag aattacaaat aattgttgat gaatgtacta cccatgcgca    1320

```
gtttgttact atgcgtgcag ctagcacctt ctttgttgat gttcagctag gctggtattg    1380
aaggggttat tactataccc cacaattaag tggttgatct tatcagatga aaacaccaga    1440
tggacagata ttctatgatc taaaaacttc gaaaatcttc tttgtccagg acaaccaaaa    1500
cgtgttcttt ctccataata aactcaacaa acaaactggt tacagctggg attgagtaga    1560
atggctaaaa catgacatga atgaggacaa agacgaaaac tttaaatggt acttttcgcg    1620
tgatgacctt accattcctt ccgttgaagg gcttaacttc cgccacattc gctgttacgc    1680
tgacaaccag cagttaaagg tgatcataag cggttcacgt tggggcggtt ggtactccac    1740
ttacgataaa gttgaaagta atgtcgaaga taagattttg gtcaaagatg gttttgatcg    1800
cttttagcga ttaagcttta acgtcactgt tttgctctaa tgttagaagc aaagatcttg    1860

<210> SEQ ID NO 8
<211> LENGTH: 1773
<212> TYPE: DNA
<213> ORGANISM: Artificial
<220> FEATURE:
<223> OTHER INFORMATION: S1 nucleotide sequence with tga codons changed
      to tgg for expression in E. coli

<400> SEQUENCE: 8
atgccaaatc ctgttagatt tgtttaccgt gttgatttga gaagccctga agaaattttt      60
gaacatggct tttcaacttt aggtgatgtg agaaatttct ttgaacacat tccctccact     120
aattttggta gaagctattt tatttccact tcagaaacac ccacagcagc tattcgcttc     180
tttggtagct ggttacggga atatgtacca gagcacccca gaagggctta cttatatgaa     240
attcgtgccg accaacactt ttacaatgcc cgcgccactg gggagaactt gttagattta     300
atgcgtcaaa gacaagtagt atttgactct ggtgatcgag aaatggcaca atgggaatt      360 agagctttac gcacttcctt tgcgtatcaa cgtgaatggt ttaccgatgg tccaattgca     420
gcagctaatg tccgtagtgc ttggctagta gatgctgttc ccgttgaacc tggtcatgct     480
caccacccgg ctggtcgtgt tgtagagact actagaatta atgaaccgga atgcacaac      540 cctcattatc aagagctgca aacccaagcc aatgatcaac catggttgcc aacaccagga     600
atagctactc ctgtacattt atcaattccc caagcagctt ccgttgctga tgtttcggaa     660
ggtacttccg cttcgctatc gtttgcgtgc cctgattgga gtccaccttc tagtaatggt     720
gaaaatccgc tagacaaatg cattgcggaa aagattgata actataacct acaatcctta     780
ccacagtacg ctagcagtgt aaaggaactg gaagatacac cagtataccct aaggggaatt     840 aaaacgcaaa aaacctttat gttacaagca gatccgcaaa ataacaatgt ctttttggtc     900
gaagtaaacc ccaaacaaaa gcccagcttt ccccaaacca tcttctttg ggatgtttat     960 caacgaattt gtctcaagga tttaactggt gcacaaatca gtctttcgct tactgccttt    1020
actactcagt atgctggtca gctcaaagtg caccttagtg ttagcgcggt taatgccgtg    1080
aaccaaaagt ggaaaatgac accgcaagac agtgcaataa ctcagtttcg ggtctcctct    1140
gaactgttag gtcaaactga aaatggcttg tcctggaata ccaagagtgg tggttcacaa    1200
cacgatttgt atgtatgtcc tttgaaaaat ccacctagtg atttggaaga attacaaata    1260
attgttgatg aatgtactac ccatgcgcag tttgttacta tgcgtgcagc tagcaccttc    1320
tttgttgatg ttcagctagg ctggtattgg aggggtttat tactataccc cacaattaagt    1380 ggttggtctt atcagatgaa aacaccagat ggacagatat tctatgatct aaaaacttcg    1440
aaaatcttct ttgtccagga caaccaaaac gtgttctttc tccataataa actcaacaaa    1500
caaactggtt acagctggga ttgggtagaa tggctaaaac atgacatgaa tgaggacaaa    1560
```

```
gacgaaaact ttaaatggta cttttcgcgt gatgacctta ccattccttc cgttgaaggg      1620
cttaacttcc gccacattcg ctgttacgct gacaaccagc agttaaaggt gatcataagc      1680
ggttcacgtt ggggcggttg gtactccact tacgataaag ttgaaagtaa tgtcgaagat      1740
aagattttgg tcaaagatgg ttttgatcgc ttt                                  1773
```

<210> SEQ ID NO 9
<211> LENGTH: 1773
<212> TYPE: DNA
<213> ORGANISM: Artificial
<220> FEATURE:
<223> OTHER INFORMATION: L2 nucleotide sequence with tga codons changed
      to tgg for expression in E. Coli

<400> SEQUENCE: 9

```
atgccaaatc ctgttagatt tgtttaccgt gttgatttga aagccctga agaaattttt      60 gaacatggct tttcaacttt aggtgatgtg agaaatttct tgaacacat tctctccact      120 aattttggta aagctatttt tatttccact tcagaaacac ccacagcagc tattcgcttc      180
tttggtagct ggtacgggaa atatgtacca gagcacccca aagggcttaa cttatatgaa      240
attcgtgccg accaacactt ttacaatgcc cgcgccactg gggagaactt gttagattta      300
atgcgtcaaa acaagtagt atttgactct ggtgatcgag aaatggcaca atgggaatt       360 agagctttac gcacttcctt tgcgtatcaa cgtgaatggt ttaccgatgg tccaattgca      420
gcagctaatg tccgtagtgc ttggctagta gatgctgttc ccgttgaacc tggtcatgct      480
caccacccgg ctggtcgtgt tgtagagact actagaatta atgaaccgga aatgcacaac      540
cctcattatc aagagctgca aacccaagcc aatgatcaac catggttgcc aacaccagga      600
atagctactc ctgtacattt atcaattccc caagcagctt ccgttgctga tgtttcggaa      660
ggtacttccg cttcgctatc gtttgcgtgc cctgattgga gtccaccttc tagtaatggt      720
gaaaatccgc taggcaaatg cattgcggaa aagattgata actataacct acaatcctta      780
ccacagtacg ctagcagtgt aaaggaactg gaagatacac cagtatacct aagggggaatt      840 aaaacgcaaa aaacctttat gttacaagca gatccgcaaa ataacaatgt ctttttggtc      900
gaagtaaacc ccaaacaaaa gtccagcttt ccccaaacca tcttcttttg ggatgtttat      960
caacgaattt gtctcaagga tttaactggt gcacaaatca gtctttcgct tactgccttt      1020
actactcagt atgctggtca gctcaaagtg caccttagtg ttagcgcggt taatgccgtg      1080
aaccaaaagt ggaaaatgac accgcaagac agtgcaataa ctcagtttcg ggtctcctct      1140
gaactgttag gtcaaactga aaatggcttg ttctggaata ccaagagtgg tggttcacaa      1200
cacgatttgt atgtatgtcc tttgaaaaat ccacctagtg atttggaaga attacaaata      1260
attgttgatg aatgtactac ccatgcgcag tttgttacta tgcgtgcagc tagcaccttc      1320
tttgttgatg ttcagctagg ctggtattgg aggggttatt actataccc acaattaagt      1380 ggttggtctt atcagatgaa aacaccagat ggacagatat tctatgatct aaaaacttcg      1440
aaaatcttct ttgtccagga caaccaaaac gtgttctttc tccataataa actcaacaaa      1500
caaactggtt acagctggga ttgggtagaa tggctaaaac atgacatgaa tgaggacaaa      1560
gacgaaaact ttaaatggta cttttcgcgt gatgacctta ccattccttc cgttgaaggg      1620
cttaacttcc gccacattcg ctgttacgct gacaaccagc agttaaaggt gatcataagc      1680
ggttcacgtt ggggcggttg gtactccact tacgataaag ttgaaagtaa tgtcgaagat      1740
aagattttgg tcaaagatgg ttttgatcgc ttt                                  1773
```

<210> SEQ ID NO 10
<211> LENGTH: 1773
<212> TYPE: DNA
<213> ORGANISM: Artificial
<220> FEATURE:
<223> OTHER INFORMATION: JL nucleotide sequence with tga codons changed to tgg for expression in E. coli

<400> SEQUENCE: 10

```
atgccaaatc ctgttagatt tgtttaccgt gttgatttga aagccctga agaaattttt      60
gaacatggct tttcaacttt aggtgatgtg agaaatttct ttgaacacat tctctccact     120
aattttggta aagctatttt tatttccact tcagaaacac ccacagcagc tattcgcttc     180
tttggtagct ggttacggga atatgtacca gagcacccca aagggctta cttatatgaa     240
attcgtgccg accaacactt ttacaatgcc cgcgccactg gggagaactt gttagattta     300
atgcgtcaaa gacaagtagt atttgactct ggtgatcgag aaatggcaca aatgggaatt     360
agagctttac gcacttcctt tgcgtatcaa cgtgaatggt ttaccgatgg tccaattgca     420
gcagctaatg tccgtagtgc ttggctagta gatgctgttc ccgttgaacc tggtcatgct     480
caccacccgg ctggtcgtgt tgtagagact actagaatta atgaaccgga atgcacaac     540
cctcattatc aagagctgca aacccaagcc aatgatcaac catggttgcc aacaccagga     600
atagctactc ctgtacattt atcaattccc caagcagctt ccgttgctga tgtttcggaa     660
ggtacttccg cttcgctatc gtttgcgtgc cctgattgga gtccaccttc tagtaatggt     720
gaaaatccgc tagacaaatg cattgcggaa aagattgata actataacct acaatcctta     780
ccacagtacg ctagcagtgt aaaggaactg gaagatacac cagtatacct aagggggaatt     840
aaaacgcaaa aaacctttat gttacaagca gatccgcaaa ataacaatgt ctttttggtc     900
gaagtaaacc ccaaacaaaa gtccagcttt ccccaaacca tcttcttttg ggatgtttat     960
caacgaattt gtctcaagga tttaactggt gcacaaatca gtctttcgct tactgccttt    1020
actactcagt atgctggtca gctcaaagtg caccttagtg ttagcgcggt taatgccgtg    1080
aaccaaaagt ggaaaatgac accgcaagac agtgcaataa ctcagtttcg ggtctcctct    1140
gaactgttag gtcaaactga aaatggcttg ttctggaata ccaagagtgg tggttcacaa    1200
cacgatttgt atgtatgtcc tttgaaaaat ccacctagtg atttggaaga attacaaata    1260
attgttgatg aatgtactac ccatgcgcag tttgttacta tgcgtgcagc tagcaccttc    1320
tttgttgatg ttcagctagg ctggtattgg aggggttatt actataccc acaattaagt    1380
ggttggtctt atcagatgaa aacaccagat ggacagatat tctatgatct aaaaacttcg    1440
aaaatcttct ttgtccagga caaccaaaac gtgttctttc tccataataa actcaacaaa    1500
caaactggtt acagctggga ttgggtagaa tggctaaaac atgacatgaa tgaggacaaa    1560
gacgaaaact ttaaatggta ctttcgcgt gatgacctta ccattccttc cgttgaaggg    1620
cttaacttcc gccacattcg ctgttacgct gacaaccagc agttaaaggt gatcataagc    1680
ggttcacgtt ggggcggttg gtactccact tacgataaag ttgaaagtaa tgtcgaagat    1740
aagatttttgg tcaaagatgg ttttgatcgc ttt                                1773
```

<210> SEQ ID NO 11
<211> LENGTH: 1773
<212> TYPE: DNA
<213> ORGANISM: Artificial
<220> FEATURE:
<223> OTHER INFORMATION: RJL1 nucleotide sequence with tga codons changed to tgg for expression in E. coli

<400> SEQUENCE: 11

```
atgccaaatc ctgttagatt tgtttaccgt gttgatttga gaagccctga agaaatttt     60
gaacatggct tttcaacttt aggtgatgtg agaaatttct ttgaacacat tctctccact    120
aattttggta gaagctattt tatttccact tcagaaacac ccacagcagc tattcgcttc    180
tttggtagct ggttacggga atatgtacca gagcacccca gaagggctta cttatatgaa    240
attcgtgccg accaacactt ttacaatgcc cgcgccactg gggagaactt gttagattta    300
atgcgtcaaa gacaagtagt atttgactct ggtgatcgag aaatggcaca aatgggaatt    360
agagctttac gcacttcctt tgcgtatcaa cgtgaatggt ttaccgatgg tccaattgca    420
gcagctaatg tccgtagtgc ttggctagta gatgctgttc ccgttgaacc tggtcatgct    480
caccacccgg ctggtcgtgt tgtagagact actagaatta atgaaccgga atgcacaac    540
cctcattatc aagagctgca aacccaagcc aatgatcaac catggttgcc aacaccagga    600
atagctactc ctgtacattt atcaattccc caagcagctt ccgttgctga tgtttcggaa    660
ggtacttccg cttcgctatc gtttgcgtgc cctgattgga gtccaccttc tagtaatggt    720
gaaaatccgc tagacaaatg cattgcggaa aagattgata actataacct acaatccta    780
ccacagtacg ctagcagtgt aaaggaactg gaagatacac cagtatacct aagggggaatt   840
aaaacgcaaa aaacctttat gttacaagca gatccgcaaa ataacaatgt cttttggtc     900
gaagtaaacc ccaaacaaaa gtccagcttt ccccaaacca tcttcttttg ggatgtttat    960
caacgaattt gtctcaagga tttaactggt gcacaaatca gtctttcgct tactgccttt   1020
actactcagt atgctggtca gctcaaagtg caccttagtg ttagcgcggt taatgccgtg   1080
aaccaaaagt ggaaaatgac accgcaagac agtgcaataa ctcagtttcg ggtctcctct   1140
gaactgttag gtcaaactga aaatggcttg ttccggaata ccaagagtgg tggttcacaa   1200
cacgatttgt atgtatgtcc tttgaaaaat ccacctagtg atttggaaga attacaaata   1260
attgttgatg aatgtactac ccatgcgcag tttgttacta tgcgtgcagc tagcaccttc   1320
tttgttgatg ttcagctagg ctggtattgg aggggttatt actataccc acaattaagt   1380
ggttggtctt atcagatgaa acaccagat ggacagatat tctatgatct aaaaacttcg   1440
aaaatcttct tgtccagga caaccaaaac gtgttctttc tccataataa actcaacaaa   1500
caaactggtt acagctggga ttgggtagaa tggctaaaac atgacatgaa tgaggacaaa   1560
gacgaaaact ttaaatggta cttttcgcgt gatgaccta ccattccttc cgttgaaggg    1620
cttaacttcc gccacattcg ctgttacgct gacaaccagc agttaaaggt gatcataagc   1680
ggttcacgtt ggggcggttg gtactccact tacgataaag ttgaaagtaa tgtcgaagat   1740
aagattttgg tcaaagatgg ttttgatcgc ttt                                1773
```

<210> SEQ ID NO 12
<211> LENGTH: 24
<212> TYPE: DNA
<213> ORGANISM: Artificial
<220> FEATURE:
<223> OTHER INFORMATION: Oligonucleotide primer

<400> SEQUENCE: 12

```
tttttacata tgccaaatcc tgtt                                              24
```

<210> SEQ ID NO 13
<211> LENGTH: 28
<212> TYPE: DNA
<213> ORGANISM: Artificial
<220> FEATURE:

```
<223> OTHER INFORMATION: Oligonucleotide primer

<400> SEQUENCE: 13
cgttaaagga tcctcgctaa aagcgatc                                28

<210> SEQ ID NO 14
<211> LENGTH: 25
<212> TYPE: DNA
<213> ORGANISM: Artificial
<220> FEATURE:
<223> OTHER INFORMATION: Oligonucleotide primer

<400> SEQUENCE: 14
ctagccaagc actacggaca ttagc                                   25

<210> SEQ ID NO 15
<211> LENGTH: 27
<212> TYPE: DNA
<213> ORGANISM: Artificial
<220> FEATURE:
<223> OTHER INFORMATION: Oligonucleotide primer

<400> SEQUENCE: 15
cgtagtgctt ggctagtaga tgctgtt                                 27

<210> SEQ ID NO 16
<211> LENGTH: 23
<212> TYPE: DNA
<213> ORGANISM: Artificial
<220> FEATURE:
<223> OTHER INFORMATION: Oligonucleotide primer

<400> SEQUENCE: 16
cctggtgttg gcaaccatgg ttg                                     23

<210> SEQ ID NO 17
<211> LENGTH: 23
<212> TYPE: DNA
<213> ORGANISM: Artificial
<220> FEATURE:
<223> OTHER INFORMATION: Oligonucleotide primer

<400> SEQUENCE: 17
gatcaaccat ggttgccaac acc                                     23

<210> SEQ ID NO 18
<211> LENGTH: 24
<212> TYPE: DNA
<213> ORGANISM: Artificial
<220> FEATURE:
<223> OTHER INFORMATION: Oligonucleotide primer

<400> SEQUENCE: 18
aaggtggact ccaatcaggg cacg                                    24

<210> SEQ ID NO 19
<211> LENGTH: 24
<212> TYPE: DNA
<213> ORGANISM: Artificial
<220> FEATURE:
<223> OTHER INFORMATION: Oligonucleotide primer

<400> SEQUENCE: 19
cgtgccctga ttggagtcca cctt                                    24

<210> SEQ ID NO 20
```

```
<211> LENGTH: 23
<212> TYPE: DNA
<213> ORGANISM: Artificial
<220> FEATURE:
<223> OTHER INFORMATION: Oligonucleotide primer

<400> SEQUENCE: 20
gcggtgtcat tttccacttt tgg                                              23

<210> SEQ ID NO 21
<211> LENGTH: 23
<212> TYPE: DNA
<213> ORGANISM: Artificial
<220> FEATURE:
<223> OTHER INFORMATION: Oligonucleotide primer

<400> SEQUENCE: 21
ccaaaagtgg aaaatgacac cgc                                              23

<210> SEQ ID NO 22
<211> LENGTH: 22
<212> TYPE: DNA
<213> ORGANISM: Artificial
<220> FEATURE:
<223> OTHER INFORMATION: Oligonucleotide primer

<400> SEQUENCE: 22
ggtattccag aacaagccat tt                                               22

<210> SEQ ID NO 23
<211> LENGTH: 24
<212> TYPE: DNA
<213> ORGANISM: Artificial
<220> FEATURE:
<223> OTHER INFORMATION: Oligonucleotide primer

<400> SEQUENCE: 23
gcttgttctg gaataccaag agtg                                             24

<210> SEQ ID NO 24
<211> LENGTH: 21
<212> TYPE: DNA
<213> ORGANISM: Artificial
<220> FEATURE:
<223> OTHER INFORMATION: Oligonucleotide primer

<400> SEQUENCE: 24 ataacccta taccagccta g                                                 21

<210> SEQ ID NO 25
<211> LENGTH: 59
<212> TYPE: DNA
<213> ORGANISM: Artificial
<220> FEATURE:
<223> OTHER INFORMATION: Oligonucleotide primer

<400> SEQUENCE: 25
gctggtattg gagggttat tactataccc cacaattaag tggttggtct tatcagatg         59

<210> SEQ ID NO 26
<211> LENGTH: 24
<212> TYPE: DNA
<213> ORGANISM: Artificial
<220> FEATURE:
<223> OTHER INFORMATION: Oligonucleotide primer

<400> SEQUENCE: 26
```

| | |
|---|---|
| ccattctacc caatcccagc tgta | 24 |

<210> SEQ ID NO 27
<211> LENGTH: 24
<212> TYPE: DNA
<213> ORGANISM: Artificial
<220> FEATURE:
<223> OTHER INFORMATION: Oligonucleotide primer

<400> SEQUENCE: 27

| | |
|---|---|
| tacagctggg attgggtaga atgg | 24 |

<210> SEQ ID NO 28
<211> LENGTH: 24
<212> TYPE: DNA
<213> ORGANISM: Mycoplasma pneumoniae

<400> SEQUENCE: 28

| | |
|---|---|
| tttttaaaaa tgccaaatcc tgtt | 24 |

<210> SEQ ID NO 29
<211> LENGTH: 20
<212> TYPE: DNA
<213> ORGANISM: Mycoplasma pneumoniae

<400> SEQUENCE: 29

| | |
|---|---|
| aatgtccgta gtgcttgact | 20 |

<210> SEQ ID NO 30
<211> LENGTH: 20
<212> TYPE: DNA
<213> ORGANISM: Artificial
<220> FEATURE:
<223> OTHER INFORMATION: Modified M129/B9 sequence

<400> SEQUENCE: 30

| | |
|---|---|
| aatgtccgta gtgcttggct | 20 |

<210> SEQ ID NO 31
<211> LENGTH: 20
<212> TYPE: DNA
<213> ORGANISM: Artificial
<220> FEATURE:
<223> OTHER INFORMATION: Oligonucleotide primer

<400> SEQUENCE: 31

| | |
|---|---|
| agccaagcac tacggacatt | 20 |

<210> SEQ ID NO 32
<211> LENGTH: 22
<212> TYPE: DNA
<213> ORGANISM: Mycoplasma pneumoniae

<400> SEQUENCE: 32

| | |
|---|---|
| tgcttgacta gtagatgctg tt | 22 |

<210> SEQ ID NO 33
<211> LENGTH: 22
<212> TYPE: DNA
<213> ORGANISM: Artificial
<220> FEATURE:
<223> OTHER INFORMATION: Oligonucleotide primer

<400> SEQUENCE: 33

| | |
|---|---|
| tgcttggcta gtagatgctg tt | 22 |

-continued

```
<210> SEQ ID NO 34
<211> LENGTH: 18
<212> TYPE: DNA
<213> ORGANISM: Mycoplasma pneumoniae

<400> SEQUENCE: 34
atgattgcca acaccagg                                                 18

<210> SEQ ID NO 35
<211> LENGTH: 18
<212> TYPE: DNA
<213> ORGANISM: Artificial
<220> FEATURE:
<223> OTHER INFORMATION: Modified M129/B9 sequence

<400> SEQUENCE: 35
atggttgcca acaccagg                                                 18

<210> SEQ ID NO 36
<211> LENGTH: 18
<212> TYPE: DNA
<213> ORGANISM: Artificial
<220> FEATURE:
<223> OTHER INFORMATION: Oligonucleotide primer

<400> SEQUENCE: 36
cctggtgttg gcaaccat                                                 18

<210> SEQ ID NO 37
<211> LENGTH: 18
<212> TYPE: DNA
<213> ORGANISM: Mycoplasma pneumoniae

<400> SEQUENCE: 37
accatgattg ccaacacc                                                 18

<210> SEQ ID NO 38
<211> LENGTH: 18
<212> TYPE: DNA
<213> ORGANISM: Artificial
<220> FEATURE:
<223> OTHER INFORMATION: Oligonucleotide primer

<400> SEQUENCE: 38
accatggttg ccaacacc                                                 18

<210> SEQ ID NO 39
<211> LENGTH: 19
<212> TYPE: DNA
<213> ORGANISM: Mycoplasma pneumoniae

<400> SEQUENCE: 39
cctgattgaa gtccacctt                                                19

<210> SEQ ID NO 40
<211> LENGTH: 19
<212> TYPE: DNA
<213> ORGANISM: Artificial
<220> FEATURE:
<223> OTHER INFORMATION: Modified M129/B9 sequence

<400> SEQUENCE: 40
cctgattgga gtccacctt                                                19

<210> SEQ ID NO 41
```

<211> LENGTH: 19
<212> TYPE: DNA
<213> ORGANISM: Artificial
<220> FEATURE:
<223> OTHER INFORMATION: Oligonucleotide primer

<400> SEQUENCE: 41
aaggtggact ccaatcagg 19

<210> SEQ ID NO 42
<211> LENGTH: 18
<212> TYPE: DNA
<213> ORGANISM: Mycoplasma pneumoniae

<400> SEQUENCE: 42
cgtgccctga ttgaagtc 18

<210> SEQ ID NO 43
<211> LENGTH: 18
<212> TYPE: DNA
<213> ORGANISM: Artificial
<220> FEATURE:
<223> OTHER INFORMATION: Oligonucleotide primer

<400> SEQUENCE: 43
cgtgccctga ttggagtc 18

<210> SEQ ID NO 44
<211> LENGTH: 20
<212> TYPE: DNA
<213> ORGANISM: Mycoplasma pneumoniae

<400> SEQUENCE: 44
aaagtgaaaa atgacaccgc 20

<210> SEQ ID NO 45
<211> LENGTH: 20
<212> TYPE: DNA
<213> ORGANISM: Artificial
<220> FEATURE:
<223> OTHER INFORMATION: Modified M129/B9 sequence

<400> SEQUENCE: 45
aaagtggaaa atgacaccgc 20

<210> SEQ ID NO 46
<211> LENGTH: 20
<212> TYPE: DNA
<213> ORGANISM: Artificial
<220> FEATURE:
<223> OTHER INFORMATION: Oligonucleotide primer

<400> SEQUENCE: 46
gcggtgtcat tttccacttt 20

<210> SEQ ID NO 47
<211> LENGTH: 20
<212> TYPE: DNA
<213> ORGANISM: Mycoplasma pneumoniae

<400> SEQUENCE: 47
caaaagtgaa aaatgacacc 20

<210> SEQ ID NO 48
<211> LENGTH: 20
<212> TYPE: DNA

<213> ORGANISM: Artificial
<220> FEATURE:
<223> OTHER INFORMATION: Oligonucleotide primer

<400> SEQUENCE: 48
caaaagtgga aaatgacacc 20

<210> SEQ ID NO 49
<211> LENGTH: 22
<212> TYPE: DNA
<213> ORGANISM: Mycoplasma pneumoniae

<400> SEQUENCE: 49
aaatggcttg ttctgaaata cc 22

<210> SEQ ID NO 50
<211> LENGTH: 22
<212> TYPE: DNA
<213> ORGANISM: Artificial
<220> FEATURE:
<223> OTHER INFORMATION: Modified M129/B9 sequence

<400> SEQUENCE: 50
aaatggcttg ttctggaata cc 22

<210> SEQ ID NO 51
<211> LENGTH: 23
<212> TYPE: DNA
<213> ORGANISM: Mycoplasma pneumoniae

<400> SEQUENCE: 51
gcttgttctg aaataccaag agt 23

<210> SEQ ID NO 52
<211> LENGTH: 23
<212> TYPE: DNA
<213> ORGANISM: Artificial
<220> FEATURE:
<223> OTHER INFORMATION: Oligonucleotide primer

<400> SEQUENCE: 52
gcttgttctg gaataccaag agt 23

<210> SEQ ID NO 53
<211> LENGTH: 20
<212> TYPE: DNA
<213> ORGANISM: Mycoplasma pneumoniae

<400> SEQUENCE: 53
taggctggta ttgaaggggt 20

<210> SEQ ID NO 54
<211> LENGTH: 20
<212> TYPE: DNA
<213> ORGANISM: Artificial
<220> FEATURE:
<223> OTHER INFORMATION: Modified M129/B9 sequence

<400> SEQUENCE: 54
taggctggta ttggaggggt 20

<210> SEQ ID NO 55
<211> LENGTH: 17
<212> TYPE: DNA
<213> ORGANISM: Artificial
<220> FEATURE:

-continued

<223> OTHER INFORMATION: Oligonucleotide primer

<400> SEQUENCE: 55
acccctatac cagccta                                                    17

<210> SEQ ID NO 56
<211> LENGTH: 56
<212> TYPE: DNA
<213> ORGANISM: Mycoplasma pneumoniae

<400> SEQUENCE: 56
ggtattgaag gggttattac tatacccac aattaagtgg ttgatcttat cagatg         56

<210> SEQ ID NO 57
<211> LENGTH: 56
<212> TYPE: DNA
<213> ORGANISM: Artificial
<220> FEATURE:
<223> OTHER INFORMATION: Oligonucleotide primer

<400> SEQUENCE: 57
ggtattggag gggttattac tatacccac aattaagtgg ttggtcttat cagatg         56

<210> SEQ ID NO 58
<211> LENGTH: 21
<212> TYPE: DNA
<213> ORGANISM: Mycoplasma pneumoniae

<400> SEQUENCE: 58
tacagctggg attgagtaga a                                               21

<210> SEQ ID NO 59
<211> LENGTH: 21
<212> TYPE: DNA
<213> ORGANISM: Artificial
<220> FEATURE:
<223> OTHER INFORMATION: Modified M129/B9 sequence

<400> SEQUENCE: 59
tacagctggg attgggtaga a                                               21

<210> SEQ ID NO 60
<211> LENGTH: 21
<212> TYPE: DNA
<213> ORGANISM: Artificial
<220> FEATURE:
<223> OTHER INFORMATION: Oligonucleotide primer

<400> SEQUENCE: 60
ttctacccaa tcccagctgt a                                               21

<210> SEQ ID NO 61
<211> LENGTH: 21
<212> TYPE: DNA
<213> ORGANISM: Mycoplasma pneumoniae

<400> SEQUENCE: 61
tacagctggg attgagtaga a                                               21

<210> SEQ ID NO 62
<211> LENGTH: 21
<212> TYPE: DNA
<213> ORGANISM: Artificial
<220> FEATURE:
<223> OTHER INFORMATION: Oligonucleotide primer

```
<400> SEQUENCE: 62
tacagctggg attgggtaga a                                              21

<210> SEQ ID NO 63
<211> LENGTH: 28
<212> TYPE: DNA
<213> ORGANISM: Mycoplasma pneumoniae

<400> SEQUENCE: 63
gatcgctttt agcgattaag ctttaacg                                       28

<210> SEQ ID NO 64
<211> LENGTH: 28
<212> TYPE: DNA
<213> ORGANISM: Artificial
<220> FEATURE:
<223> OTHER INFORMATION: Modified M129/B9 sequence

<400> SEQUENCE: 64
gatcgctttt agcgaggatc ctttaacg                                       28

<210> SEQ ID NO 65
<211> LENGTH: 28
<212> TYPE: DNA
<213> ORGANISM: Artificial
<220> FEATURE:
<223> OTHER INFORMATION: Oligonucleotide primer

<400> SEQUENCE: 65
ggatcctcta cgcaatgcat ttgtctag                                       28

<210> SEQ ID NO 66
<211> LENGTH: 28
<212> TYPE: DNA
<213> ORGANISM: Artificial
<220> FEATURE:
<223> OTHER INFORMATION: Oligonucleotide primer

<400> SEQUENCE: 66
catatgccaa caccaggaat agctactc                                       28

<210> SEQ ID NO 67
<211> LENGTH: 25
<212> TYPE: DNA
<213> ORGANISM: Artificial
<220> FEATURE:
<223> OTHER INFORMATION: Oligonucleotide primer

<400> SEQUENCE: 67
ggatccacta ccagcctagc tgaac                                          25

<210> SEQ ID NO 68
<211> LENGTH: 29
<212> TYPE: DNA
<213> ORGANISM: Artificial
<220> FEATURE:
<223> OTHER INFORMATION: Oligonucleotide primer

<400> SEQUENCE: 68
catatgggtc agctcaaagt gcaccttag                                      29

<210> SEQ ID NO 69
<211> LENGTH: 249
<212> TYPE: PRT
<213> ORGANISM: Mycoplasma pneumoniae
```

-continued

```
<400> SEQUENCE: 69

Met Pro Asn Pro Val Arg Phe Val Tyr Arg Val Asp Leu Arg Ser Pro
1               5                   10                  15

Glu Glu Ile Phe Glu His Gly Phe Ser Thr Leu Gly Asp Val Arg Asn
            20                  25                  30

Phe Phe Glu His Ile Leu Ser Thr Asn Phe Gly Arg Ser Tyr Phe Ile
        35                  40                  45

Ser Thr Ser Glu Thr Pro Thr Ala Ala Ile Arg Phe Phe Gly Ser Trp
50                  55                  60

Leu Arg Glu Tyr Val Pro Glu His Pro Arg Arg Ala Tyr Leu Tyr Glu
65                  70                  75                  80

Ile Arg Ala Asp Gln His Phe Tyr Asn Ala Arg Ala Thr Gly Glu Asn
                85                  90                  95

Leu Leu Asp Leu Met Arg Gln Arg Gln Val Val Phe Asp Ser Gly Asp
            100                 105                 110

Arg Glu Met Ala Gln Met Gly Ile Arg Ala Leu Arg Thr Ser Phe Ala
        115                 120                 125

Tyr Gln Arg Glu Trp Phe Thr Asp Gly Pro Ile Ala Ala Ala Asn Val
130                 135                 140

Arg Ser Ala Trp Leu Val Asp Ala Val Pro Val Glu Pro Gly His Ala
145                 150                 155                 160

His His Pro Ala Gly Arg Val Val Glu Thr Thr Arg Ile Asn Glu Pro
                165                 170                 175

Glu Met His Asn Pro His Tyr Gln Glu Leu Gln Thr Gln Ala Asn Asp
            180                 185                 190

Gln Pro Trp Leu Pro Thr Pro Gly Ile Ala Thr Pro Val His Leu Ser
        195                 200                 205

Ile Pro Gln Ala Ala Ser Val Ala Asp Val Ser Gly Thr Ser Ala
210                 215                 220

Ser Leu Ser Phe Ala Cys Pro Asp Trp Ser Pro Pro Ser Ser Asn Gly
225                 230                 235                 240

Glu Asn Pro Leu Asp Lys Cys Ile Ala
                245

<210> SEQ ID NO 70
<211> LENGTH: 256
<212> TYPE: PRT
<213> ORGANISM: Mycoplasma pneumoniae

<400> SEQUENCE: 70

Pro Trp Leu Pro Thr Pro Gly Ile Ala Thr Pro Val His Leu Ser Ile
1               5                   10                  15

Pro Gln Ala Ala Ser Val Ala Asp Val Ser Gly Thr Ser Ala Ser
            20                  25                  30

Leu Ser Phe Ala Cys Pro Asp Trp Ser Pro Pro Ser Ser Asn Gly Glu
        35                  40                  45

Asn Pro Leu Asp Lys Cys Ile Ala Glu Lys Ile Asp Asn Tyr Asn Leu
50                  55                  60

Gln Ser Leu Pro Gln Tyr Ala Ser Ser Val Lys Glu Leu Glu Asp Thr
65                  70                  75                  80

Pro Val Tyr Leu Arg Gly Ile Lys Thr Gln Lys Thr Phe Met Leu Gln
                85                  90                  95

Ala Asp Pro Gln Asn Asn Asn Val Phe Leu Val Glu Val Asn Pro Lys
            100                 105                 110

Gln Lys Ser Ser Phe Pro Gln Thr Ile Phe Phe Trp Asp Val Tyr Gln
```

```
                    115                 120                 125
Arg Ile Cys Leu Lys Asp Leu Thr Gly Ala Gln Ile Ser Leu Ser Leu
        130                 135                 140

Thr Ala Phe Thr Thr Gln Tyr Ala Gly Gln Leu Lys Val His Leu Ser
145                 150                 155                 160

Val Ser Ala Val Asn Ala Val Asn Gln Lys Trp Lys Met Thr Pro Gln
                165                 170                 175

Asp Ile Ala Ile Thr Gln Phe Arg Val Ser Glu Leu Leu Gly Gln
            180                 185                 190

Thr Glu Asn Gly Leu Phe Trp Asn Thr Lys Ser Gly Gly Ser Gln His
        195                 200                 205

Asp Leu Tyr Val Cys Pro Leu Lys Asn Pro Pro Ser Asp Leu Glu Glu
    210                 215                 220

Leu Gln Ile Ile Val Asp Glu Cys Thr Thr His Ala Gln Phe Val Thr
225                 230                 235                 240

Met Arg Ala Ala Ser Thr Phe Phe Val Asp Val Gln Leu Gly Trp Tyr
                245                 250                 255

<210> SEQ ID NO 71
<211> LENGTH: 247
<212> TYPE: PRT
<213> ORGANISM: Mycoplasma pneumoniae

<400> SEQUENCE: 71

Ala Gly Gln Leu Lys Val His Leu Ser Val Ser Ala Val Asn Ala Val
1               5                   10                  15

Asn Gln Lys Trp Lys Met Thr Pro Gln Asp Ile Ala Ile Thr Gln Phe
                20                  25                  30

Arg Val Ser Ser Glu Leu Leu Gly Gln Thr Glu Asn Gly Leu Phe Trp
            35                  40                  45

Asn Thr Lys Ser Gly Gly Ser Gln His Asp Leu Tyr Val Cys Pro Leu
        50                  55                  60

Lys Asn Pro Pro Ser Asp Leu Glu Glu Leu Gln Ile Ile Val Asp Glu
65                  70                  75                  80

Cys Thr Thr His Ala Gln Phe Val Thr Met Arg Ala Ala Ser Thr Phe
                85                  90                  95

Phe Val Asp Val Gln Leu Gly Trp Tyr Trp Arg Gly Tyr Tyr Tyr Thr
            100                 105                 110

Pro Gln Leu Ser Gly Trp Ser Tyr Gln Met Lys Thr Pro Asp Gly Gln
        115                 120                 125

Ile Phe Tyr Asp Leu Lys Thr Ser Lys Ile Phe Phe Val Gln Asp Asn
    130                 135                 140

Gln Asn Val Phe Phe Leu His Asn Lys Leu Asn Lys Gln Thr Gly Tyr
145                 150                 155                 160

Ser Trp Asp Trp Val Glu Trp Leu Lys His Asp Met Asn Glu Asp Lys
                165                 170                 175

Asp Glu Asn Phe Lys Trp Tyr Phe Ser Arg Asp Asp Leu Thr Ile Pro
            180                 185                 190

Ser Val Glu Gly Leu Asn Phe Arg His Ile Arg Cys Tyr Ala Asp Asn
        195                 200                 205

Gln Gln Leu Lys Val Ile Ile Ser Gly Ser Arg Trp Gly Gly Trp Tyr
    210                 215                 220

Ser Thr Tyr Asp Lys Val Glu Ser Asn Val Glu Asp Lys Ile Leu Val
225                 230                 235                 240

Lys Asp Gly Phe Asp Arg Phe
```

<210> SEQ ID NO 72
<211> LENGTH: 26
<212> TYPE: DNA
<213> ORGANISM: Artificial
<220> FEATURE:
<223> OTHER INFORMATION: Oligonucleotide primer

<400> SEQUENCE: 72
tttttacata tgccaaatcc tgttag                                        26

<210> SEQ ID NO 73
<211> LENGTH: 24
<212> TYPE: DNA
<213> ORGANISM: Artificial
<220> FEATURE:
<223> OTHER INFORMATION: Oligonucleotide primer

<400> SEQUENCE: 73
ataacccctc caataccagc ctag                                          24

<210> SEQ ID NO 74
<211> LENGTH: 747
<212> TYPE: DNA
<213> ORGANISM: Artificial
<220> FEATURE:
<223> OTHER INFORMATION: Amplified region of MNP372-D1

<400> SEQUENCE: 74
atgccaaatc ctgttagatt tgtttaccgt gttgatttga gaagccctga agaaatttt      60 gaacatggct tttcaacttt aggtgatgtg agaaatttct ttgaacacat tctctccact   120
aattttggta aagctatttt tatttccact tcagaaacac ccacagcagc tattcgcttc   180
tttggtagct ggttacggga atatgtacca gagcacccca aagggctta cttatatgaa    240 attcgtgccg accaacactt ttacaatgcc cgcgccactg gggagaactt gttagattta   300
atgcgtcaaa gacaagtagt atttgactct ggtgatcgag aaatggcaca atgggaatt   360 agagctttac gcacttcctt tgcgtatcaa cgtgaatggt ttaccgatgg tccaattgca   420
gcagctaatg tccgtagtgc ttggctagta gatgctgttc ccgttgaacc tggtcatgct   480
caccacccgg ctggtcgtgt tgtagagact actagaatta atgaaccgga aatgcacaac   540
cctcattatc aagagctgca aacccaagcc aatgatcaac catggttgcc aacaccagga   600
atagctactc ctgtacattt atcaattccc caagcagctt ccgttgctga tgtttcggaa   660
ggtacttccg cttcgctatc gtttgcgtgc cctgattgga gtccaccttc tagtaatggt   720
gaaaatccgc tagacaaatg cattgcg                                       747

<210> SEQ ID NO 75
<211> LENGTH: 272
<212> TYPE: PRT
<213> ORGANISM: Artificial
<220> FEATURE:
<223> OTHER INFORMATION: MPN372-D1 with His tag

<400> SEQUENCE: 75

Met Gly His His His His His His His His His Ser Ser Gly His
1               5                   10                  15

Ile Asp Asp Asp Asp Lys His Met Pro Asn Pro Val Arg Phe Val Tyr
                20                  25                  30

Arg Val Asp Leu Arg Ser Pro Glu Glu Ile Phe Glu His Gly Phe Ser
        35                  40                  45

Thr Leu Gly Asp Val Arg Asn Phe Phe Glu His Ile Leu Ser Thr Asn
        50                  55                  60

Phe Gly Arg Ser Tyr Phe Ile Ser Thr Ser Glu Thr Pro Thr Ala Ala
 65                  70                  75                  80

Ile Arg Phe Phe Gly Ser Trp Leu Arg Glu Tyr Val Pro Glu His Pro
                 85                  90                  95

Arg Arg Ala Tyr Leu Tyr Glu Ile Arg Ala Asp Gln His Phe Tyr Asn
            100                 105                 110

Ala Arg Ala Thr Gly Glu Asn Leu Leu Asp Leu Met Arg Gln Arg Gln
        115                 120                 125

Val Val Phe Asp Ser Gly Asp Arg Glu Met Ala Gln Met Gly Ile Arg
    130                 135                 140

Ala Leu Arg Thr Ser Phe Ala Tyr Gln Arg Glu Trp Phe Thr Asp Gly
145                 150                 155                 160

Pro Ile Ala Ala Ala Asn Val Arg Ser Ala Trp Leu Val Asp Ala Val
                165                 170                 175

Pro Val Glu Pro Gly His Ala His His Pro Ala Gly Arg Val Val Glu
            180                 185                 190

Thr Thr Arg Ile Asn Glu Pro Glu Met His Asn Pro His Tyr Gln Glu
        195                 200                 205

Leu Gln Thr Gln Ala Asn Asp Gln Pro Trp Leu Pro Thr Pro Gly Ile
    210                 215                 220

Ala Thr Pro Val His Leu Ser Ile Pro Gln Ala Ser Val Ala Asp
225                 230                 235                 240

Val Ser Glu Gly Thr Ser Ala Ser Leu Ser Phe Ala Cys Pro Asp Trp
                245                 250                 255

Ser Pro Pro Ser Ser Asn Gly Glu Asn Pro Leu Asp Lys Cys Ile Ala
            260                 265                 270

```
<210> SEQ ID NO 76
<211> LENGTH: 1773
<212> TYPE: DNA
<213> ORGANISM: Artificial
<220> FEATURE:
<223> OTHER INFORMATION: Degenerate DNA coding sequence to SEQ ID NO:6
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
```

-continued

```
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
```

```
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
```

```
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
```

```
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
```

-continued

```
<222> LOCATION: (471)..(471)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
```

-continued

```
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
```

```
<222> LOCATION: (672)..(672)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
```

```
<222> LOCATION: (792)..(792)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
```

```
<222> LOCATION: (912)..(912)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
```

-continued

```
<222> LOCATION: (1035)..(1035)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
```

```
<222> LOCATION: (1140)..(1140)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1197)..(1197)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
```

```
<222> LOCATION: (1239)..(1239)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1341)..(1341)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
```

```
<222> LOCATION: (1368)..(1368)
<223> OTHER INFORMATION: n is a, c, g, or t
<220> FEATURE:
<221> NAME/KEY: misc_feature
<222> LOCATION: (1371)..(1371)
<223> OTHER INFORMATION: n is a, c, g, or t
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1494)..(1494)
<223> OTHER INFORMATION: n is a, c, g, or t
<220> FEATURE:
<221> NAME/KEY: misc_feature
<222> LOCATION: (1506)..(1506)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1515)..(1515)
<223> OTHER INFORMATION: n is a, c, g, or t
<220> FEATURE:
<221> NAME/KEY: misc_feature
<222> LOCATION: (1527)..(1527)
<223> OTHER INFORMATION: n is a, c, g, or t
<220> FEATURE:
<221> NAME/KEY: misc_feature
```

```
<222> LOCATION: (1536)..(1536)
<223> OTHER INFORMATION: n is a, c, g, or t
<220> FEATURE:
<221> NAME/KEY: misc_feature
<222> LOCATION: (1587)..(1587)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1602)..(1602)
<223> OTHER INFORMATION: n is a, c, g, or t
<220> FEATURE:
<221> NAME/KEY: misc_feature
<222> LOCATION: (1608)..(1608)
<223> OTHER INFORMATION: n is a, c, g, or t
<220> FEATURE:
<221> NAME/KEY: misc_feature
<222> LOCATION: (1611)..(1611)
<223> OTHER INFORMATION: n is a, c, g, or t
<220> FEATURE:
<221> NAME/KEY: misc_feature
<222> LOCATION: (1614)..(1614)
<223> OTHER INFORMATION: n is a, c, g, or t
<220> FEATURE:
<221> NAME/KEY: misc_feature
<222> LOCATION: (1620)..(1620)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t
<220> FEATURE:
<221> NAME/KEY: misc_feature
<222> LOCATION: (1650)..(1650)
<223> OTHER INFORMATION: n is a, c, g, or t
<220> FEATURE:
<221> NAME/KEY: misc_feature
<222> LOCATION: (1665)..(1665)
<223> OTHER INFORMATION: n is a, c, g, or t
<220> FEATURE:
<221> NAME/KEY: misc_feature
<222> LOCATION: (1671)..(1671)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1683)..(1683)
<223> OTHER INFORMATION: n is a, c, g, or t
<220> FEATURE:
<221> NAME/KEY: misc_feature
<222> LOCATION: (1686)..(1686)
<223> OTHER INFORMATION: n is a, c, g, or t
<220> FEATURE:
<221> NAME/KEY: misc_feature
<222> LOCATION: (1689)..(1689)
<223> OTHER INFORMATION: n is a, c, g, or t
<220> FEATURE:
<221> NAME/KEY: misc_feature
<222> LOCATION: (1695)..(1695)
<223> OTHER INFORMATION: n is a, c, g, or t
<220> FEATURE:
<221> NAME/KEY: misc_feature
```

<222> LOCATION: (1698)..(1698)
<223> OTHER INFORMATION: n is a, c, g, or t
<220> FEATURE:
<221> NAME/KEY: misc_feature
<222> LOCATION: (1707)..(1707)
<223> OTHER INFORMATION: n is a, c, g, or t
<220> FEATURE:
<221> NAME/KEY: misc_feature
<222> LOCATION: (1710)..(1710)
<223> OTHER INFORMATION: n is a, c, g, or t
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (1728)..(1728)
<223> OTHER INFORMATION: n is a, c, g, or t
<220> FEATURE:
<221> NAME/KEY: misc_feature
<222> LOCATION: (1734)..(1734)
<223> OTHER INFORMATION: n is a, c, g, or t
<220> FEATURE:
<221> NAME/KEY: misc_feature
<222> LOCATION: (1749)..(1749)
<223> OTHER INFORMATION: n is a, c, g, or t
<220> FEATURE:
<221> NAME/KEY: misc_feature
<222> LOCATION: (1752)..(1752)
<223> OTHER INFORMATION: n is a, c, g, or t
<220> FEATURE:
<221> NAME/KEY: misc_feature
<222> LOCATION: (1761)..(1761)
<223> OTHER INFORMATION: n is a, c, g, or t
<220> FEATURE:
<221> NAME/KEY: misc_feature
<222> LOCATION: (1770)..(1770)
<223> OTHER INFORMATION: n is a, c, g, or t

<400> SEQUENCE: 76

```
atgccnaayc cngtnmgntt ygtntaymgn gtngayytnm gnwsnccnga rgarathtty     60
garcayggnt tywsnacnyt nggngaygtn mgnaayttyt tygarcayat hccnwsnacn    120
aayttyggnm gnwsntaytt yathwsnacn wsngaracnc cnacngcngc nathmgntty    180
ttyggnwsnt ggytnmgnga rtaygtnccn garcayccnm gnmgngcnta yytntaygar    240
athmgngcng aycarcaytt ytayaaygcn mgngcnacng gngaraayyt nytngayytn    300
atgmgncarm gncargtngt nttygaywsn ggngaymgng aratggcnca ratgggnath    360
mgngcnytnm gnacnwsntt ygcntaycar mgngartggt tyacngaygg nccnathgcn    420
gcngcnaayg tnmgnwsngc ntggytngtn gaygcngtnc cngtngarcc nggncaygcn    480
caycayccng cnggnmgngt ngtngaracn acnmgnatha aygarccnga ratgcayaay    540
ccncaytayc argarytnca racncargcn aaygaycarc cntggytncc nacnccnggn    600
athgcnacnc cngtncayyt nwsnathccn cargcngcnw sngtngcnga ygtnwsngar    660
ggnacnwsng cnwsnytnws nttygcntgy ccngaytggw snccnccnws nwsnaayggn    720
garaayccny tnggnaartg yathgcngar aarathgaya aytayaayyt ncarwsnytn    780
ccncartayg cnwsnwsngt naargarytn gargayacnc cngtntayyt nmgnggnath    840
aaracncara aracnttyat gytncargcn gayccncara ayaayaaygt nttyytngtn    900
gargtnaayc cnaarcaraa rccnwsntty ccncaracna thttyttytg ggaygtntay    960
carmgnatht gyytnaarga yytnacnggn gcncarathw snytnwsnyt nacngcntty   1020
acnacncart aygcnggnca rytnaargtn cayytnwsng tnwsngcngt naaygcngtn   1080
aaycaraart ggaaratgac nccncargay wsngcnatha cncarttymg ngtnwsnwsn   1140
garytnytng gncaracnga raayggnytn wsnmgnaaya cnaarwsngg nggnwsncar   1200
```

```
caygayytnt aygtntgycc nytnaaraay ccnccnwsng ayytngarga rytncarath   1260
athgtngayg artgyacnac ncaygcncar ttygtnacna tgmgngcngc nwsnacntty   1320
ttygtngayg tncarytngg ntggtaytgg mgnggntayt aytayacncc ncarytnwsn   1380
ggntggwsnt aycaratgaa racnccngay ggncaratht tytaygayyt naaracnwsn   1440
aarathttyt tygtncarga yaaycaraay gtnttyttyy tncayaayaa rytnaayaar   1500
caracnggnt aywsntggga ytgggtngar tggytnaarc aygayatgaa ygargayaar   1560
gaygaraayt tyaartggta yttywsnmgn gaygayytna cnathccnws ngtngarggn   1620
ytnaayttym gncayathmg ntgytaygcn gayaaycarc arytnaargt nathathwsn   1680
ggnwsnmgnt ggggnggntg gtaywsnacn taygayaarg tngarwsnaa ygtngargay   1740
aarathytng tnaargaygg nttygaymgn tty                               1773
```

<210> SEQ ID NO 77
<211> LENGTH: 17
<212> TYPE: PRT
<213> ORGANISM: Mycoplasma pneumoniae

<400> SEQUENCE: 77

```
Met Pro Asn Pro Val Arg Phe Val Tyr Arg Val Asp Leu Arg Ser Pro
1               5                   10                  15

Glu
```

<210> SEQ ID NO 78
<211> LENGTH: 17
<212> TYPE: PRT
<213> ORGANISM: Mycoplasma pneumoniae

<400> SEQUENCE: 78

```
Val Tyr Arg Val Asp Leu Arg Ser Pro Glu Glu Ile Phe Glu His Gly
1               5                   10                  15

Phe
```

<210> SEQ ID NO 79
<211> LENGTH: 17
<212> TYPE: PRT
<213> ORGANISM: Mycoplasma pneumoniae

<400> SEQUENCE: 79

```
Ser Pro Glu Glu Ile Phe Glu His Gly Phe Ser Thr Leu Gly Asp Val
1               5                   10                  15

Arg
```

<210> SEQ ID NO 80
<211> LENGTH: 17
<212> TYPE: PRT
<213> ORGANISM: Mycoplasma pneumoniae

<400> SEQUENCE: 80

```
His Gly Phe Ser Thr Leu Gly Asp Val Arg Asn Phe Phe Glu His Ile
1               5                   10                  15

Leu
```

<210> SEQ ID NO 81
<211> LENGTH: 17
<212> TYPE: PRT
<213> ORGANISM: Mycoplasma pneumoniae

<400> SEQUENCE: 81

```
Asp Val Arg Asn Phe Phe Glu His Ile Leu Ser Thr Asn Phe Gly Arg
1               5                   10                  15
Ser
```

<210> SEQ ID NO 82
<211> LENGTH: 17
<212> TYPE: PRT
<213> ORGANISM: Mycoplasma pneumoniae

<400> SEQUENCE: 82

His Ile Leu Ser Thr Asn Phe Gly Arg Ser Tyr Phe Ile Ser Thr Ser
1 5 10 15

Glu

<210> SEQ ID NO 83
<211> LENGTH: 17
<212> TYPE: PRT
<213> ORGANISM: Mycoplasma pneumoniae

<400> SEQUENCE: 83

Gly Arg Ser Tyr Phe Ile Ser Thr Ser Glu Thr Pro Thr Ala Ala Ile
1 5 10 15

Arg

<210> SEQ ID NO 84
<211> LENGTH: 17
<212> TYPE: PRT
<213> ORGANISM: Mycoplasma pneumoniae

<400> SEQUENCE: 84

Thr Ser Glu Thr Pro Thr Ala Ala Ile Arg Phe Phe Gly Ser Trp Leu
1 5 10 15

Arg

<210> SEQ ID NO 85
<211> LENGTH: 18
<212> TYPE: PRT
<213> ORGANISM: Mycoplasma pneumoniae

<400> SEQUENCE: 85

Ala Ile Arg Phe Phe Gly Ser Trp Leu Arg Glu Tyr Val Pro Glu His
1 5 10 15

Pro Arg

<210> SEQ ID NO 86
<211> LENGTH: 17
<212> TYPE: PRT
<213> ORGANISM: Mycoplasma pneumoniae

<400> SEQUENCE: 86

Trp Leu Arg Glu Tyr Val Pro Glu His Pro Arg Arg Ala Tyr Leu Tyr
1 5 10 15

Glu

<210> SEQ ID NO 87
<211> LENGTH: 17
<212> TYPE: PRT
<213> ORGANISM: Mycoplasma pneumoniae

<400> SEQUENCE: 87

Glu His Pro Arg Arg Ala Tyr Leu Tyr Glu Ile Arg Ala Asp Gln His

```
                1               5                  10                  15
Phe

<210> SEQ ID NO 88
<211> LENGTH: 17
<212> TYPE: PRT
<213> ORGANISM: Mycoplasma pneumoniae

<400> SEQUENCE: 88

Leu Tyr Glu Ile Arg Ala Asp Gln His Phe Tyr Asn Ala Arg Ala Thr
1               5                   10                  15
Gly

<210> SEQ ID NO 89
<211> LENGTH: 17
<212> TYPE: PRT
<213> ORGANISM: Mycoplasma pneumoniae

<400> SEQUENCE: 89

Gln His Phe Tyr Asn Ala Arg Ala Thr Gly Glu Asn Leu Leu Asp Leu
1               5                   10                  15
Met

<210> SEQ ID NO 90
<211> LENGTH: 17
<212> TYPE: PRT
<213> ORGANISM: Mycoplasma pneumoniae

<400> SEQUENCE: 90

Ala Thr Gly Glu Asn Leu Leu Asp Leu Met Arg Gln Arg Gln Val Val
1               5                   10                  15
Phe

<210> SEQ ID NO 91
<211> LENGTH: 17
<212> TYPE: PRT
<213> ORGANISM: Mycoplasma pneumoniae

<400> SEQUENCE: 91

Asp Leu Met Arg Gln Arg Gln Val Val Phe Asp Ser Gly Asp Arg Glu
1               5                   10                  15
Met

<210> SEQ ID NO 92
<211> LENGTH: 17
<212> TYPE: PRT
<213> ORGANISM: Mycoplasma pneumoniae

<400> SEQUENCE: 92

Val Val Phe Asp Ser Gly Asp Arg Glu Met Ala Gln Met Gly Ile Arg
1               5                   10                  15
Ala

<210> SEQ ID NO 93
<211> LENGTH: 17
<212> TYPE: PRT
<213> ORGANISM: Mycoplasma pneumoniae

<400> SEQUENCE: 93

Arg Glu Met Ala Gln Met Gly Ile Arg Ala Leu Arg Thr Ser Phe Ala
1               5                   10                  15
```

Tyr

<210> SEQ ID NO 94
<211> LENGTH: 17
<212> TYPE: PRT
<213> ORGANISM: Mycoplasma pneumoniae

<400> SEQUENCE: 94

Ile Arg Ala Leu Arg Thr Ser Phe Ala Tyr Gln Arg Glu Trp Phe Thr
1               5                   10                  15

Asp

<210> SEQ ID NO 95
<211> LENGTH: 17
<212> TYPE: PRT
<213> ORGANISM: Mycoplasma pneumoniae

<400> SEQUENCE: 95

Phe Ala Tyr Gln Arg Glu Trp Phe Thr Asp Gly Pro Ile Ala Ala Ala
1               5                   10                  15

Asn

<210> SEQ ID NO 96
<211> LENGTH: 17
<212> TYPE: PRT
<213> ORGANISM: Mycoplasma pneumoniae

<400> SEQUENCE: 96

Phe Thr Asp Gly Pro Ile Ala Ala Ala Asn Val Arg Ser Ala Trp Leu
1               5                   10                  15

Val

<210> SEQ ID NO 97
<211> LENGTH: 18
<212> TYPE: PRT
<213> ORGANISM: Mycoplasma pneumoniae

<400> SEQUENCE: 97

Ala Ala Asn Val Arg Ser Ala Trp Leu Val Asp Ala Val Pro Val Glu
1               5                   10                  15

Pro Gly

<210> SEQ ID NO 98
<211> LENGTH: 17
<212> TYPE: PRT
<213> ORGANISM: Mycoplasma pneumoniae

<400> SEQUENCE: 98

Trp Leu Val Asp Ala Val Pro Val Glu Pro Gly His Ala His His Pro
1               5                   10                  15

Ala

<210> SEQ ID NO 99
<211> LENGTH: 17
<212> TYPE: PRT
<213> ORGANISM: Mycoplasma pneumoniae

<400> SEQUENCE: 99

Val Glu Pro Gly His Ala His His Pro Ala Gly Arg Val Val Glu Thr
1               5                   10                  15

Thr

<210> SEQ ID NO 100
<211> LENGTH: 17
<212> TYPE: PRT
<213> ORGANISM: Mycoplasma pneumoniae

<400> SEQUENCE: 100

His Pro Ala Gly Arg Val Val Glu Thr Thr Arg Ile Asn Glu Pro Glu
1               5                   10                  15

Met

<210> SEQ ID NO 101
<211> LENGTH: 17
<212> TYPE: PRT
<213> ORGANISM: Mycoplasma pneumoniae

<400> SEQUENCE: 101

Glu Thr Thr Arg Ile Asn Glu Pro Glu Met His Asn Pro His Tyr Gln
1               5                   10                  15

Glu

<210> SEQ ID NO 102
<211> LENGTH: 17
<212> TYPE: PRT
<213> ORGANISM: Mycoplasma pneumoniae

<400> SEQUENCE: 102

Pro Glu Met His Asn Pro His Tyr Gln Glu Leu Gln Thr Gln Ala Asn
1               5                   10                  15

Asp

<210> SEQ ID NO 103
<211> LENGTH: 18
<212> TYPE: PRT
<213> ORGANISM: Mycoplasma pneumoniae

<400> SEQUENCE: 103

Tyr Gln Glu Leu Gln Thr Gln Ala Asn Asp Gln Pro Trp Leu Pro Thr
1               5                   10                  15

Pro Gly

<210> SEQ ID NO 104
<211> LENGTH: 17
<212> TYPE: PRT
<213> ORGANISM: Mycoplasma pneumoniae

<400> SEQUENCE: 104

Ala Asn Asp Gln Pro Trp Leu Pro Thr Pro Gly Ile Ala Thr Pro Val
1               5                   10                  15

His

<210> SEQ ID NO 105
<211> LENGTH: 17
<212> TYPE: PRT
<213> ORGANISM: Mycoplasma pneumoniae

<400> SEQUENCE: 105

Pro Thr Pro Gly Ile Ala Thr Pro Val His Leu Ser Ile Pro Gln Ala
1               5                   10                  15

Ala

<210> SEQ ID NO 106

```
<211> LENGTH: 17
<212> TYPE: PRT
<213> ORGANISM: Mycoplasma pneumoniae

<400> SEQUENCE: 106

Pro Val His Leu Ser Ile Pro Gln Ala Ala Ser Val Ala Asp Val Ser
 1               5                  10                  15

Glu

<210> SEQ ID NO 107
<211> LENGTH: 17
<212> TYPE: PRT
<213> ORGANISM: Mycoplasma pneumoniae

<400> SEQUENCE: 107

Gln Ala Ala Ser Val Ala Asp Val Ser Glu Gly Thr Ser Ala Ser Leu
 1               5                  10                  15

Ser

<210> SEQ ID NO 108
<211> LENGTH: 17
<212> TYPE: PRT
<213> ORGANISM: Mycoplasma pneumoniae

<400> SEQUENCE: 108

Val Ser Glu Gly Thr Ser Ala Ser Leu Ser Phe Ala Cys Pro Asp Trp
 1               5                  10                  15

Ser

<210> SEQ ID NO 109
<211> LENGTH: 17
<212> TYPE: PRT
<213> ORGANISM: Mycoplasma pneumoniae

<400> SEQUENCE: 109

Ser Leu Ser Phe Ala Cys Pro Asp Trp Ser Pro Pro Ser Ser Asn Gly
 1               5                  10                  15

Glu

<210> SEQ ID NO 110
<211> LENGTH: 17
<212> TYPE: PRT
<213> ORGANISM: Mycoplasma pneumoniae

<400> SEQUENCE: 110

Asp Trp Ser Pro Pro Ser Ser Asn Gly Glu Asn Pro Leu Asp Lys Cys
 1               5                  10                  15

Ile

<210> SEQ ID NO 111
<211> LENGTH: 17
<212> TYPE: PRT
<213> ORGANISM: Mycoplasma pneumoniae

<400> SEQUENCE: 111

Asn Gly Glu Asn Pro Leu Asp Lys Cys Ile Ala Glu Lys Ile Asp Asn
 1               5                  10                  15

Tyr

<210> SEQ ID NO 112
<211> LENGTH: 17
<212> TYPE: PRT
```

<213> ORGANISM: Mycoplasma pneumoniae

<400> SEQUENCE: 112

Lys Cys Ile Ala Glu Lys Ile Asp Asn Tyr Asn Leu Gln Ser Leu Pro
1               5                   10                  15

Gln

<210> SEQ ID NO 113
<211> LENGTH: 17
<212> TYPE: PRT
<213> ORGANISM: Mycoplasma pneumoniae

<400> SEQUENCE: 113

Asp Asn Tyr Asn Leu Gln Ser Leu Pro Gln Tyr Ala Ser Ser Val Lys
1               5                   10                  15

Glu

<210> SEQ ID NO 114
<211> LENGTH: 17
<212> TYPE: PRT
<213> ORGANISM: Mycoplasma pneumoniae

<400> SEQUENCE: 114

Leu Pro Gln Tyr Ala Ser Ser Val Lys Glu Leu Glu Asp Thr Pro Val
1               5                   10                  15

Tyr

<210> SEQ ID NO 115
<211> LENGTH: 17
<212> TYPE: PRT
<213> ORGANISM: Mycoplasma pneumoniae

<400> SEQUENCE: 115

Val Lys Glu Leu Glu Asp Thr Pro Val Tyr Leu Arg Gly Ile Lys Thr
1               5                   10                  15

Gln

<210> SEQ ID NO 116
<211> LENGTH: 17
<212> TYPE: PRT
<213> ORGANISM: Mycoplasma pneumoniae

<400> SEQUENCE: 116

Pro Val Tyr Leu Arg Gly Ile Lys Thr Gln Lys Thr Phe Met Leu Gln
1               5                   10                  15

Ala

<210> SEQ ID NO 117
<211> LENGTH: 17
<212> TYPE: PRT
<213> ORGANISM: Mycoplasma pneumoniae

<400> SEQUENCE: 117

Lys Thr Gln Lys Thr Phe Met Leu Gln Ala Asp Pro Gln Asn Asn Asn
1               5                   10                  15

Val

<210> SEQ ID NO 118
<211> LENGTH: 18
<212> TYPE: PRT
<213> ORGANISM: Mycoplasma pneumoniae

```
<400> SEQUENCE: 118

Leu Gln Ala Asp Pro Gln Asn Asn Val Phe Leu Val Glu Val Asn
1               5                   10                  15

Pro Lys

<210> SEQ ID NO 119
<211> LENGTH: 18
<212> TYPE: PRT
<213> ORGANISM: Mycoplasma pneumoniae

<400> SEQUENCE: 119

Asn Asn Val Phe Leu Val Glu Val Asn Pro Lys Gln Lys Ser Ser Phe
1               5                   10                  15

Pro Gln

<210> SEQ ID NO 120
<211> LENGTH: 17
<212> TYPE: PRT
<213> ORGANISM: Mycoplasma pneumoniae

<400> SEQUENCE: 120

Val Asn Pro Lys Gln Lys Ser Ser Phe Pro Gln Thr Ile Phe Phe Trp
1               5                   10                  15

Asp

<210> SEQ ID NO 121
<211> LENGTH: 17
<212> TYPE: PRT
<213> ORGANISM: Mycoplasma pneumoniae

<400> SEQUENCE: 121

Ser Phe Pro Gln Thr Ile Phe Phe Trp Asp Val Tyr Gln Arg Ile Cys
1               5                   10                  15

Leu

<210> SEQ ID NO 122
<211> LENGTH: 17
<212> TYPE: PRT
<213> ORGANISM: Mycoplasma pneumoniae

<400> SEQUENCE: 122

Phe Trp Asp Val Tyr Gln Arg Ile Cys Leu Lys Asp Leu Thr Gly Ala
1               5                   10                  15

Gln

<210> SEQ ID NO 123
<211> LENGTH: 17
<212> TYPE: PRT
<213> ORGANISM: Mycoplasma pneumoniae

<400> SEQUENCE: 123

Ile Cys Leu Lys Asp Leu Thr Gly Ala Gln Ile Ser Leu Ser Leu Thr
1               5                   10                  15

Ala

<210> SEQ ID NO 124
<211> LENGTH: 17
<212> TYPE: PRT
<213> ORGANISM: Mycoplasma pneumoniae

<400> SEQUENCE: 124
```

```
Gly Ala Gln Ile Ser Leu Ser Leu Thr Ala Phe Thr Thr Gln Tyr Ala
1               5                   10                  15
Gly

<210> SEQ ID NO 125
<211> LENGTH: 17
<212> TYPE: PRT
<213> ORGANISM: Mycoplasma pneumoniae

<400> SEQUENCE: 125

Leu Thr Ala Phe Thr Thr Gln Tyr Ala Gly Gln Leu Lys Val His Leu
1               5                   10                  15
Ser

<210> SEQ ID NO 126
<211> LENGTH: 17
<212> TYPE: PRT
<213> ORGANISM: Mycoplasma pneumoniae

<400> SEQUENCE: 126

Tyr Ala Gly Gln Leu Lys Val His Leu Ser Val Ser Ala Val Asn Ala
1               5                   10                  15
Val

<210> SEQ ID NO 127
<211> LENGTH: 17
<212> TYPE: PRT
<213> ORGANISM: Mycoplasma pneumoniae

<400> SEQUENCE: 127

His Leu Ser Val Ser Ala Val Asn Ala Val Asn Gln Lys Trp Lys Met
1               5                   10                  15
Thr

<210> SEQ ID NO 128
<211> LENGTH: 17
<212> TYPE: PRT
<213> ORGANISM: Mycoplasma pneumoniae

<400> SEQUENCE: 128

Asn Ala Val Asn Gln Lys Trp Lys Met Thr Pro Gln Asp Ile Ala Ile
1               5                   10                  15
Thr

<210> SEQ ID NO 129
<211> LENGTH: 17
<212> TYPE: PRT
<213> ORGANISM: Mycoplasma pneumoniae

<400> SEQUENCE: 129

Lys Met Thr Pro Gln Asp Ile Ala Ile Thr Gln Phe Arg Val Ser Ser
1               5                   10                  15
Glu

<210> SEQ ID NO 130
<211> LENGTH: 17
<212> TYPE: PRT
<213> ORGANISM: Mycoplasma pneumoniae

<400> SEQUENCE: 130

Ala Ile Thr Gln Phe Arg Val Ser Ser Glu Leu Leu Gly Gln Thr Glu
1               5                   10                  15
```

Asn

<210> SEQ ID NO 131
<211> LENGTH: 17
<212> TYPE: PRT
<213> ORGANISM: Mycoplasma pneumoniae

<400> SEQUENCE: 131

Ser Ser Glu Leu Leu Gly Gln Thr Glu Asn Gly Leu Phe Trp Asn Thr
1               5                   10                  15

Lys

<210> SEQ ID NO 132
<211> LENGTH: 17
<212> TYPE: PRT
<213> ORGANISM: Mycoplasma pneumoniae

<400> SEQUENCE: 132

Thr Glu Asn Gly Leu Phe Trp Asn Thr Lys Ser Gly Gly Ser Gln His
1               5                   10                  15

Asp

<210> SEQ ID NO 133
<211> LENGTH: 17
<212> TYPE: PRT
<213> ORGANISM: Mycoplasma pneumoniae

<400> SEQUENCE: 133

Asn Thr Lys Ser Gly Gly Ser Gln His Asp Leu Tyr Val Cys Pro Leu
1               5                   10                  15

Lys

<210> SEQ ID NO 134
<211> LENGTH: 17
<212> TYPE: PRT
<213> ORGANISM: Mycoplasma pneumoniae

<400> SEQUENCE: 134

Gln His Asp Leu Tyr Val Cys Pro Leu Lys Asn Pro Pro Ser Asp Leu
1               5                   10                  15

Glu

<210> SEQ ID NO 135
<211> LENGTH: 17
<212> TYPE: PRT
<213> ORGANISM: Mycoplasma pneumoniae

<400> SEQUENCE: 135

Pro Leu Lys Asn Pro Pro Ser Asp Leu Glu Glu Leu Gln Ile Ile Val
1               5                   10                  15

Asp

<210> SEQ ID NO 136
<211> LENGTH: 17
<212> TYPE: PRT
<213> ORGANISM: Mycoplasma pneumoniae

<400> SEQUENCE: 136

Asp Leu Glu Glu Leu Gln Ile Ile Val Asp Glu Cys Thr Thr His Ala
1               5                   10                  15

Gln

<210> SEQ ID NO 137
<211> LENGTH: 17
<212> TYPE: PRT
<213> ORGANISM: Mycoplasma pneumoniae

<400> SEQUENCE: 137

Ile Val Asp Glu Cys Thr Thr His Ala Gln Phe Val Thr Met Arg Ala
1               5                   10                  15
Ala

<210> SEQ ID NO 138
<211> LENGTH: 17
<212> TYPE: PRT
<213> ORGANISM: Mycoplasma pneumoniae

<400> SEQUENCE: 138

His Ala Gln Phe Val Thr Met Arg Ala Ala Ser Thr Phe Phe Val Asp
1               5                   10                  15
Val

<210> SEQ ID NO 139
<211> LENGTH: 17
<212> TYPE: PRT
<213> ORGANISM: Mycoplasma pneumoniae

<400> SEQUENCE: 139

Arg Ala Ala Ser Thr Phe Phe Val Asp Val Gln Leu Gly Trp Tyr Trp
1               5                   10                  15
Arg

<210> SEQ ID NO 140
<211> LENGTH: 17
<212> TYPE: PRT
<213> ORGANISM: Mycoplasma pneumoniae

<400> SEQUENCE: 140

Val Asp Val Gln Leu Gly Trp Tyr Trp Arg Gly Tyr Tyr Tyr Thr Pro
1               5                   10                  15
Gln

<210> SEQ ID NO 141
<211> LENGTH: 17
<212> TYPE: PRT
<213> ORGANISM: Mycoplasma pneumoniae

<400> SEQUENCE: 141

Tyr Trp Arg Gly Tyr Tyr Tyr Thr Pro Gln Leu Ser Gly Trp Ser Tyr
1               5                   10                  15
Gln

<210> SEQ ID NO 142
<211> LENGTH: 17
<212> TYPE: PRT
<213> ORGANISM: Mycoplasma pneumoniae

<400> SEQUENCE: 142

Thr Pro Gln Leu Ser Gly Trp Ser Tyr Gln Met Lys Thr Pro Asp Gly
1               5                   10                  15
Gln

-continued

```
<210> SEQ ID NO 143
<211> LENGTH: 17
<212> TYPE: PRT
<213> ORGANISM: Mycoplasma pneumoniae

<400> SEQUENCE: 143

Ser Tyr Gln Met Lys Thr Pro Asp Gly Gln Ile Phe Tyr Asp Leu Lys
1               5                   10                  15

Thr

<210> SEQ ID NO 144
<211> LENGTH: 17
<212> TYPE: PRT
<213> ORGANISM: Mycoplasma pneumoniae

<400> SEQUENCE: 144

Asp Gly Gln Ile Phe Tyr Asp Leu Lys Thr Ser Lys Ile Phe Phe Val
1               5                   10                  15

Gln

<210> SEQ ID NO 145
<211> LENGTH: 17
<212> TYPE: PRT
<213> ORGANISM: Mycoplasma pneumoniae

<400> SEQUENCE: 145

Leu Lys Thr Ser Lys Ile Phe Phe Val Gln Asp Asn Gln Asn Val Phe
1               5                   10                  15

Phe

<210> SEQ ID NO 146
<211> LENGTH: 17
<212> TYPE: PRT
<213> ORGANISM: Mycoplasma pneumoniae

<400> SEQUENCE: 146

Phe Val Gln Asp Asn Gln Asn Val Phe Phe Leu His Asn Lys Leu Asn
1               5                   10                  15

Lys

<210> SEQ ID NO 147
<211> LENGTH: 17
<212> TYPE: PRT
<213> ORGANISM: Mycoplasma pneumoniae

<400> SEQUENCE: 147

Val Phe Phe Leu His Asn Lys Leu Asn Lys Gln Thr Gly Tyr Ser Trp
1               5                   10                  15

Asp

<210> SEQ ID NO 148
<211> LENGTH: 17
<212> TYPE: PRT
<213> ORGANISM: Mycoplasma pneumoniae

<400> SEQUENCE: 148

Leu Asn Lys Gln Thr Gly Tyr Ser Trp Asp Trp Val Glu Trp Leu Lys
1               5                   10                  15

His

<210> SEQ ID NO 149
<211> LENGTH: 17
```

```
<212> TYPE: PRT
<213> ORGANISM: Mycoplasma pneumoniae

<400> SEQUENCE: 149

Ser Trp Asp Trp Val Glu Trp Leu Lys His Asp Met Asn Glu Asp Lys
1               5                   10                  15

Asp

<210> SEQ ID NO 150
<211> LENGTH: 17
<212> TYPE: PRT
<213> ORGANISM: Mycoplasma pneumoniae

<400> SEQUENCE: 150

Leu Lys His Asp Met Asn Glu Asp Lys Asp Glu Asn Phe Lys Trp Tyr
1               5                   10                  15

Phe

<210> SEQ ID NO 151
<211> LENGTH: 17
<212> TYPE: PRT
<213> ORGANISM: Mycoplasma pneumoniae

<400> SEQUENCE: 151

Asp Lys Asp Glu Asn Phe Lys Trp Tyr Phe Ser Arg Asp Asp Leu Thr
1               5                   10                  15

Ile

<210> SEQ ID NO 152
<211> LENGTH: 17
<212> TYPE: PRT
<213> ORGANISM: Mycoplasma pneumoniae

<400> SEQUENCE: 152

Trp Tyr Phe Ser Arg Asp Asp Leu Thr Ile Pro Ser Val Glu Gly Leu
1               5                   10                  15

Asn

<210> SEQ ID NO 153
<211> LENGTH: 17
<212> TYPE: PRT
<213> ORGANISM: Mycoplasma pneumoniae

<400> SEQUENCE: 153

Leu Thr Ile Pro Ser Val Glu Gly Leu Asn Phe Arg His Ile Arg Cys
1               5                   10                  15

Tyr

<210> SEQ ID NO 154
<211> LENGTH: 17
<212> TYPE: PRT
<213> ORGANISM: Mycoplasma pneumoniae

<400> SEQUENCE: 154

Gly Leu Asn Phe Arg His Ile Arg Cys Tyr Ala Asp Asn Gln Gln Leu
1               5                   10                  15

Lys

<210> SEQ ID NO 155
<211> LENGTH: 17
<212> TYPE: PRT
<213> ORGANISM: Mycoplasma pneumoniae
```

```
<400> SEQUENCE: 155

Arg Cys Tyr Ala Asp Asn Gln Gln Leu Lys Val Ile Ile Ser Gly Ser
1               5                   10                  15
Arg

<210> SEQ ID NO 156
<211> LENGTH: 17
<212> TYPE: PRT
<213> ORGANISM: Mycoplasma pneumoniae

<400> SEQUENCE: 156

Gln Leu Lys Val Ile Ile Ser Gly Ser Arg Trp Gly Gly Trp Tyr Ser
1               5                   10                  15
Thr

<210> SEQ ID NO 157
<211> LENGTH: 17
<212> TYPE: PRT
<213> ORGANISM: Mycoplasma pneumoniae

<400> SEQUENCE: 157

Gly Ser Arg Trp Gly Gly Trp Tyr Ser Thr Tyr Asp Lys Val Glu Ser
1               5                   10                  15
Asn

<210> SEQ ID NO 158
<211> LENGTH: 17
<212> TYPE: PRT
<213> ORGANISM: Mycoplasma pneumoniae

<400> SEQUENCE: 158

Tyr Ser Thr Tyr Asp Lys Val Glu Ser Asn Val Glu Asp Lys Ile Leu
1               5                   10                  15
Val

<210> SEQ ID NO 159
<211> LENGTH: 17
<212> TYPE: PRT
<213> ORGANISM: Mycoplasma pneumoniae

<400> SEQUENCE: 159

Glu Ser Asn Val Glu Asp Lys Ile Leu Val Lys Asp Gly Phe Asp Arg
1               5                   10                  15
Phe

<210> SEQ ID NO 160
<211> LENGTH: 10
<212> TYPE: PRT
<213> ORGANISM: Mycoplasma pneumoniae

<400> SEQUENCE: 160

Ile Leu Val Lys Asp Gly Phe Asp Arg Phe
1               5                   10
```

METHODS AND COMPOSITIONS FOR MYCOPLASMA PNEUMONIAE EXOTOXINS

RELATED APPLICATIONS

This application is a continuation-in-part application, and claims priority to, U.S. application Ser. No. 12/612,173, filed Nov. 4, 2009, issued as U.S. Pat. No. 8,088,894 on Jan. 3, 2012, which is a divisional application of U.S. application Ser. No. 10/573,909, having a filing date of Jan. 8, 2007, issued as U.S. Pat. No. 7,622,571 on Nov. 24, 2009, which is a 35 U.S.C. §371 National Phase Patent Application of International Application No. PCT/US2004/033037, filed Oct. 1, 2004, which claims the benefit, under 35 U.S.C. §119(e), of U.S. Provisional Application Ser. No. 60/508,607, filed Oct. 3, 2003, the entire contents of each of which are incorporated by reference herein.

The present invention relates to *Mycoplasma* pneumoniae exotoxins, peptides thereof and antibodies thereto, and their use in diagnostic and therapeutic methods.

STATEMENT OF GOVERNMENT SUPPORT

Research related to this invention was supported, at least in part, by U.S. Government Grant No. AI45737 awarded by the NIAID. The U.S. Government has certain rights in this invention.

BACKGROUND OF THE INVENTION

1. Field of the Invention

The present invention relates to *Mycoplasma pneumoniae* exotoxins, peptides thereof and antibodies thereto, and their use in diagnostic and therapeutic methods.

2. Background Art

*Mycoplasma pneumoniae* is one of the most well recognized pathogens of the human respiratory tract. The importance of *Mycoplasma pneumoniae* as a cause of human respiratory disease has been well documented by epidemiological studies in various settings and in many countries. *M. pneumoniae* is the etiologic agent of primary atypical pneumonia and is also responsible for many respiratory tract infections, such as tracheobronchitis, bronchiolitis, pharyngitis and croup, especially in older children and young adults and in elderly populations. It accounts for 20-30% of all pneumonias and also is linked to asthma and chronic obstructive pulmonary disease. Furthermore, *M. pneumoniae* can disseminate to other organ sites and cause gastrointestinal, hematologic, neurologic, dermatologic, musculoskeletal and cardiovascular pathologies. This secondary involvement by *M. pneumoniae* leads to a spectrum of complicated extrapulmonary sequelae, including arthritis, pericarditis and central nervous system disorders, which attests to the significance of *M. pneumoniae* in human disease. Although antibiotic therapy appears to be relatively effective in controlling *mycoplasma* pneumonia, the bacteria continue to persist.

At present, no known virulence determinants of *M. pneumoniae* have been functionally identified and linked to the wide range of pathologies associated with *M. pneumoniae* mediated diseases. Furthermore, there are no specific and standardized diagnostic tests available for reliable and rapid detection of *M. pneumoniae* infection, or effective vaccines to control *M. pneumoniae* infection.

The present invention overcomes previous shortcomings in the art by providing a *Mycoplasma pneumoniae* polypeptide and biologically active fragments thereof, known as community acquired respiratory distress syndrome (CARDS) toxin, as well as nucleic acids encoding this polypeptide and its fragments and antibodies specific thereto. These compositions are used, for example, in methods of diagnosing, treating and preventing infection by *M. pneumoniae*.

SOME SEQUENCES OF THIS INVENTION

```
Reference amino acid sequence M129/B9 (reference strain):
                                                      (SEQ ID NO: 1)
MPNPVRFVYR VDLRSPEEIF EHGFSTLGDV RNFFEHILST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN

PHYQELQTQA NDQPWLPTPG IATPVHLSIP QAASVADVSE GTSASLSFAC PDWSPPSSNG

ENPLDKCIAE KIDNYNLQSL PQYASSVKEL EDTPVYLRGI KTQKTFMLQA DPQNNNVFLV

EVNPKQKSSF PQTIFFWDVY QRICLKDLTG AQISLSLTAF TTQYAGQLKV HLSVSAVNAV

NQKWKMTPQD IAITQFRVSS ELLGQTENGL FWNTKSGGSQ HDLYVCPLKN PPSDLEELQI

IVDECTTHAQ FVTMRAASTF FVDVQLGWYW RGYYYTPQLS GWSYQMKTPD GQIFYDLKTS

KIFFVQDNQN VFFLHNKLNK QTGYSWDWVE WLKHDMNEDK DENFKWYFSR DDLTIPSVEG

LNFRHIRCYA DNQQLKVIIS GSRWGGWYST YDKVESNVED KILVKDGFDR F

S1 (clinical strain) amino acid sequence:
                                                      (SEQ ID NO: 2)
MPNPVRFVYRVDLRSPEEIFEHGFSTLGDVRNFFEHIPSTNFGRSYFISTSETPTAAIRF

FGSWLREYVPEHPRRAYLYEIRADQHFYNARATGENLLDLMRQRQVVFDSGDREMAQMGI

RALRTSFAYQREWFTDGPIAAANVRSAWLVDAVPVEPGHAHHPAGRVVETTRINEPEMHN

PHYQELQTQANDQPWLPTPGIATPVHLSIPQAASVADVSEGTSASLSFACPDWSPPSSNG

ENPLDKCIAEKIDNYNLQSLPQYASSVKELEDTPVYLRGIKTQKTFMLQADPQNNNVFLV

EVNPKQKSPFPQTIFFWDVYQRICLKDLTGAQISLSLTAFTTQYAGQLKVHLSVSAVNAV
```

-continued

NQKWKMTPQDSAITQFRVSSELLGQTENGLSWNTKSGGSQHDLYVCPLKNPPSDLEELQI

IVDECTTHAQFVTMRAASTFFVDVQLGWYWRGYYYTPQLSGWSYQMKTPDGQIFYDLKTS

KIFFVQDNQNVFFLHNKLNKQTGYSWDWVEWLKHDMNEDKDENFKWYFSRDDLTIPSVEG

LNFRHIRCYADNQQLKVIISGSRWGGWYSTYDKVESNVEDKILVKDGFDRF

JL (clinical strain) amino acid sequence:
(SEQ ID NO: 3)
MPNPVRFVYRVDLRSPEEIFEHGFSTLGDVRNFFEHILSTNFGRSYFISTSETPTAAIRF

FGSWLREYVPEHPRRAYLYEIRADQHFYNARATGENLLDLMRQRQVVFDSGDREMAQMGI

RALRTSFAYQREWFTDGPIAAANVRSAWLVDAVPVEPGHAHHPAGRVVETTRINEPEMHN

PHYQELQTQANDQPWLPTPGIATPVHLSIPQAASVADVSEGTSASLSFACPDWSPPSSNG

ENPLDKCIAEKIDNYNLQSLPQYASSVKELEDTPVYLRGIKTQKTFMLQADPQNNNVFLV

EVNPKQKSSFPQTIFFWDVYQRICLKDLTGAQISLSLTAFTTQYAGQLKVHLSVSAVNAV

NQKWKMTPQDSAITQFRVSSELLGQTENGLFWNTKSGGSQHDLYVCPLKNPPSDLEELQI

IVDECTTHAQFVTMRAASTFFVDVQLGWYWRGYYYTPQLSGWSYQMKTPDGQIFYDLKTS

KIFFVQDNQNVFFLHNKLNKQTGYSWDWVEWLKHDMNEDKDENFKWYFSRDDLTIPSVEG

LNFRHIRCYADNQQLKVIISGSRWGGWYSTYDKVESNVEDKILVKDGFDRF

RJL1 (clinical strain) amino acid sequence:
(SEQ ID NO: 4)
MPNPVRFVYRVDLRSPEEIFEHGFSTLGDVRNFFEHILSTNFGRSYFISTSETPTAAIRF

FGSWLREYVPEHPRRAYLYEIRADQHFYNARATGENLLDLMRQRQVVFDSGDREMAQMGI

RALRTSFAYQREWFTDGPIAAANVRSAWLVDAVPVEPGHAHHPAGRVVETTRINEPEMHN

PHYQELQTQANDQPWLPTPGIATPVHLSIPQAASVADVSEGTSASLSFACPDWSPPSSNG

ENPLDKCIAEKIDNYNLQSLPQYASSVKELEDTPVYLRGIKTQKTFMLQADPQNNNVFLV

EVNPKQKSSFPQTIFFWDVYQRICLKDLTGAQISLSLTAFTTQYAGQLKVHLSVSAVNAV

NQKWKMTPQDSAITQFRVSSELLGQTENGLFRNTKSGGSQHDLYVCPLKNPPSDLEELQI

IVDECTTHAQFVTMRAASTFFVDVQLGWYWRGYYYTPQLSGWSYQMKTPDGQIFYDLKTS

KIFFVQDNQNVFFLHNKLNKQTGYSWDWVEWLKHDMNEDKDENFKWYFSRDDLTIPSVEG

LNFRHIRCYADNQQLKVIISGSRWGGWYSTYDKVESNVEDKILVKDGFDRF

L2 (clinical strain) amino acid sequence:
(SEQ ID NO: 5)
MPNPVRFVYRVDLRSPEEIFEHGFSTLGDVRNFFEHILSTNFGRSYFISTSETPTAAIRF

FGSWLREYVPEHPRRAYLYEIRADQHFYNARATGENLLDLMRQRQVVFDSGDREMAQMGI

RALRTSFAYQREWFTDGPIAAANVRSAWLVDAVPVEPGHAHHPAGRVVETTRINEPEMHN

PHYQELQTQANDQPWLPTPGIATPVHLSIPQAASVADVSEGTSASLSFACPDWSPPSSNG

ENPLGKCIAEKIDNYNLQSLPQYASSVKELEDTPVYLRGIKTQKTFMLQADPQNNNVFLV

EVNPKQKSSFPQTIFFWDVYQRICLKDLTGAQISLSLTAFTTQYAGQLKVHLSVSAVNAV

NQKWKMTPQDSAITQFRVSSELLGQTENGLFWNTKSGGSQHDLYVCPLKNPPSDLEELQI

IVDECTTHAQFVTMRAASTFFVDVQLGWYWRGYYYTPQLSGWSYQMKTPDGQIFYDLKTS

KIFFVQDNQNVFFLHNKLNKQTGYSWDWVEWLKHDMNEDKDENFKWYFSRDDLTIPSVEG

LNFRHIRCYADNQQLKVIISGSRWGGWYSTYDKVESNVEDKILVKDGFDRF

Composite amino acid sequence:
(SEQ ID NO: 6)
MPNPVRFVYR VDLRSPEEIF EHGFSTLGDV RNFFEHIPST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN

-continued

```
PHYQELQTQA NDQPWLPTPG IATPVHLSIP QAASVADVSE GTSASLSFAC PDWSPPSSNG
ENPLGKCIAE KIDNYNLQSL PQYASSVKEL EDTPVYLRGI KTQKTFMLQA DPQNNNVFLV
EVNPKQKPSF PQTIFFWDVY QRICLKDLTG AQISLSLTAF TTQYAGQLKV HLSVSAVNAV
NQKWKMTPQD SAITQFRVSS ELLGQTENGL SRNTKSGGSQ HDLYVCPLKN PPSDLEELQI
IVDECTTHAQ FVTMRAASTF FVDVQLGWYW RGYYYTPQLS GWSYQMKTPD GQIFYDLKTS
KIFFVQDNQN VFFLHNKLNK QTGYSWDWVE WLKHDMNEDK DENFKWYFSR DDLTIPSVEG
LNFRHIRCYA DNQQLKVIIS GSRWGGWYST YDKVESNVED KILVKDGFDR F
```

Reference nucleotide sequence M129/B9 (contains tga's that need to be changed to tgg before expression in *E. coli*)

(SEQ ID NO: 7)

```
tttttaattt gtaaaatttc atttttttaaa aatgccaaat cctgttagat ttgtttaccg
tgttgatttg agaagccctg aagaaatttt tgaacatggc ttttcaactt taggtgatgt
gagaaatttc tttgaacaca ttctctccac taattttggt agaagctatt ttatttccac
ttcagaaaca cccacagcag ctattcgctt ctttggtagc tggttacggg aatatgtacc
agagcacccc agaagggctt acttatatga aattcgtgcc gaccaacact tttacaatgc
ccgcgccact ggggagaact tgttagattt aatgcgtcaa agacaagtag tatttgactc
tggtgatcga gaaatggcac aaatgggaat tagagcttta cgcacttcct ttgcgtatca
acgtgaatgg tttaccgatg gtccaattgc agcagctaat gtccgtagtg ctttgactagt
agatgctgtt cccgttgaac ctggtcatgc tcaccacccg gctggtcgtg ttgtagagac
tactagaatt aatgaaccgg aaatgcacaa ccctcattat caagagctgc aaacccaagc
caatgatcaa ccatgattgc caacaccagg aatagctact cctgtacatt tatcaattcc
ccaagcagct tccgttgctg atgtttcgga aggtacttcc gcttcgctat cgtttgcgtg
ccctgattga agtccacctt ctagtaatgg tgaaaatccg ctagacaaat gcattgcgga
aaagattgat aactataacc tacaatcctt accacagtac gctagcagtg taaaggaact
ggaagataca ccagtatacc taaggggaat taaaacgcaa aaaaccttta tgttacaagc
agatccgcaa aataacaatg tcttttttggt cgaagtaaac cccaaacaaa agtccagctt
tccccaaacc atcttctttt gggatgttta tcaacgaatt tgtctcaagg atttaactgg
tgcacaaatc agtctttcgc ttactgcctt tactactcag tatgctggtc agctcaaagt
gcaccttagt gttagcgcgg ttaatgccgt gaaccaaaag tgaaaaatga caccgcaaga
cattgcaata actcagtttc gggtctcctc tgaactgtta ggtcaaactg aaaatggctt
gttctgaaat accaagagtg gtggttcaca acacgatttg tatgtatgtc ctttgaaaaa
tccacctagt gatttggaag aattacaaat aattgttgat gaatgtacta cccatgcgca
gtttgttact atgcgtgcag ctagcacctt ctttgttgat gttcagctag ctggtattg
aagggggttat tactataccc cacaattaag tggttga**tct tatcagatga aaacaccaga
tggacagata ttctatgatc taaaaacttc gaaaatcttc tttgtccagg acaaccaaaa
cgtgttcttt ctccataata aactcaacaa acaaactggt tacagctggg attgagtaga
atggctaaaa catgacatga atgaggacaa agacgaaaac tttaaatggt acttttcgcg
tgatgacctt accattcctt ccgttgaagg gcttaacttc cgccacattc gctgttacgc
tgacaaccag cagttaaagg tgatcataag cggttcacgt tggggcggtt ggtactccac
ttacgataaa gttgaaagta atgtcgaaga taagattttg gtcaaagatg gttttgatcg
ctttttagcga ttaagcttta acgtcactgt tttgctctaa tgttagaagc aaagatcttg
```

-continued

S1 Nucleotide sequence with each tga changed to tgg for expression
in *E. coli*

(SEQ ID NO: 8)

```
atgccaaatc ctgttagatt tgtttaccgt gttgatttga gaagccctga agaaattttt   60
gaacatggct tttcaacttt aggtgatgtg agaaatttct tgaacacat tccctccact   120
aattttggta gaagctattt tatttccact tcagaaacac ccacagcagc tattcgcttc   180
tttggtagct ggttacggga atatgtacca gagcacccca gaagggctta cttatatgaa   240
attcgtgccg accaacactt ttacaatgcc cgcgccactg gggagaactt gttagattta   300
atgcgtcaaa gacaagtagt atttgactct ggtgatcgag aaatggcaca aatgggaatt   360
agagctttac gcacttcctt tgcgtatcaa cgtgaatggt ttaccgatgg tccaattgca   420
gcagctaatg tccgtagtgc ttggctagta gatgctgttc ccgttgaacc tggtcatgct   480
caccacccgg ctggtcgtgt tgtagagact actagaatta atgaaccgga atgcacaac    540
cctcattatc aagagctgca aacccaagcc aatgatcaac catggttgcc aacaccagga   600
atagctactc ctgtacattt atcaattccc caagcagctt ccgttgctga tgtttcggaa    660
ggtacttccg cttcgctatc gtttgcgtgc cctgattgga gtccaccttc tagtaatggt   720
gaaaatccgc tagacaaatg cattgcggaa agattgata actataacct acaatcctta   780
ccacagtacg ctagcagtgt aaaggaactg gaagatacac cagtatacct aaggggaatt   840
aaaacgcaaa aaacctttat gttacaagca gatccgcaaa ataacaatgt cttttggtc    900
gaagtaaacc ccaaacaaaa gcccagcttt ccccaaacca tcttcttttg ggatgtttat   960
caacgaattt gtctcaagga tttaactggt gcacaaatca gtctttcgct tactgccttt  1020
actactcagt atgctggtca gctcaaagtg caccttagtg ttagcgcggt taatgccgtg  1080
aaccaaaagt ggaaaatgac accgcaagac agtgcaataa ctcagtttcg ggtctcctct  1140
gaactgttag gtcaaactga aaatggcttg tcctggaata ccaagagtgg tggttcacaa  1200
cacgatttgt atgtatgtcc tttgaaaaat ccacctagtg atttggaaga attacaaata  1260
attgttgatg aatgtactac ccatgcgcag tttgttacta tgcgtgcagc tagcaccttc  1320
tttgttgatg ttcagctagg ctggtattgg aggggttatt actataccc acaattaagt  1380
ggttggtctt atcagatgaa aacaccagat ggacagatat tctatgatct aaaaacttcg  1440
aaaatcttct ttgtccagga caaccaaaac gtgttctttc tccataataa actcaacaaa  1500
caaactggtt acagctggga ttgggtagaa tggctaaaac atgacatgaa tgaggacaaa  1560
gacgaaaact ttaaatggta cttttcgcgt gatgacctta ccattccttc cgttgaaggg  1620
cttaacttcc gccacattcg ctgttacgct gacaaccagc agttaaaggt gatcataagc  1680
ggttcacgtt ggggcggttg gtactccact tacgataaag ttgaaagtaa tgtcgaagat  1740
aagatttttgg tcaaagatgg ttttgatcgc ttt                               1773
```

L2 nucleotide sequence with each tga changed to tgg for expression in
*E. coli*

(SEQ ID NO: 9)

```
atgccaaatc ctgttagatt tgtttaccgt gttgatttga gaagccctga agaaattttt   60
gaacatggct tttcaacttt aggtgatgtg agaaatttct tgaacacat tctctccact   120
aattttggta gaagctattt tatttccact tcagaaacac ccacagcagc tattcgcttc   180
tttggtagct ggttacggga atatgtacca gagcacccca gaagggctta cttatatgaa   240
attcgtgccg accaacactt ttacaatgcc cgcgccactg gggagaactt gttagattta   300
atgcgtcaaa gacaagtagt atttgactct ggtgatcgag aaatggcaca aatgggaatt   360
agagctttac gcacttcctt tgcgtatcaa cgtgaatggt ttaccgatgg tccaattgca   420
```

-continued

```
gcagctaatg tccgtagtgc ttggctagta gatgctgttc ccgttgaacc tggtcatgct   480
caccacccgg ctggtcgtgt tgtagagact actagaatta atgaaccgga atgcacaac    540 cctcattatc aagagctgca aacccaagcc aatgatcaac catggttgcc aacaccagga   600
atagctactc ctgtacattt atcaattccc caagcagctt ccgttgctga tgtttcggaa   660
ggtacttccg cttcgctatc gtttgcgtgc cctgattgga gtccaccttc tagtaatggt   720
gaaaatccgc taggcaaatg cattgcggaa aagattgata actataacct acaatcctta   780
ccacagtacg ctagcagtgt aaaggaactg gaagatacac cagtatacct aaggggaatt   840
aaaacgcaaa aaacctttat gttacaagca gatccgcaaa ataacaatgt cttttttggtc  900 gaagtaaacc ccaaacaaaa gtccagcttt ccccaaacca tcttcttttg ggatgtttat   960
caacgaattt gtctcaagga tttaactggt gcacaaatca gtctttcgct tactgccttt  1020
actactcagt atgctggtca gctcaaagtg caccttagtg ttagcgcggt taatgccgtg  1080
aaccaaaagt ggaaaatgac accgcaagac agtgcaataa ctcagtttcg ggtctcctct  1140
gaactgttag gtcaaactga aaatggcttg ttctggaata ccaagagtgg tggttcacaa  1200
cacgatttgt atgtatgtcc tttgaaaaat ccacctagtg atttggaaga attacaaata  1260
attgttgatg aatgtactac ccatgcgcag tttgttacta tgcgtgcagc tagcaccttc  1320
tttgttgatg ttcagctagg ctggtattgg aggggttatt actataccccc acaattaagt  1380 ggttggtctt atcagatgaa acaccagat ggacagatat tctatgatct aaaaacttcg   1440
aaaatcttct ttgtccagga caaccaaaac gtgttctttc tccataataa actcaacaaa  1500
caaactggtt acagctggga ttgggtagaa tggctaaaac atgacatgaa tgaggacaaa  1560
gacgaaaact ttaaatggta cttttcgcgt gatgacctta ccattccttc cgttgaaggg  1620
cttaacttcc gccacattcg ctgttacgct gacaaccagc agttaaaggt gatcataagc  1680
ggttcacgtt ggggcggttg gtactccact tacgataaag ttgaaagtaa tgtcgaagat  1740
aagattttgg tcaaagatgg ttttgatcgc ttt                                1773
```

JL nucleotide sequence with each tga changed to tgg for expression in *E. coli*

(SEQ ID NO: 10)

```
atgccaaatc ctgttagatt tgtttaccgt gttgatttga gaagccctga agaaattttt    60
gaacatggct tttcaacttt aggtgatgtg agaaatttct ttgaacacat tctctccact   120
aattttggta gaagctattt tatttccact tcagaaacac ccacagcagc tattcgcttc   180
tttggtagct ggttacggga atatgtacca gagcacccca aagggcttaa cttatatgaa   240
attcgtgccg accaacactt ttacaatgcc cgcgccactg gggagaactt gttagattta   300
atgcgtcaaa gacaagtagt atttgactct ggtgatcgag aaatggcaca aatgggaatt   360
agagctttac gcacttcctt tgcgtatcaa cgtgaatggt ttaccgatgg tccaattgca   420
gcagctaatg tccgtagtgc ttggctagta gatgctgttc ccgttgaacc tggtcatgct   480
caccacccgg ctggtcgtgt tgtagagact actagaatta atgaaccgga atgcacaac    540 cctcattatc aagagctgca aacccaagcc aatgatcaac catggttgcc aacaccagga   600
atagctactc ctgtacattt atcaattccc caagcagctt ccgttgctga tgtttcggaa   660
ggtacttccg cttcgctatc gtttgcgtgc cctgattgga gtccaccttc tagtaatggt   720
gaaaatccgc tagacaaatg cattgcggaa aagattgata actataacct acaatcctta   780
ccacagtacg ctagcagtgt aaaggaactg gaagatacac cagtatacct aaggggaatt   840
aaaacgcaaa aaacctttat gttacaagca gatccgcaaa ataacaatgt cttttttggtc  900 gaagtaaacc ccaaacaaaa gtccagcttt ccccaaacca tcttcttttg ggatgtttat   960
```

-continued

```
caacgaattt gtctcaagga tttaactggt gcacaaatca gtctttcgct tactgccttt 1020
actactcagt atgctggtca gctcaaagtg caccttagtg ttagcgcggt taatgccgtg 1080
aaccaaaagt ggaaaatgac accgcaagac agtgcaataa ctcagtttcg ggtctcctct 1140
gaactgttag gtcaaactga aaatggcttg ttctggaata ccaagagtgg tggttcacaa 1200
cacgatttgt atgtatgtcc tttgaaaaat ccacctagtg atttggaaga attacaaata 1260
attgttgatg aatgtactac ccatgcgcag tttgttacta tgcgtgcagc tagcaccttc 1320
tttgttgatg ttcagctagg ctggtattgg aggggttatt actataccc acaattaagt 1380 ggttggtctt atcagatgaa acaccagat ggacagatat tctatgatct aaaaacttcg 1440
aaaatcttct tgtccagga caaccaaaac gtgttctttc tccataataa actcaacaaa 1500
caaactggtt acagctggga ttgggtagaa tggctaaaac atgacatgaa tgaggacaaa 1560
gacgaaaact ttaaatggta cttttcgcgt gatgaccta ccattccttc cgttgaaggg 1620
cttaacttcc gccacattcg ctgttacgct gacaaccagc agttaaaggt gatcataagc 1680
ggttcacgtt ggggcggttg gtactccact tacgataaag ttgaaagtaa tgtcgaagat 1740
aagattttgg tcaaagatgg ttttgatcgc ttt                                1773
```

RJL1 nucleotide sequence with each tga changed to tgg for expression in
E. coli

```
                                                         (SEQ ID NO: 11)
atgccaaatc ctgttagatt tgtttaccgt gttgatttga aagccctga agaaattttt   60 gaacatggct tttcaacttt aggtgatgtg agaaatttct ttgaacacat tctctccact  120
aattttggta gaagctattt tatttccact tcagaaacac ccacagcagc tattcgcttc  180
tttggtagct ggttacggga atatgtacca gagcacccca gaagggctta cttatatgaa  240
attcgtgccg accaacactt ttacaatgcc cgcgccactg gggagaactt gttagattta  300
atgcgtcaaa gacaagtagt atttgactct ggtgatcgag aaatggcaca atgggaatt   360 agagctttac gcacttcctt tgcgtatcaa cgtgaatggt ttaccgatgg tccaattgca  420
gcagctaatg tccgtagtgc ttggctagta gatgctgttc ccgttgaacc tggtcatgct  480
caccacccgg ctggtcgtgt tgtagagact actagaatta atgaaccgga atgcacaac   540 cctcattatc aagagctgca aacccaagcc aatgatcaac catggttgcc aacaccagga  600
atagctactc ctgtacattt atcaattccc caagcagctt ccgttgctga tgtttcggaa  660
ggtacttccg cttcgctatc gtttgcgtgc cctgattgga gtccaccttc tagtaatggt  720
gaaaatccgc tagacaaatg cattgcggaa aagattgata actataacct acaatcctta  780
ccacagtacg ctagcagtgt aaaggaactg gaagatacac cagtatacct aaggggaatt  840
aaaacgcaaa aaacctttat gttacaagca gatccgcaaa ataacaatgt ctttttggtc  900
gaagtaaacc ccaaacaaaa gtccagcttt ccccaaacca tcttcttttg ggatgtttat  960
caacgaattt gtctcaagga tttaactggt gcacaaatca gtctttcgct tactgccttt 1020
actactcagt atgctggtca gctcaaagtg caccttagtg ttagcgcggt taatgccgtg 1080
aaccaaaagt ggaaaatgac accgcaagac agtgcaataa ctcagtttcg ggtctcctct 1140
gaactgttag gtcaaactga aaatggcttg ttctcggaata ccaagagtgg tggttcacaa 1200
cacgatttgt atgtatgtcc tttgaaaaat ccacctagtg atttggaaga attacaaata 1260
attgttgatg aatgtactac ccatgcgcag tttgttacta tgcgtgcagc tagcaccttc 1320
tttgttgatg ttcagctagg ctggtattgg aggggttatt actataccc acaattaagt 1380 ggttggtctt atcagatgaa acaccagat ggacagatat tctatgatct aaaaacttcg 1440
aaaatcttct tgtccagga caaccaaaac gtgttctttc tccataataa actcaacaaa 1500
```

-continued

```
caaactggtt acagctggga ttgggtagaa tggctaaaac atgacatgaa tgaggacaaa 1560
gacgaaaact ttaaatggta cttttcgcgt gatgacctta ccattccttc cgttgaaggg 1620
cttaacttcc gccacattcg ctgttacgct gacaaccagc agttaaaggt gatcataagc 1680
ggttcacgtt ggggcggttg gtactccact tacgataaag ttgaaagtaa tgtcgaagat 1740
aagattttgg tcaaagatgg ttttgatcgc ttt                              1773
```

BRIEF DESCRIPTION OF THE DRAWINGS

FIG. 5 shows binding of CARDS toxin (CmC-CARDS) to HeLa cells in the presence of rabbit polyclonal antibodies reactive against full length and peptide truncations of CARDS toxin. CmC-CARDS was incubated with specific antibodies for 10 minutes at room temperature, added to HeLa cells for incubation at 4° C. for 30 minutes, washed with PBS three times to remove unbound toxin before mCherry fluorescence measurements. Values show the percentage of CARDS toxin binding in triplicate wells±S.D.

FIG. 8 shows epitope mapping of anti-CARDS TX monoclonal antibodies. Reactivity of D2 and D3 monoclonal antibodies with various truncated and synthetic recombinant CARDS toxin proteins and synthetic peptides was analyzed by western blotting and ELISA, which shows the aa249-264 and aa420-438 epitope targets for D2 and D3, respectively.

SUMMARY OF THE INVENTION

Figure 1:
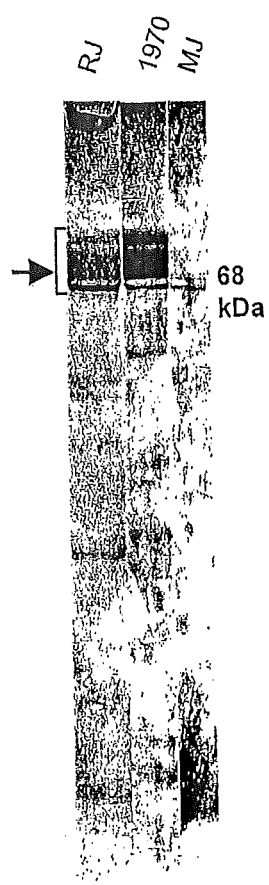
FIG. 1 shows an immunoblot that demonstrates both production of the CARDS toxin and anti-CARDS antibodies in three patients during infection with *Mycoplasma pneumoniae*.

The present invention provides *Mycoplasma pneumoniae* exotoxin (CARDS toxin) from subjects infected with *Mycoplasma pneumoniae*. In particular, the present invention provides a polypeptide comprising, consisting essentially of, and/or consisting of the amino acid sequence of SEQ ID NO:2 (S1 isolate), a polypeptide comprising, consisting essentially of, and/or consisting of the amino acid sequence of SEQ ID NO:3 (JL isolate), a polypeptide comprising, consisting essentially of, and/or consisting of the amino acid sequence of SEQ ID NO:4 (RJL1 isolate), a polypeptide comprising, consisting essentially of, and/or consisting of the amino acid sequence of SEQ ID NO:5 (L2 isolate), a polypeptide comprising, consisting essentially of, and/or consisting of the amino acid sequence of SEQ ID NO:1 (reference sequence), and/or a polypeptide comprising, consisting essentially of, and/or consisting of the amino acid sequence of SEQ ID NO:6 (composite sequence), either individually or in any combination.

The present invention further provides biologically active fragments of the polypeptides of this invention, as well as antibodies that specifically bind the polypeptides and/or fragments of the polypeptides of this invention.

Further provided are nucleotide sequences that encode the polypeptides and fragments of this invention. In particular, the present invention provides an isolated nucleic acid comprising, consisting essentially of, and/or consisting of the nucleotide sequence of SEQ ID NO:8 (S1 isolate), an isolated nucleic acid comprising, consisting essentially of, and/or consisting of the nucleotide sequence of SEQ ID NO:10 (JL isolate), an isolated nucleic acid comprising, consisting essentially of, and/or consisting of the nucleotide sequence of SEQ ID NO:11 (RJL1 isolate), an isolated nucleic acid comprising, consisting essentially of, and/or consisting of the nucleotides sequence of SEQ ID NO:9 (L2 isolate), an isolated nucleic acid comprising, consisting essentially of, and/or consisting of the nucleotides sequence of SEQ ID NO:7 (reference sequence), and/or an isolated nucleic acid comprising, consisting essentially of, and/or consisting of the nucleotide sequence of SEQ ID NO:76 (composite sequence), either individually or in any combination.

Additionally provided is a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:2 (S1 isolate), a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:3 (JL isolate), a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:4 (RJL1 isolate), a nucleic acid comprising, consisting essentially of, and/or consisting of a nucleotide sequence that encodes an amino acid comprising, consisting essentially of, and/or consisting of the amino acid sequence or a biologically active fragment of an amino acid sequence of SEQ ID NO:5 (L2) isolate, a nucleic acid comprising, consisting essentially of, and/or consisting of a nucleotide sequence that encodes an amino acid comprising, consisting essentially of, and/or consisting of the amino acid sequence or a biologically active fragment of an amino acid sequence of SEQ ID NO:1 (reference sequence) isolate, and/or a nucleic acid comprising, consisting essentially of, and/or consisting of a nucleotide sequence encoding an amino acid sequence comprising, consisting essentially of, and/or consisting of the amino acid sequence or a biologically active fragment of the amino acid sequence of SEQ ID NO:6 (composite sequence). Further provided herein is a nucleic acid that is the complement of each and any of the nucleic acids of this invention.

Also provided herein are probes and primers for the detection and/or amplification of the nucleic acids of this invention, including TTTTTACATATGCCAAATCCTGTT (SEQ ID NO:12; Primer 1), CGTTAAAGGATCCTCGCTAAAAGC-GATC (SEQ ID NO:13; Primer 2), CTAGCCAAGCAC-TACGGACATTAGC (SEQ ID NO:14; (Primer 3), CGTAGT-GCTTGGCTAGTAGATGCTGTT (SEQ ID NO:15; (Primer 4), CCTGGTGTTGGCAACCATGGTTG (SEQ ID NO:16; (Primer 5), GATCAACCATGGTTGCCAACACC (SEQ ID NO:17; (Primer 6), AAGGTGGACTCCAATCAGGGCACG (SEQ ID NO:18; (Primer 7), CGTGCCCTGATTGGAGTC-CACCTT (SEQ ID NO:19; (Primer 8), GCGGTGT-CATTTTCCACTTTTGG (SEQ ID NO:20; (Primer 9), CCAAAAGTGGAAAATGACACCGC (SEQ ID NO:21; (Primer 10), GGTATTCCAGAACAAGCCATTT (SEQ ID NO:22; (Primer 11), GCTTGTTCTGGAATACCAA-GAGTG (SEQ ID NO:23; (Primer 12), ATAACCCCTATAC-CAGCCTAG (SEQ ID NO:24; (Primer 13), GCTGGTATTG-GAGGGGTTATTACTATACCCCACAATTAAGTGGTTG GTCTTA TCAGATG (SEQ ID NO:25; (Primer 14), CCAT-TCTACCCAATCCCAGCTGTA (SEQ ID NO:26; (Primer 15), and TACAGCTGGGATTGGGTAGAATGG (SEQ ID NO:27; (Primer 16).

Additionally provided in this invention are methods of diagnosing infection by M. pneunomoniae in a subject comprising contacting a biological sample from the subject with a polypeptide or antibody of this invention under conditions whereby an antigen/antibody complex can form; and detecting formation of an antigen/antibody complex, thereby diagnosing infection by M. pneumoniae in the subject.

Methods are also provided herein for diagnosing infection by M. pneumoniae in a subject comprising contacting a biological sample from the subject with a nucleic acid of this invention under conditions whereby hybridization of nucleic acid molecules can occur; and detecting hybridization, thereby diagnosing infection by M. pneumoniae in the subject.

Furthermore, the present invention provides methods of eliciting an immune response in a subject, comprising administering to the subject an effective amount of a polypeptide and/or biologically active fragment of a polypeptide of this invention and/or by administering to a subject an effective amount of a nucleic acid comprising a nucleotide sequence encoding a polypeptide and/or biologically active fragment of a polypeptide of this invention.

The present invention additionally provides methods of providing passive immunity to a subject, comprising administering to the subject an effective amount of an antibody of this invention.

In further embodiments, the present invention provides methods of treating and/or preventing infection by M. pneumoniae in a subject, comprising administering to the subject an effective amount of a polypeptide of this invention and/or an effective amount of a biologically active fragment of a polypeptide of this invention and/or an effective amount of a nucleic acid comprising a nucleotide sequence encoding a polypeptide of this invention and/or an effective amount of a nucleic acid comprising a nucleotide sequence encoding a biologically active fragment of a polypeptide of this invention. Also provided are methods of treating and/or preventing infection by M. pneumoniae in a subject, comprising administering to the subject an effective amount of an antibody of this invention.

In yet further embodiments, the present invention provides methods of identifying substances having the ability to inhibit or enhance various activities of the polypeptides and/or biologically active fragments of this invention, including but not limited to, binding activity, translocating activity, immunogenic activity, ADP-ribosylating activity and/or cytopathology inducing activity. These methods are carried out by contacting the polypeptides and/or biologically active fragments of this invention and/or the nucleic acids of this invention, with the substance to be tested for inhibitory or enhancing activity, under conditions whereby the inhibition or enhancement of activity can be detected, as described herein.

In further aspects of this invention, provided herein is a monoclonal antibody or fragment thereof that specifically binds an epitope within amino acids 249-272 of *Mycoplasma pneumoniae* exotoxin (CARDS toxin).

Also provided herein is a monoclonal antibody or fragment thereof that specifically binds an epitope within amino acids 421-438 of *Mycoplasma pneumoniae* exotoxin (CARDS toxin).

The present invention additionally provides a method of treating and/or preventing a disorder caused by infection of a subject with *Mycoplasma pneumoniae*, comprising administering to the subject an effective amount of a monoclonal antibody or fragment thereof as described herein.

Further provided herein is a method of providing passive immunity to a subject comprising administering to the subject an effective amount of a monoclonal antibody or fragment thereof as described herein.

In yet further aspects of this invention, provided herein is an isolated peptide comprising, consisting essentially of or consisting of the amino acid sequence AEKIDNYNLQS-LPQYASSVKELED (aa 249-272 of the reference CARDS toxin sequence (SEQ ID NO:1)).

Furthermore, the present invention provides an isolated peptide comprising the amino acid sequence of IVDECT- THAQFVTMRAAS (aa 421-438 of the reference CARDS toxin sequence (SEQ ID NO:1)).

In addition, the present invention provides an isolated peptide being from at least about 17 amino acids in length to about 100 amino acids in length, wherein the peptide comprises one or more of the peptides listed in Table 1, in any combination.

The present invention further provides a method of eliciting an immune response in a subject, comprising administering to the subject an effective amount of a peptide of this invention as described herein.

The present invention also provides a method of diagnosing infection (e.g., acute infection) by Mycoplasma pneumoniae in a subject, comprising: a) contacting a biological sample obtained from the subject with a peptide of this invention, under conditions whereby an antigen/antibody complex can form; and b) detecting formation of an antigen/antibody complex, thereby diagnosing infection by Mycoplasma pneumoniae in the subject.

In further embodiments, the present invention provides a kit comprising one or more peptides and/or antibodies of this invention and optionally, reagents for detecting an antigen/antibody complex.

Various other objectives and advantages of the present invention will become apparent from the following detailed description.

DETAILED DESCRIPTION OF THE INVENTION

As used herein, "a," "an" or "the" can mean one or more than one. For example, "a" cell can mean a single cell or a multiplicity of cells.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in angiogenesis-stimulating activity of at least about 50% or more as compared to the activity of a polypeptide consisting of the recited sequence.

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

The present invention is based on the discovery of polypeptides of Mycoplasma pneumoniae having the respective amino acid sequence described herein and encoded by the nucleic acids described herein and the identification of activities of these polypeptides and various fragments or "domains" of these polypeptides. Characterization of these polypeptides and fragments indicates that the newly identified protein is an exotoxin of Mycoplasma pneumoniae and it is referred to herein as community acquired respiratory distress syndrome (CARDS) toxin. Thus, the present invention provides an isolated polypeptide comprising, consisting essentially of, and/or consisting of the amino acid sequence of SEQ ID NO:2 (S1 isolate), an isolated polypeptide comprising, consisting essentially of, and/or consisting of the amino acid sequence of SEQ ID NO:3 (JL isolate), an isolated polypeptide comprising, consisting essentially of, and/or consisting of the amino acid sequence of SEQ ID NO:4 (RJL1 isolate), an isolated polypeptide comprising, consisting essentially of, and/or consisting of the amino acid sequence of SEQ ID NO:5 (L2 isolate), an isolated polypeptide comprising, consisting essentially of, and/or consisting of the amino acid sequence of SEQ ID NO:1 (reference sequence), and/or an isolated polypeptide comprising, consisting essentially of, and/or consisting of the amino acid sequence of SEQ ID NO:6 (composite sequence), either individually or in any combination.

The present invention further provides biologically active fragments of the polypeptides of this invention, as well as antibodies that specifically bind the polypeptides and/or fragments of the polypeptides of this invention. In addition, the present invention provides a monoclonal antibody or fragment thereof that specifically binds an epitope within amino acids 249-272 of Mycoplasma pneumoniae exotoxin. Thus, the monoclonal antibody can specifically bind an epitope that is made up of (e.g., includes) amino acids 249, 250, 251, 252, 253, 254, 255, 256, 257, 258, 259, 260, 261, 262, 263, 264, 265, 266, 267, 268, 270, 271 and/or 272, in any combination (amino acid numbering based on amino acid sequence of SEQ ID NO:1)

In some embodiments, the monoclonal antibody can be a monoclonal antibody produced by hybridoma cell line designated M713A9 and in some embodiments, the monoclonal antibody can be a monoclonal antibody or fragment thereof that competes for binding to the same epitope specifically bound by the monoclonal antibody produced by the hybridoma cell designated M713A9.

In certain embodiments, the monoclonal antibody or a fragment thereof is a chimeric antibody or a humanized antibody. In additional embodiments, the chimeric or humanized antibody comprises at least a portion of the complementarity determining regions (CDRs) of the monoclonal antibody produced by hybridoma cell line designated M713A9. As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof.

Additional embodiments of this invention include a monoclonal antibody or fragment thereof that specifically binds an epitope within amino acids 421-438 of Mycoplasma pneumoniae exotoxin. Thus, the monoclonal antibody can specifically bind an epitope that is made up of (e.g., includes) amino acids 421, 422, 423, 424, 425, 426, 427, 428, 429, 430, 431, 432, 433, 434, 435, 436, 437 And/or 438, in any combination (amino acid numbering based on amino acid sequence of SEQ ID NO:1.

In some embodiments, the monoclonal antibody can be a monoclonal antibody produced by hybridoma cell line designated M108A8 and in some embodiments, the monoclonal antibody can be a monoclonal antibody or fragment thereof that competes for binding to the same epitope specifically bound by the monoclonal antibody produced by the hybridoma cell designated M108A8.

In certain embodiments, the monoclonal antibody or a fragment thereof is a chimeric antibody or a humanized antibody. In additional embodiments, the chimeric or humanized antibody comprises at least a portion of the complementarity determining regions (CDRs) of the monoclonal antibody produced by hybridoma cell line designated M108A8. As used herein, a "portion" of a CDR is defined as one or more of the three loops from each of the light and heavy chain that make up the CDRs (e.g., from 1-6 of the CDRs) or one or more portions of a loop comprising, consisting essentially of or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof.

In further embodiments of this invention, also provided herein is a monoclonal antibody or fragment thereof that specifically binds an epitope within the amino acid sequence of any of the peptides listed in Table 1. Such antibodies can be humanized and/or chimeric. Such antibodies can be employed in the methods described herein to treat and/or prevent a disorder caused by infection of a subject by *Mycoplasma pneumoniae*. Such antibodies can also be used in the methods described herein to detect and/diagnose *Mycoplasma pneumoniae* infection.

A monoclonal antibody or fragment thereof as described above can be coupled to a detectable group and/or a therapeutic group, as is known in the art. In some embodiments, the monoclonal antibody or fragment thereof as described above can be a humanized antibody or fragment thereof and in some embodiments, the monoclonal antibody or fragment thereof as described above can be a chimeric antibody or fragment thereof. In some embodiments, the antibody or fragment thereof of this invention can be in a pharmaceutical formulation or pharmaceutical composition comprising a pharmaceutically acceptable carrier.

The present invention also provides a method of treating and/or preventing a disorder caused by infection of a subject with *Mycoplasma pneumoniae*, comprising administering to the subject an effective amount of the antibody or fragment thereof of this invention. Nonlimiting examples of disorders related to *Mycoplasma pneumoniae* infection include acute and chronic airway diseases such as tracheobronchitis, pharyngitis, pneumonia, acute respiratory distress syndrome, chronic obstructive pulmonary disease; lung cancers caused by persistence of *M. pneumoniae* and CARDS toxin-mediated chronic inflammation; and extrapulmonary diseases such as cardiovascular, neurologic, dermatologic, gastrointestinal, joint, and hematologic inflammation and associated pathologies.

Also provided herein is a method of providing passive immunity to a subject comprising administering to the subject an effective amount of an antibody or fragment thereof of this invention. The antibodies of this invention can be administered to a subject, for example, subcutaneously, intravenously, intranasally, intramuscularly, via intra-airway spray inhalation, and any combination thereof.

In further embodiments, the present invention provides an isolated peptide comprising, consisting essentially of or consisting of the amino acid sequence AEKIDNYNLQSLPQ-YASSVKELED (aa 249-272 of the amino acid sequence of CARDS toxin as exemplified by the amino acid sequence of SEQ ID NO:1).

The present invention further provides an isolated peptide comprising, consisting essentially of or consisting of the amino acid sequence of IVDECTTHAQFVTMRAAS (aa 421-438 of the amino acid sequence of CARDS toxin as exemplified by the amino acid sequence of SEQ ID NO:1).

In sonic embodiments, the present invention provides an isolated peptide that is at least about 10 amino acids in length to at least about 100 amino acids in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, etc., wherein the peptide comprises at least 10, 11, 12, 13, 14, 15, 16, 17, or 18 contiguous amino acids of one or more (e.g., 2, 3, 4, 5, 6, 7, 8, 9, 10, etc.) of the peptides listed in Table 1, in any combination.

A peptide of this invention can be present in a composition comprising a pharmaceutically acceptable carrier. A peptide of this invention can also be present in a kit, along with reagents for diagnosing infection by *Mycoplasma pneumoniae* in a subject, such as reagents for detecting antigen/antibody complex formation as are well known in the art.

The present invention also provides an isolated nucleic acid molecule comprising a nucleotide sequence encoding a peptide of this invention. The nucleic acid molecule can be present in a cell and/or in a vector. A vector of this invention can be present in a cell.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic kid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Felgner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931), It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell, A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass both peptides and proteins, unless indicated otherwise.

It will be understood that the polypeptides and peptides specifically disclosed herein will typically tolerate substitutions in the amino acid sequence and substantially retain biological activity. To identify polypeptides and peptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to Table In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id), these are: isoleucine (+4.5); valine (+4.2); leucine (+3.8); phenylalanine (+2.8); cysteine/cystine (+2.5); methionine (+1,9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., angiogenic activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and angiogenic activity can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

Additional aspects of the present invention include a method of eliciting an immune response in a subject, comprising administering to the subject an effective amount of a peptide of this invention.

The present invention also provides a method of treating and/or preventing a disorder caused by infection in a subject with *Mycoplasma pneumoniae*, comprising administering to the subject an effective amount of a peptide of this invention.

Additionally provided herein is a method of diagnosing infection by *Mycoplasma pneumoniae* in a subject, comprising: a) contacting a biological sample obtained from the subject with a peptide of this invention under conditions whereby an antigen/antibody complex can form; and b) detecting formation of an antigen/antibody complex, thereby diagnosing infection by *Mycoplasma pneumoniae* in the subject. In some embodiments, the infection can be an acute infection and in some embodiments, the infection can be chronic infection.

The present invention further provides a method of identifying either a good (e.g., favorable) or poor (e.g., unfavorable) prognostic outcome for a subject infected with *Mycoplasma pneumoniae*, comprising: a) contacting a biological sample from the subject with a peptide of this invention under conditions whereby an antigen/antibody complex can form; and b) detecting formation of an antigen/antibody complex, wherein the presence of an antigen/antibody complex (i.e., detection of an antigen/antibody complex) identifies a good prognostic outcome for the subject and the absence of an antigen/antibody complex (i.e., failure to detect formation of an antigen/antibody complex) identifies a poor prognostic outcome for the subject.

Further provided are nucleotide sequences that encode the polypeptides and fragments of this invention. In particular, the present invention provides an isolated nucleic acid comprising, consisting essentially of, and/or consisting of the nucleotide sequence of SEQ ID NO:8 (S1 isolate), an isolated nucleic acid comprising, consisting essentially of, and/or consisting of the nucleotide sequence of SEQ ID NO:10 (JL isolate), an isolated nucleic acid comprising, consisting essentially of, and/or consisting of the nucleotide sequence of SEQ ID NO:11 (RJL1 isolate), an isolated nucleic acid comprising, consisting essentially of, and/or consisting of the nucleotides sequence of SEQ ID NO:9 (L2 isolate), an isolated nucleic acid comprising, consisting essentially of, and/or consisting of the nucleotides sequence of SEQ ID NO:7 (reference sequence), and/or an isolated nucleic acid comprising, consisting essentially of, and/or consisting of the nucleotide sequence of SEQ ID NO:76 (composite sequence), either individually or in any combination.

Additionally provided is a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:2 (S1 isolate), a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:3 (JL isolate), a nucleic acid comprising, consisting essentially of, and/or consisting of a nucleotide sequence that encodes an amino acid sequence comprising, consisting essentially of, and/or consisting of the amino acid sequence or a biologically active fragment of the amino acid sequence of SEQ ID NO:4 (RJL1 isolate), a nucleic acid comprising, consisting essentially of, and/or consisting of a nucleotides sequence that encodes an amino acid comprising, consisting essentially of, and/or consisting of the amino acid sequence or a biologically active fragment of an amino acid sequence of SEQ ID NO:5 (L2 isolate), and/or a nucleic acid comprising, consisting essentially of, a nucleic acid comprising, consisting essentially of, and/or consisting of a nucleotides sequence that encodes an amino acid comprising, consisting essentially of, and/or consisting of the amino acid sequence or a biologically active fragment of an amino acid sequence of SEQ ID NO:1 (reference sequence), and/or a nucleic acid comprising, consisting essentially of, and/or consisting of a nucleotide sequence encoding an amino acid sequence comprising, consisting essentially of, and/or consisting of the amino acid sequence or a biologically active fragment of the amino acid sequence of SEQ ID NO:6 (composite sequence). Further provided herein is a nucleic acid that is the complement of each and any of the nucleic acids of this invention.

Also provided herein are probes and primers for the detection of the nucleic acids of this invention, including TTTT-TACATATGCCAAATCCTGTT (SEQ ID NO:12; Primer 1), CGTTAAAGGATCCTCGCTAAAAGCGATC (SEQ ID NO:13; Primer 2), CTAGCCAAGCACTACGGACATTAGC (SEQ ID NO:14; Primer 3), CGTAGTGCTTGGCTAGTA-GATGCTGTT (SEQ ID NO:15; (Primer 4), CCTGGTGT-TGGCAACCATGGTTG (SEQ ID NO:16; (Primer 5), GAT-CAACCATGGTTGCCAACACC (SEQ ID NO:17; (Primer 6), AAGGTGGACTCCAATCAGGGCACG (SEQ ID NO:18; (Primer 7), CGTGCCCTGATTGGAGTCCACCTT (SEQ ID NO:19; (Primer 8), GCGGTGTCATTTTC-CACTTTTGG (SEQ ID NO:20; (Primer 9), CCAAAAGTG-GAAAATGACACCGC (SEQ ID NO:21; (Primer 10), GGTATTCCAGAACAAGCCATTT (SEQ ID NO:22; (Primer 11), GCTTGTTCTGGAATACCAAGAGTG (SEQ ID NO:23; (Primer 12), ATAACCCCTATACCAGCCTAG (SEQ ID NO:24; (Primer 13), GCTGGTATTGGAGGGGT-TATTACTATACCCCACAATTAAGTGGTTGGTCTTA TCAGATG (SEQ ID NO:25; (Primer 14), CCATTCTAC-CCAATCCCAGCTGTA (SEQ ID NO:26; (Primer 15), and TACAGCTGGGATTGGGTAGAATGG (SEQ ID NO:27; (Primer 16), alone and/or in any combination. The present invention further provides as additional embodiments without limitation, other oligonucleotides listed in this application and in the Sequence Listing attached hereto.

"Isolated" as used herein means the nucleic acid or polypeptide or peptide or cell of this invention is sufficiently free of contaminants or cell components with which nucleic acids or polypeptides or peptides or cells normally occur, "Isolated" does not mean that the preparation is technically pure (homogeneous), but it is sufficiently pure to provide the nucleic acid or polypeptide or peptide or cell in a form in which it can be used therapeutically.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

"Epitope" or "antigenic epitope" or "antigenic peptide" as used herein means a specific amino acid sequence of limited length which, when present in the proper conformation, provides a reactive site for an antibody or T cell receptor. The identification of epitopes on antigens can be carried out by immunology protocols that are well known in the art. In some embodiments, an epitope of this invention can be a set of amino acid residues that is involved in recognition by a particular immunoglobulin. In the context of T cells, an epitope is defined as the set of amino acid residues necessary for recognition by T cell receptor proteins and/or MHC receptors. In an immune system setting, in vivo or in vitro, an epitope refers to the collective features of a molecule, such as primary, secondary and/or tertiary peptide structure, and/or charge, that together form a site recognized by an immunoglobulin, T cell receptor and/or HLA molecule. In the case of a B-cell (antibody) epitope, it is typically a minimum of about 3-4 amino acids, in some embodiments at least about 5 amino acids, ranging up to about 50 amino acids. In some embodiments, the humoral response-inducing epitopes can be between 5 and 30 amino acids, usually between 12 and 25 amino acids, and commonly between 15 and 20 amino acids. In the case of a T-cell epitope, an epitope can include at least about 7-9 amino acids, and for a helper T-cell epitope, at least about 12-20 amino acids. Typically, such a T-cell epitope can include between about 7 and about 15 amino acids, e.g., 7, 8, 9, 10, 11, 12, 13, 14 or 15 amino acids.

As used herein, the term "polypeptide" or "protein" is used to describe a chain of amino acids that correspond to those encoded by a nucleic acid. A polypeptide of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences disclosed herein are presented in the amino to carboxy direction, from left to right. Nucleotide sequences are presented herein by single strand only, in the 5' to 3' direction, from left to right. However, it is intended that the nucleic acids of this invention can be either single or double stranded (i.e., including the complementary nucleic acid). A nucleic acid of this invention can be the complement of a nucleic acid described herein.

A "biologically active fragment" includes a polypeptide of this invention that comprises a sufficient number of amino acids to have one or more of the biological activities of the polypeptides of this invention. Such biological activities can include, but are not limited to, in any combination, binding activity, translocating activity, immunogenic activity, ADP-ribosylating activity, and/or cytopathology inducing activity, as well as any other activity now known or later identified for the polypeptides and/or fragments of this invention. A fragment of a polypeptide of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

Fragments of the polypeptides of this invention are preferably at least about ten amino acids in length and retain one or more of the biological activities and/or the immunological activities of the CARDS toxin. Examples of the fragments of this invention include, but are not intended to be limited to, the following fragments identified by the amino acid number as shown in the Sequence Listing for each of the isolates of SEQ ID NO:2 (S1 isolate), SEQ ID NO:3 (JL isolate), SEQ ID NO:4 (RJL1 isolate), SEQ ID NO:5 (L2 isolate), SEQ ID NO:6 (composite sequence) and SEQ ID NO:1 (reference sequence): Amino acids 1-10, 10-20, 20-30, 30-40, 40-50, 50-60, 60-70, 70-80, 80-90, 90-100, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500, 500-510, 510-520, 520-530, 530-540, 540-550, 550-560, 560-570, 570-580, 580-591, 1-25, 1-50, 1-67, 1-75, 1-100, 1-125, 1-135, 1-145, 1-150, 1-160, 1-170, 1-180, 1-190, 1-200, 1-250, 1-300, 1-350, 1-400, 1-450, 1-500, 68-180, 183-123, 500-591, 450-591, 400-591, 350-591, 300-591, 250-591, 200-591, 150-591, 100-591, 50-591, 50-100, 100-200, 200-300, 300-400, 400-500, 500-591, 550-591.

It is understood that this list is exemplary only and that a fragment of this invention can be any amino acid sequence containing any combination of contiguous amino acids that are numbered in the Sequence Listing as amino acids 1 through 591 even if that combination is not specifically recited as an example herein. It is also understood that these fragments can be combined in any order or amount. For example, fragment 1-10 can be combined with fragment 10-20 to produce a fragment of amino acids 1-20. Also fragments can be present in multiple numbers and in any combination in a fragment of this invention. Thus, for example, fragment 1-150 can be combined with a second fragment 1-150 and/or combined with fragment 400-500 to produce a fragment of this invention. Other exemplary fragments of this invention include the domains of the CARDS toxin described herein [e.g., domain 1 (N terminal 249 amino acids), domain 2 (256 amino acids) and domain 3 (247 amino acids at carboxy terminus)].

The term "homology" as used herein refers to a degree of similarity between two or more sequences. There may be partial homology or complete homology (i.e., identity). A partially complementary sequence that at least partially inhibits an identical sequence from hybridizing to a target nucleic acid is referred to as "substantially homologous." The inhibition of hybridization of the completely complementary sequence to the target sequence can be examined using a hybridization assay (Southern or Northern blot, solution hybridization and the like) under conditions of low stringency. A substantially homologous sequence or hybridization probe will compete for and inhibit the binding of a completely homologous sequence to the target sequence under conditions of low stringency, as this term is known in the art. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

The term "hybridization" as used herein refers to any process by which a first strand of nucleic acid binds with a second strand of nucleic acid through base pairing. Nucleic acids encoding the polypeptides and/or fragments of this invention can be detected by DNA-DNA or DNA-RNA hybridization or amplification using probes, primers and/or fragments of polynucleotides encoding the polypeptides and/or fragments of this invention and/or designed to detect and/or amplify the nucleic acids of this invention.

The term "hybridization complex" as used herein refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells and/or nucleic acids have been fixed).

The term "nucleotide sequence" refers to a heteropolymer of nucleotides or the sequence of these nucleotides. The terms "nucleic acid," "oligonucleotide" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. Nucleic acids of this invention can comprise a nucleotide sequence that can be identical in sequence to the sequence which is naturally occurring or, due to the well-characterized degeneracy of the nucleic acid code, can include alternative codons which encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained.

The term "probe" or "primer" includes naturally occurring or recombinant or chemically synthesized single- and/or double-stranded nucleic acids. They can be labeled for detection by nick translation, Klenow fill-in reaction, PCR or other methods well known in the art. Probes and primers of the present invention, their preparation and/or labeling are described in Sambrook et al. 1989. *Molecular Cloning: A Laboratory Manual*, Cold Spring Harbor Laboratory, NY and Ausubel et al. 1989. *Current Protocols in Molecular Biology*, John Wiley & Sons, New York N.Y., both of which are incorporated herein by reference in their entirety for these teachings.

The term "stringent" as used here refers to hybridization conditions that are commonly understood in the art to define the conditions of the hybridization procedure. Stringency conditions can be low, high or medium, as those terms are commonly know in the art and well recognized by one of ordinary skill. In various embodiments, stringent conditions can include, for example, highly stringent (i.e., high stringency) conditions (e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

"Amplification" as used herein includes the production of multiple copies of a nucleic acid molecule and is generally carried out using polymerase chain reaction (PCR) and/or other amplification technologies as are well known in the art (Dieffenbach and Dveksler. 1995. *PCR Primer, a Laboratory Manual*, Cold Spring Harbor Press, Plainview, N.Y.).

As used herein, the term "antibody" includes intact immunoglobin molecules as well as fragments thereof, such as Fab, F(ab')2, and Fc, which are capable of binding the epitopic determinant of an antigen (i.e., antigenic determinant). Antibodies that bind the polypeptides of this invention are prepared using intact polypeptides or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. Nos. 4,474,893 or 4,816,567. The antibodies can also be chemically constructed according to the method disclosed in U.S. Pat. No. 4,676,980. The antibody can further be a single chain antibody or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein, (1975) *Nature* 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

The term "sample" as used herein is used in its broadest sense. A biological sample suspected of containing a polypeptide, fragment, antibody and/or nucleic acid of this invention can be any biological fluid, an extract from a cell, an extracellular matrix isolated from a cell, a cell (in solution or bound to a solid support), a tissue, a tissue print, and the like. Such a sample or biological sample can be obtained from a subject of this invention according to well known methods.

"Effective amount" or "therapeutically effective amount" refers to an amount of a compound or composition of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation, (See, for example, Remington, *The Science And Practice of Pharmacy* (20th ed. 2000)), A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

"Treat," "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay in the progression of the condition, delay of the onset of the disorder, and/or change in clinical parameters, disease or illness, etc., as would be well known in the art.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

As used herein, the terms "elicit" or "induce" or "produce" (or grammatical variations thereof) in the context of an immune response against *M. pneumoniae* are intended to encompass the activation and/or stimulation of cells and other components of the immune system in a subject to ameliorate the effects of *M. pneumoniae* infection in the subject. The immune response of this invention can be a protective immune response, for example, as desired in vaccination methods to treat and/or prevent infection. Protection is not required if there is some other purpose for inducing the immune response, for example, for research purposes or to produce antibody for passive immunizations or as a reagent.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

The terms "immunogenic amount" or "effective immunizing dose," as used herein, unless otherwise indicated, mean a dose of a composition of this invention sufficient to induce an immune response (which can be a protective response) in the treated subject that is greater than the inherent immunity of non-immunized subjects. An immunogenic amount or effective amount or effective immunizing dose in any particular context can be routinely determined using methods known in the art.

In some embodiments, an effective immunizing dose or immunogenic amount or effective amount can comprise one or more (e.g., two or three or four or more) doses of the immunogenic composition of this invention at any time interval (e.g., hourly, daily, weekly, monthly, yearly, etc.) so as to achieve and/or maintain the desired level of protection and/or other therapeutic benefit.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

The terms "protective immunity" or "protective immune response," as used herein, are intended to mean that the subject mounts an active immune response to the immunogenic composition and/or that the subject has been provided with passive immunity, such that upon subsequent exposure or a challenge, the animal is able to resist and/or overcome infection and/or disease. Thus, a protective immune response will decrease the incidence of morbidity and/or mortality from subsequent exposure to the pathogens of this invention.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host."Id.

A subject of this invention includes any animal susceptible to infection by *Mycoplasma pneumoniae*. Such a subject can be a mammal and in particular embodiments, is a human. A "subject in need thereof" is a subject known to be, or suspected of being, infected with *Mycoplasma pneumoniae*. A subject of this invention can also include a subject not previously known or suspected to be infected by *Mycoplasma pneumoniae* or in need of treatment for *Mycoplasma pneumoniae* infection. For example, a subject of this invention can be administered the compositions of this invention even if it is not known or suspected that the subject is infected with *Mycoplasma pneumoniae* (e.g., prophylactically). A subject of this invention is also a subject known or believed to be at risk of infection by *Mycoplasma pneumoniae*.

In certain embodiments, the fragments and/or polypeptides of this invention can be fused with a "carrier" protein or peptide to produce a fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., Green Fluorescent Protein, β-glucoronidase, β-galactosidase, luciferase, and the like) for easy detection of transformed cells and transgene expression. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this invention.

The polypeptides and/or fragments of the present invention can 1) be used in assays to determine the biological activity of other proteins or peptides; 2) be included in a panel of multiple proteins for high-throughput screening; 3) be used to raise antibodies or to elicit an immune response; 4) be used as a reagent (including the labeled reagent) in assays designed to quantitatively determine levels of the protein (or its binding partner or receptor) in biological fluids; and 5) be used as markers for tissues in which the corresponding protein is preferentially expressed (either constitutively or at a particular stage of tissue differentiation or development or in a disease state). Any or all of these research utilities are capable of being developed into reagent grade or kit format for commercialization as research products. Methods for performing the uses listed above are well known to those skilled in the art. References disclosing such methods include *Molecular Cloning: A Laboratory Manual*, 2d ed., Cold Spring Harbor Laboratory Press, Sambrook et al., eds. (1989) and *Methods in Enzymology: Guide to Molecular Cloning Techniques*, Academic Press, Berger and Kimmel eds. (1987).

A variety of protocols for detecting the presence of and/or measuring the amount of polypeptides, fragments and/or peptides in a sample, using either polyclonal or monoclonal antibodies specific for the polypeptide, fragment and/or peptide are known in the art. Examples of such protocols include, but are not limited to, enzyme immunoassays (EIA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS). These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

Furthermore, a number of assays for detection and/or amplification of nucleic acid sequences are well known in the art. Additionally, a wide variety of labeling and conjugation techniques are known in the art that are used in various nucleic acid detection and amplification assays. Methods for producing labeled hybridization probes and/or PCR or other ligation primers for detecting and/or amplifying nucleic acid sequences can include, for example, oligolabeling, nick translation and end-labeling, as well as other well known methods. Alternatively, nucleic acid sequences encoding the polypeptides of this invention, and/or any functional fragment thereof, can be cloned into a plasmid or vector for detection and amplification. Such plasmids and vectors are well known in the art and are commercially available. It is also contemplated that the methods of this invention can be conducted using a variety of commercially-available kits (e.g., Pharmacia & Upjohn; Promega; U.S. Biochemical Corp.). Suitable reporter molecules or labels, which can be used for ease of detection, include, for example, radionuclides, enzymes, fluorescence agents, chemiluminescence agents and chromogenic agents, as well as substrates, cofactors, inhibitors, magnetic particles and the like as are well known in the art.

The present invention further includes isolated polypeptides, peptides, proteins, fragments, domains and/or nucleic acid molecules that are substantially equivalent to those described for this invention. As used herein, "substantially equivalent" can refer both to nucleic acid and amino acid sequences, for example a mutant sequence, that varies from a reference sequence by one or more substitutions, deletions, or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologs, as well as methods of obtaining homologs, of the polypeptides and/or fragments of this invention from other strains of *Mycoplasma* and/or other organisms. As used herein, an amino acid sequence or protein is defined as a homolog of a polypeptide or fragment of the present invention if it shares significant homology to one of the polypeptides and/or fragments of the present invention. Significant homology means at least 75%, 80%, 85%, 90%, 95%, 98% and/or 100% homology with another amino acid sequence. Specifically, by using the nucleic acids disclosed herein as a probe or as primers, and techniques such as PCR amplification and colony/plaque hybridization, one skilled in the art can identify homologs of the polypeptides and/or fragments of this invention in *Mycoplasma* and/or other organisms.

The present invention also provides an antibody that specifically binds the polypeptides and/or biologically active fragments of this invention, as well as a method of making an antibody specific for a polypeptide and/or fragment of this invention comprising: a) immunizing an animal with a polypeptide and/or fragment of this invention under conditions whereby the animal produces antibodies that specifically bind the polypeptide and/or fragment of this invention; and b) removing biological materials comprising the antibodies from the animal. Also provided herein is an antibody produced by the methods set forth herein.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. Nos. 4,474,893 or 4,816,567. The antibodies can also be chemically constructed according to the method disclosed in U.S. Pat. No. 4,676,980.

Antibodies of this invention can be generated using methods that are well known in the art. Such antibodies and immunoglobulin molecules of this invention can include, but are not limited to, polyclonal antibodies, monoclonal antibodies, chimeric antibodies, humanized antibodies, single chain antibodies (e.g., scFv), Fab fragments, and fragments produced by a Fab expression library.

In general, techniques for preparing polyclonal and monoclonal antibodies as well as hybridomas capable of producing a desired antibody are well known in the art. Any animal known to produce antibodies can be immunized with a polypeptide, fragment and/or antigenic epitope of this invention. Methods for immunization of animals to produce antibodies are well known in the art. For example, such methods can include subcutaneous or interperitoneal injection of the polypeptide, fragment and/or antigenic epitope of this invention.

The polypeptide, fragment or antigenic epitope that is used as an immunogen can be modified or administered in an adjuvant in order to increase antigenicity. Methods of increasing the antigenicity of a protein or peptide are well known in the art and include, but are not limited to, coupling the antigen with a heterologous protein (such as globulin or β-galactosidase) or through the inclusion of an adjuvant during immunization.

For example, for the production of antibodies, various hosts including goats, rabbits, rats, mice, humans, and others, can be immunized by injection with the polypeptides and/or fragments of this invention, with or without a carrier protein. Additionally, various adjuvants may be used to increase the immunological response. Such adjuvants include, but are not limited to, Freund's complete and incomplete adjuvants, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Polypeptides, peptides and/or fragments of this invention used as antigens to produce the antibodies of this invention can have an amino acid sequence consisting of at least five amino acids and in certain embodiments, at least ten amino acids. In one embodiment, the antigen is identical to a portion of the amino acid sequence of the natural protein, and it can contain the entire amino acid sequence of a small, naturally-occurring molecule. Short stretches of the polypeptides and/or fragments of this invention can be fused with all or a fragment of another protein that acts as a carrier protein (e.g., keyhole limpet hemocyanin) and antibodies can be produced against the chimeric polypeptide or peptide.

Monoclonal antibodies to the polypeptides and/or fragments of this invention are prepared using any technique, which provides for the production of antibody molecules by continuous cell lines in culture, These include, but are not limited to, the hybridoma technique, the human B-cell hybridoma technique, and the EBV-hybridoma technique (Kohler et al. 1975. *Nature* 256:495-497; Kozbor et al. 1985. *J. Immunol. Methods* 81:31-42; Cote et al, 1983. *Proc. Natl. Acad. Sci.* 80:2026-2030; Cole et al. 1984. *Mol. Cell. Biol.* 62:109-120).

For example, to produce monoclonal antibodies, spleen cells from the immunized animal are removed, fused with myeloma cells, and cultured in selective medium to become monoclonal antibody-producing hybridoma cells, according to techniques routine in the art. Any one of a number of methods well known in the art can be used to identify the hybridoma cell, which produces an antibody with the desired characteristics. These include screening the hybridomas by ELISA assay, Western blot analysis, or radioimmunoassay. Hybridomas secreting the desired antibodies are cloned and the class and subclass are identified using standard procedures known in the art.

For polyclonal antibodies, antibody-containing serum is isolated from the immunized animal and is screened for the presence of antibodies with the desired specificity using any of the well known procedures as described herein.

The present invention further provides antibodies of this invention in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescence labels (such as FITC or rhodamine, etc.), paramagnetic atoms, gold beads, etc. Such labeling procedures are well-known in the art. The labeled antibodies of the present invention can be used for in vitro, in vivo, and in situ assays to identify a polypeptide and/or fragment of this invention in a sample.

In some embodiments, the present invention further provides the above-described antibodies immobilized on a solid support (e.g., beads, plates, slides or wells formed from materials such as latex or polystyrene). Examples of such solid supports include plastics such as polycarbonate, complex carbohydrates such as agarose and SEPHAROSE, acrylic resins and such as polyacrylamide and latex beads. Techniques for coupling antibodies to such solid supports are well known in the art (Weir et al., *Handbook of Experimental Immunology* 4th Ed., Blackwell Scientific Publications, Oxford, England, Chapter 10 (1986)). Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In addition, techniques developed for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and fragments of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

Antibody fragments that specifically bind the polypeptides and/or fragments of this invention can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed to allow rapid and easy identification of monoclonal Fab fragments with the desired specificity (Huse et al. 1989. *Science* 254:1275-1281).

Various immunoassays can be used for screening to identify antibodies having the desired specificity for the proteins and peptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). For example, a two-site, monoclonal-based immunoassay utilizing monoclonal antibodies reactive to two non-interfering epitopes on the proteins or peptides of this invention can be used, as well as a competitive binding assay.

Antibody fragments included within the scope of the present invention include, for example, Fab, Fab', F(ab')$_2$, and Fv fragments; domain antibodies, diabodies; vaccibodies, linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature*, 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al. *Nature* 332:323 (1988); Verhoeyen et al., *Science* 239: 1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol, Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention, Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}$S, $^{125}$I, $^{131}$I), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

It is further contemplated that the present invention provides kits for detection of *Mycoplasma pneumoniae* polypeptides, peptides and/or fragments in a sample. In one embodiment, the kit can comprise one or more antibodies of this invention, along with suitable buffers, wash solutions and/or other reagents for the detection of antibody/antigen complex formation. In an alternative embodiment, a kit of this invention can comprise a polypeptide, an antigenic peptide of the polypeptide of this invention, a fragment of this invention and/or an antigenic peptide of a fragment of this invention, along with suitable buffers, wash solutions and/or other reagents for the detection of antibody/antigen complex formation.

The present invention further provides a kit for the detection of nucleic acid encoding the polypeptides and/or fragments of this invention. For example, in one embodiment, the kit can comprise one or more nucleic acids of this invention, along with suitable buffers, wash solutions and/or other reagents for the detection of hybridization complex formation.

It would be well understood by one of ordinary skill in the art that the kits of this invention can comprise one or more containers and/or receptacles to hold the reagents (e.g., antibodies, antigens, nucleic acids) of the kit, along with appropriate buffers and/or wash solutions and directions for using the kit, as would be well known in the art. Such kits can further comprise adjuvants and/or other immunostimulatory or immunomodulating agents, as are well known in the art.

In further embodiments, the nucleic acids encoding the polypeptides and/or fragments of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding a polypeptide and/or biologically active fragment of this invention.

The present invention further provides a vector comprising a nucleic acid encoding a polypeptide and/or fragment of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, vaccinia virus, adenovirus, retrovirus and/or adeno-associated virus nucleic acid. The nucleic acid or vector of this invention can also be in a liposome or a delivery vehicle, which can be taken up by a cell via receptor-mediated or other type of endocytosis.

The nucleic acid of this invention can be in a cell, which can be a cell expressing the nucleic acid whereby a polypeptide and/or biologically active fragment of this invention is produced in the cell. In addition, the vector of this invention can be in a cell, which can be a cell expressing the nucleic acid of the vector whereby a polypeptide and/or biologically active fragment of this invention is produced in the cell. It is also contemplated that the nucleic acids and/or vectors of this invention can be present in a host animal (e.g., a transgenic animal), which expresses the nucleic acids of this invention and produces the polypeptides and/or fragments of this invention.

The nucleic acid encoding the polypeptide and/or fragment of this invention can be any nucleic acid that functionally encodes the polypeptides and/or fragments of this invention. To functionally encode the polypeptides and/or fragments (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Preferred expression control sequences are promoters derived from metallothionine genes, actin genes, immunoglobulin genes, CMV, SV40, adenovirus, bovine papilloma virus, etc. A nucleic acid encoding a selected polypeptide and/or fragment can readily be determined based upon the genetic code for the amino acid sequence of the selected polypeptide and/or fragment and many nucleic acids will encode any selected polypeptide and/or fragment. Modifications in the nucleic acid sequence encoding the polypeptide and/or fragment are also contemplated. Modifications that can be useful are modifications to the sequences controlling expression of the polypeptide and/or fragment to make production of the polypeptide and/or fragment inducible or repressible as controlled by the appropriate inducer or repressor. Such methods are standard in the art. The nucleic acid of this invention can be generated by means standard in the art, such as by recombinant nucleic acid techniques and by synthetic nucleic acid synthesis or in vitro enzymatic synthesis.

In yet further embodiments, the present invention provides a D1 domain of CARDS Toxin comprising, consisting essentially of and/or consisting of the amino acid sequence of SEQ ID NO:69 and/or SEQ ID NO:75, a D2 domain of CARDS Toxin comprising, consisting essentially of, or consisting of the amino acid sequence of SEQ ID NO: 70, and/or a D3 domain of CARDS Toxin comprising, consisting essentially of, and/or consisting of the amino acid sequence of SEQ ID NO:71, in any combination.

Further provided herein is an isolated nucleic acid encoding the amino acid sequence of the domains D1, D2 and D3 of this invention. As one example, a nucleic acid encoding the domain D1 can comprise, consist of and/or consist essentially of the nucleotide sequence of SEQ ID NO:74.

Additionally provided herein are antibodies that specifically bind domain D1, D2 and/or D3 of the CARDS Toxin of this invention. The domain peptides can be used as antigens for the production of antibodies, which can be polyclonal and/or monoclonal, according to well known protocols. The domain peptides and antibodies can be used in the methods described herein for the detection of *M. pneumoniae* antibodies and proteins and/or for diagnosis of *M. pneumoniae* infection, as well as in therapeutic methods to treat *M. pneumoniae* infection and related diseases as described herein.

The present invention further provides a method of producing a polypeptide and/or biologically active fragment according to the methods set forth in the Examples provided herein, and as are well known in the art for polypeptide synthesis. In one embodiment, a nucleic acid encoding the polypeptides and/or fragments of this invention can be synthesized according to standard nucleic acid synthesis protocols and the nucleic acid can be expressed according to methods well known for expression of nucleic acid. The resulting polypeptide and/or fragment can then be removed from the expression system by standard isolation and purification procedures and tested for any of the various biological activities described herein according to methods as taught herein as well as methods routine in the art.

The present invention also provides a method for producing the polypeptides and/or biologically active fragments of this invention comprising producing the cells of this invention which contain the nucleic acids or vectors of this invention as exogenous nucleic acid; culturing the cells under conditions whereby the exogenous nucleic acid in the cell can be expressed and the encoded polypeptide and/or fragment can be produced; and isolating the polypeptide and/or fragment from the cell. Thus, it is contemplated that the polypeptides and/or fragments of this invention can be produced in quantity in vitro in either prokaryotic or eukaryotic expression systems as are well known in the art.

As one example, for expression in a prokaryotic system, there are numerous *E. coli* (*Escherichia coli*) expression vectors known to one of ordinary skill in the art useful for the expression of nucleic acid that encodes polypeptides. Other microbial hosts suitable for use include bacilli, such as *Bacillus subtilis*, and other enterobacteria, such as *Salmonella, Serratia*, as well as various *Pseudomonas* species. These prokaryotic hosts can support expression vectors that will typically contain expression control sequences compatible with the host cell (e.g., an origin of replication). In addition, any number of a variety of well-known promoters can be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the polypeptide. Also, the carboxy-terminal extension of the polypeptide can be removed using standard oligonucleotide mutagenesis procedures.

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences.

As another example, for eukaryotic system expression, a yeast expression system can be used. There are several advantages to yeast expression systems. First, evidence exists that polypeptides produced in a yeast expression system exhibit correct disulfide pairing. Second, post-translational glycosylation is efficiently carried out by yeast expression systems. The *Saccharomyces cerevisiae* pre-pro-alpha-factor leader region (encoded by the MFa-1 gene) is routinely used to direct protein secretion from yeast. The leader region of pre-pro-alpha-factor contains a signal peptide and a pro-segment, which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase I promoter or a glycolytic promoter. The coding sequence is followed by a translation termination codon, which is followed by transcription termination signals. Alternatively, the coding sequence of interest can be fused to a second polypeptide coding sequence, such as Sj26 or β-galactosidase, used to facilitate purification of the resulting fusion polypeptide by affinity chromatography. The insertion of protease cleavage sites to separate the components of the fusion polypeptide is applicable to constructs used for expression in yeast.

Efficient post-translational glycosylation and expression of recombinant polypeptides can also be achieved in Baculovirus systems in insect cells, as are well known in the art.

In yet further embodiments, the peptides, polypeptides and/or fragments of this invention can be expressed in mammalian cells. Mammalian cells permit the expression of peptides and polypeptides in an environment that favors important post-translational modifications such as folding and cysteine pairing, addition of complex carbohydrate structures and secretion of active protein. Vectors useful for the expression of peptides and polypeptides in mammalian cells are characterized by insertion of the coding sequence between a strong (e.g., viral) promoter and a polyadenylation signal. The vectors can contain genes conferring either, e.g., gentamicin or methotrexate resistance, for use as selectable markers. For example, the coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the polypeptide or fragment coding sequence can be confirmed by Southern and Northern blot analysis, respectively. A number of other suitable host cell lines capable of producing exogenous polypeptides have been developed in the art and include the CHO cell lines, HeLa cells, myeloma cell lines, Jurkat cells and the like. Expression vectors for these cells can include expression control sequences, as described above.

The nucleic acids and/or vectors of this invention can be transferred into the host cell by well-known methods, which vary depending on the type of cell host. For example, calcium chloride transfection is commonly used for prokaryotic cells, whereas calcium phosphate treatment or electroporation can be used for other cell hosts.

The polypeptides, fragments, nucleic acids, vectors and cells of this invention can be present in a pharmaceutically acceptable carrier. By "pharmaceutically acceptable" is meant a material that is not biologically or otherwise undesirable, i.e., the material may be administered to an individual along with the selected polypeptide, fragment, nucleic acid, vector or cell without causing substantial deleterious biological effects or interacting in a deleterious manner with any of the other components of the composition in which it is contained.

Furthermore, any of the compositions of this invention can comprise a pharmaceutically acceptable carrier and a suitable adjuvant. As used herein, "suitable adjuvant" describes an adjuvant capable of being combined with the polypeptide and/or fragment and/or nucleic acid of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (TWEEN 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/TWEEN 80 emulsion.

The compositions of the present invention can also include other medicinal agents, pharmaceutical agents, carriers, diluents, immunostimulatory cytokines, etc. Actual methods of preparing such dosage forms are known, or will be apparent, to those skilled in this art.

It is contemplated that the above-described compositions of this invention can be administered to a subject or to a cell of a subject to impart a therapeutic benefit. Thus, the present invention further provides a method of producing an immune response in a subject, comprising administering to the subject or to a cell of the subject an effective amount of a polypeptide and/or biologically active fragment of this invention and/or a nucleic acid comprising a nucleotide sequence encoding a polypeptide and/or biologically active fragment of this invention. The cell of the subject can be in vivo or ex vivo and can be, but is not limited to a CD8+ T lymphocyte (e.g., a cytotoxic T lymphocyte) or an MHC I-expressing antigen presenting cell, such as a dendritic cell, a macrophage and/or a monocyte. Detection of an immune response in the subject or in the cells of the subject can be carried out according to methods standard in the art for detecting a humoral and/or cellular immune response.

Furthermore, the present invention provides a method of eliciting an immune response in a subject, comprising administering to the subject an effective amount of a polypeptide and/of fragment of this invention.

Also provided herein is a method of eliciting an immune response in a subject, comprising administering to the subject an effective amount of a nucleic acid and/or vector of this invention.

In additional embodiments, the present invention provides a method of providing passive immunity to a subject, comprising administering to the subject an effective amount of an antibody of this invention to the subject.

The compositions of this invention can also be employed as a therapeutic and/or prophylactic formulation and administered to a subject in need thereof. Thus, the present invention provides a method of treating or preventing infection or intoxication by *Mycoplasma pneumoniae* in a subject, comprising administering to the subject an effective amount of a polypeptide and/or fragment of this invention, a nucleic acid and/or vector of this invention, and/or an antibody of this invention.

In addition, the present invention provides a method of treating or preventing infection or intoxication caused by *Mycoplasma pneumoniae* in a subject comprising contacting an immune cell of the subject with any of the polypeptides, fragments, nucleic acids, vectors and/or antibodies of this invention. The cell can be in vivo or ex vivo and can be, for example, a $CD8^+$ T cell which is contacted with the polypeptide and/or fragment of this invention in the presence of a class I MHC molecule, which can be a soluble molecule or it can be present on the surface of a cell which expresses class I MHC molecules. The cell can also be an antigen presenting cell or other class I MHC-expressing cell which can be contacted with the nucleic acids and/or vectors of this invention under conditions whereby the nucleic acid or vector is introduced into the cell by standard methods for uptake of nucleic acid and vectors. The nucleic acid encoding the polypeptide and/or fragment of this invention is then expressed and the polypeptide and/or fragment product is processed within the antigen presenting cell or other MHC I-expressing cell and presented on the cell surface as an MHC I/antigen complex. The antigen presenting cell or other class I MHC-expressing cell is then contacted with an immune cell of the subject which binds the class I MHC/antigen complex and elicits an immune response which treats or prevents *Mycoplasma pneumoniae* infection in the subject.

As set forth above, it is contemplated that in the methods wherein the compositions of this invention are administered to a subject or to a cell of a subject, such methods can further comprise the step of administering a suitable adjuvant to the subject or to a cell of the subject. The adjuvant can be in the composition of this invention or the adjuvant can be in a separate composition comprising the suitable adjuvant and a pharmaceutically acceptable carrier. The adjuvant can be administered prior to, simultaneous with, or after administration of the composition containing any of the polypeptides, fragments, nucleic acids and/or vectors of this invention. For example, QS-21, similar to alum, complete Freund's adjuvant, SAF, etc., can be administered within days/weeks/hours (before or after) of administration of the composition of this invention. The effectiveness of an adjuvant can be determined by measuring the immune response directed against the polypeptide and/or fragment of this invention with and without the adjuvant, using standard procedures, as described in the Examples herein and as are well known in the art.

As set forth above, the subject of this invention can be any subject in need of the immune response of this invention and/or in need of treatment for or prevention from *Mycoplasma pneumoniae* infection, as well as any subject in whom it is desirable to induce an immune response to *Mycoplasma pneumoniae*. Symptoms of *Mycoplasma pneumoniae* infection can include tracheobronchitis and pneumonia with extrapulmonary pathologies, such as neurologic, cardiac, gastrointestinal, dermatologic, renal and joint complications. A range of serological (elevated IgM and IgG seroconversion) assays and PCR detection can be used for diagnosing *M. pneumoniae* infection. Appropriate treatment can lead to resolution of respiratory symptoms such as decreased fever and cough, complete recovery of respiratory function including normal lung radiogram, and normal levels of tissue enzymes and CSF analysis. Also, decreased levels of *M. pneumoniae* cells, antigens and nucleic acids in blood, sputum, bronchial lavage should accompany effective treatment.

Common sources of infection can include infected individuals coughing, sneezing and transmitting aerosols containing *M. pneumoniae*. The transmission rate is very high, which is why *M. pneumoniae* is such a common cause of community acquired pneumonia. Highest targets of infection are children, especially 5-9 years old and adults between ages 25-40, although infection can occur among all 'healthy' individuals. Thus, a subject for whom the methods of this invention would be indicated for preventing *M. pneumoniae* infection can, in some embodiments, be a child or young adult.

The antibodies, antibody fragments, peptides, polypeptides and compositions of this invention can be administered to a cell of a subject or to a subject either in vivo or ex vivo. For administration to a cell of the subject in vivo, as well as for administration to the subject, the antibodies, antibody fragments, peptides, polypeptides and compositions of this invention can be administered orally, parenterally (e.g., intravenously), by intramuscular injection, by intraperitoneal injection, subcutaneous injection, transdermally, extracorporeally, topically or the like. Also, the antibodies, antibody fragments, peptides, polypeptides and compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount of the antibodies, antibody fragments, peptides, polypeptides and compositions required will vary from subject to subject, depending on the species, age, weight and general condition of the subject, the particular composition used, its mode of administration and the like. Thus, it is not possible to specify an exact amount for every antibody, antibody fragment, peptide, polypeptide or composition of this invention. However, an effective amount can be determined by one of ordinary skill in the art using only routine experimentation given the teachings herein.

As an example, to a subject diagnosed with *M. pneumoniae* infection or known to be at risk of being infected with *M. pneumoniae* or in whom it is desirable to induce an immune response to *Mycoplasma pneumoniae* or *M. pneumoniae* CARDS toxin, between about 50-1000 nM and more preferably, between about 100-500 nM of a polypeptide, peptide and/or biologically active fragment of this invention can be administered subcutaneously and can be in an adjuvant, at one to three hour/day/week intervals until an evaluation of the subject's clinical parameters indicate that the subject is not infected by *M. pneumoniae* and/or the subject demonstrates the desired immunological response. Alternatively, a polypeptide, peptide and/or fragment of this invention can be pulsed onto dendritic cells at a concentration of between about 10-100 µM and the dendritic cells can be administered to the subject intravenously at the same time intervals. Dosage of an antibody will depend, among other things, on the disorder being treated, the route of administration, the nature of the therapeutic agent employed, the patient's condition, etc. As a nonlimiting example the dosage can be from about 0.1 microgram to 100 milligrams per kilogram subject body weight. Dosages of pharmaceutically active compounds such as those described herein can be determined by methods known in the art, see, e.g., *Remington's Pharmaceutical Sciences* (Maack Publishing Co., Easton, Pa., latest edition). The treatment can be continued or resumed if the subject's clinical parameters indicate that *M. pneumoniae* infection is present and can be maintained until the infection is no longer detected by these parameters and/or until the desired immunological response is achieved.

If ex vivo methods are employed, cells or tissues can be removed and maintained outside the subject's body according to standard protocols well known in the art. The polypeptides and/or biologically active fragments of this invention can be introduced into the cells via known mechanisms for uptake of polypeptides into cells (e.g., phagocytosis, pulsing onto class I MHC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

The nucleic acids and vectors of this invention can also be administered to a cell of the subject either in vivo or ex vivo. The cell can be any cell that can take up and express exogenous nucleic acid and produce the polypeptides and/or fragments of this invention. In some embodiments, the polypeptides and/or fragments of this invention can be produced by a cell that secretes them, whereby the polypeptide and/or fragment is produced and secreted and then taken up and subsequently processed by an antigen presenting cell or other class I MHC-expressing cell and presented to the immune system for induction of an immune response. In other embodiments, the nucleic acids and/or vectors of this invention can be directly introduced into an antigen presenting cell and/or other class I MHC-expressing cell in which the polypeptide and/or fragment is produced and processed directly and presented to the immune system on the cell surface.

The nucleic acids and vectors of this invention can be administered orally, intranasally, parenterally (e.g., intravenously), by intramuscular injection, by intraperitoneal injection, transdermally, extracorporeally, topically or the like. In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the polypeptides and/or fragments of this invention. The vector can be a commercially available preparation or can be constructed in the laboratory according to methods well known in the art.

Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system, which can package a recombinant retroviral genome. The recombinant retrovirus can then be used to infect and thereby deliver to the infected cells nucleic acid encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors, adeno-associated viral (AAV) vectors, lentiviral vectors, pseudotyped retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

As another example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$, $10^{15}$ and/or $10^{20}$ pfu per injection. Ideally, a subject will receive a single injection. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein and/or by detecting a desired immunological response.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

If ex vivo methods are employed, cells or tissues can be removed and maintained outside the body according to standard protocols well known in the art. The nucleic acids and vectors of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type.

Standard methods are known for transplantation or infusion of various cells into a subject.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, intranasal, subcutaneous, intramuscular, intraperitoneal, intravenous and intratracheal routes, as well as a slow release or sustained release system such that a constant dosage is maintained. See, e.g., U.S. Pat. No. 3,610,795, which is incorporated by reference herein in its entirety.

The efficacy of treating or preventing *Mycoplasma pneumoniae* infection by the methods of the present invention can be determined by detecting a clinical improvement as indicated by a change in the subject's symptoms and/or clinical parameters, as would be well known to one of skill in the art.

It is further contemplated that the compositions of the present invention can be used in diagnostic and therapeutic applications. Thus, the present invention provides a method of detecting the presence of a polypeptide and/or fragment of this invention in a sample, comprising contacting the sample with an antibody of this invention under conditions whereby an antigen/antibody complex can form and detecting formation of an antigen/antibody complex, thereby detecting the presence of a *Mycoplasma pneumoniae* polypeptide and/or fragment of this invention in the sample.

Additionally, the present invention provides a method of detecting the presence of an antibody of this invention in a sample, comprising contacting the sample with a polypeptide and/or fragment of this invention under conditions whereby an antigen/antibody complex can form and detecting formation of an antigen/antibody complex, thereby detecting the presence of a *Mycoplasma pneumoniae* antibody of this invention in the sample.

The sample of this invention can be any sample in which *Mycoplasma pneumoniae* exotoxin can be present. For example, the sample can be a body fluid, cells or tissue that can contain *Mycoplasma pneumoniae* exotoxin, including but not limited to, blood, serum, plasma, saliva, sputum, bronchoalveolar lavage, urine, semen, joint fluid, cerebrospinal fluid and cells, fluids and/or tissue from all organs to which CARDS toxin can disseminate including lung, liver, heart, brain, kidney, spleen, muscle, etc.

Additionally, the present invention provides a method of diagnosing *Mycoplasma pneumoniae* infection in a subject comprising contacting a biological sample from the subject with a polypeptide and/or fragment of this invention under conditions whereby an antigen/antibody complex can form; and detecting formation of an antigen/antibody complex, thereby diagnosing *Mycoplasma pneumoniae* infection in the subject.

A method of diagnosing *Mycoplasma pneumoniae* infection in a subject is further provided, comprising contacting a biological sample from the subject with an antibody of this invention under conditions whereby an antigen/antibody complex can form; and detecting formation of an antigen/antibody complex, thereby diagnosing *Mycoplasma pneumoniae* infection in the subject.

In further embodiments, the present invention provides a method of diagnosing infection by *Mycloplasma pneumoniae* in a subject, comprising contacting a biological sample from the subject with the nucleic acid of this invention under conditions whereby hybridization of nucleic acid molecules can occur and detecting a hybridization complex, thereby diagnosing infection by *Mycoplasma pneumoniae* in the subject.

In additional embodiments, the present invention provides a method of identifying a subject infected with *Mycoplasma pneumoniae* as having a poor prognosis, comprising:

a) establishing a correlation between the presence of and/or an amount of a polypeptide, fragment, nucleic acid and/or antibody of this invention in a sample of test subjects infected with *Mycoplasma pneumoniae* and who have or had a poor prognosis;

b) detecting in a biological sample from the subject the presence of and/or an amount of the polypeptide, fragment, nucleic acid and/or antibody of this invention correlated with a poor prognosis, thereby identifying the subject infected with *Mycoplasma pneumoniae* as having a poor prognosis. For example, a correlation can be made between a level of antibodies to the CARDS toxin and a degree of respiratory and/or pulmonary dysfunction indicative of a poor prognosis.

The present invention also provides various screening assays that employ the polypeptides, fragments and/or nucleic acids of this invention. In particular, provided herein is a method of identifying a substance having the ability to inhibit or enhance the binding activity of a polypeptide and/or biologically active fragment of this invention comprising contacting the substance with the CARDS protein or a biologically active fragment thereof under conditions whereby binding can occur and detecting a decrease or increase in the amount of binding in the presence of the substance as compared to a control amount of binding in the absence of the substance, thereby identifying a substance having the ability to inhibit or enhance the binding activity of the CARDS toxin.

Inhibition or enhancement of binding activity can be detected by any of a variety of art-recognized methods for evaluating binding activity. As one example, the substance to be tested and the CARDS polypeptide and/or fragment can be contacted in the presence of target cells or a target substrate (e.g., surfactant protein A; SP-A) known to bind the polypeptide or fragment. The amount of binding of polypeptide or fragment to the cells or the substrate in the presence of the substance and the amount of binding of polypeptide or fragment to the cells or the substrate in the absence of the substance is determined and a decrease or increase in the amount of binding in the presence of the substance identifies the substance as having the ability to inhibit or enhance binding.

In some embodiments, binding of polypeptide and/or fragment to target cells or a target substrate can be measured by attaching a detectable moiety to the polypeptide or fragment (e.g., a fluorescence moiety, histochemically detectable moiety, radioactive moiety, etc.). The amount of detectable moiety can be measured in the presence and absence of the substance to be tested and the amounts can be compared to determine inhibition or enhancement. Binding activity can also be determined by comparing the amount of cytopathology observed in a monolayer of target cells in the presence and absence of the substance to be tested. Target cells that can be used in such a binding assay include, but are not limited to, Chinese hamster ovary (CHO) cells, Hep2 cells, human lung and kidney epithelial and fibroblast cells, and any other mammalian cells that exhibit sensitivity to CARDS toxin now known or later identified.

In addition, the present invention provides a method of identifying a substance having the ability to inhibit or enhance the translocating activity of a polypeptide and/or a biologically active fragment of this invention, comprising contacting the substance with the polypeptide of this invention and/or a biologically active fragment thereof under conditions whereby translocation activity can occur and detecting a decrease or increase in the amount of translocation activity in the presence of the substance as compared to a control amount of translocation activity in the absence of the substance, thereby identifying a substance having the ability to inhibit or enhance the translocating activity of the CARDS toxin.

Inhibition or enhancement of translocating activity can be detected by any of a variety of art-recognized methods for evaluating translocating activity. As one example, the substance to be tested and the CARDS polypeptide and/or fragment can be contacted in the presence of target cells known to translocate the CARDS exotoxin. The amount of translocation of polypeptide or fragment into the cells in the presence of the substance and the amount of translocation of polypeptide or fragment into the cells in the absence of the substance is determined and a decrease or increase in the amount of translocation in the presence of the substance identifies the substance as having the ability to inhibit or enhance translocation of the CARDS exotoxin. Translocation of polypeptide and/or fragment into target cells can be measured by attaching a detectable moiety to the polypeptide or fragment (e.g., a fluorescence moiety, histochemically detectable moiety, radioactive moiety, etc.). The amount of translocated detectable moiety can be measured in the presence and absence of the substance to be tested and the amounts can be compared to determine inhibition or enhancement of translocation. Translocation activity can also be determined by comparing the amount of cytopathology observed in a monolayer of target cells in the presence and absence of the substance to be tested. Target cells that can be used in such a translocation assay include, but are not limited to, Chinese hamster ovary (CHO) cells, etc.

Further provided is a method of identifying a substance having the ability to enhance or inhibit the immunogenic activity of the CARDS toxin of this invention and/or a biologically active fragment thereof, comprising contacting the substance with the CARDS toxin or an immunogenic fragment thereof under conditions whereby a measurable immune response can be elicited and detecting an increase or decrease in the amount of immune response in the presence of the substance, as compared to a control amount of immune response in the absence of the substance, thereby identifying a substance having the ability to enhance or inhibit immunogenic activity of the CARDS toxin. Assays to detect and measure immune responses are well known in the art and can be employed to detect either humoral or cellular immune responses.

In additional embodiments, the present invention provides a method of identifying a substance having the ability to inhibit or enhance the ADP-ribosylating activity of the CARDS toxin of this invention and/or biologically active fragments thereof, comprising contacting the substance with the CARDS toxin or biologically active fragment thereof under conditions whereby ADP ribosylation can occur and detecting a decrease or increase in the amount of ADP ribosylation in the presence of the substance as compared to a control amount of ADP ribosylation in the absence of the substance, thereby identifying a substance having the ability to inhibit or enhance the ADP ribosylating activity of the CARDS toxin.

Methods for detecting ADP ribosylating activity are well known in the art and are described, for example, in the Examples section provided herein.

Further provided is a method of identifying a substance having the ability to inhibit or enhance the cytopathology-inducing activity of the CARDS toxin of this invention and/or a biologically active fragment thereof, comprising contacting the substance with the CARDS toxin or biologically active fragment thereof under conditions whereby cytopathology (e.g., changes in cell morphology, monolayer characteristics, etc.) of target cells can be induced and detecting a decrease or increase in the amount of cytopathology in the presence of the substance, as compared to a control amount of cytopathology in the absence of the substance, thereby identifying a substance having the ability to inhibit or enhance the cytopathology-inducing activity of the CARDS toxin or biologically active fragment thereof.

Methods of detecting cytopathology of cells are well known in the art and are described, for example, in the Examples section herein.

Substances identified in the screening assays of this invention to have the ability to inhibit or enhance various of the activities of the polypeptides and/or fragments of this invention can be employed in methods of diagnosing *M. pneumoniae* infection, as well as in methods of treating and/or preventing *M. pneumoniae* infection. For example, such substances can be present in a pharmaceutically acceptable carrier for administration to a subject and an effective amount of the substance can be administered to a subject to treat and/or prevent infection by *Mycoplasma pneumoniae*.

It is also contemplated that the present invention includes methods of screening *Mycoplasma pneumoniae* cultures for mutants defective in one or more of the biological activities of the CARDS exotoxin, for use in a vaccine preparation. Such mutants can be identified as having a defect in any of the biological activities of the CARDS exotoxin according to the protocols described herein and as are known in the art. Such mutants can be further tested for being attenuated in the ability to produce a clinical infection in a subject (i.e., for virulence potential) and then further evaluated for use as a vaccine according to known protocols.

For example, in one embodiment, CARDS toxin mutants of *Mycoplasma pneumoniae* (e.g., having a mutation in the CARDS coding sequence or lacking the CARDS coding sequence) can be generated through such art-known techniques as gene disruption and their virulence potential determined by challenge studies in hamsters and by adherence and cytopathology assessments in hamster tracheal rings in organ culture and in cell culture, as is well known in the art. In addition, complementation studies can be performed to restore the defective activity of the CARDS toxin, in order to characterize the mutant.

The present invention is more particularly described in the following examples, which are intended as illustrative only since numerous modifications and variations therein will be apparent to those skilled in the art.

EXAMPLES

*Mycoplasma* Strains and DNA Isolation Conditions.

*M. pneumoniae* reference strain M129/B9 and clinical isolates S1, L2, JL1 and RJL1 were grown to late logarithmic phase in SP-4 medium at 37° C. for 72 h in 150-cm$^2$ tissue culture flasks. Mycoplasmas were harvested by washing three times with PBS [150 mM NaCl, 10 mM sodium phosphate, pH 7.4] and pelleting at 12,500 g for 15 min at 4° C. *M. pneumoniae* chromosomal DNA was isolated using Easy DNA kit according to the manufacturer's protocol (Invitrogen).

Mycoplasma Culture Conditions for Radiolabeling.

Wild-type *Mycoplasma pneumoniae* M129/B9 and clinical isolates were grown in SP-4 medium as above. Mycoplasma monolayers in logarithmic growth phase were washed two times with 10 ml PBS (pH 7.4) and one time with Dulbecco Modified Eagle Medium (DMEM) without L-cysteine and L-methionine and resuspended in 10 ml Dulbecco Modified Eagle Medium (DMEM) without L-cysteine and L-methionine supplemented with 10% heat-inactivated fetal bovine serum and 100 μCi L-[$^{35}$S]methionine. After 4 h incubation at 37° C., supernatants were removed and monolayers washed twice with 25 ml PBS. Mycoplasma cells were scraped into a volume of 10 ml sterile PBS, collected by centrifugation at 9,500×g and washed multiple times in PBS. Cell pellets were resuspended in 1 ml complete lysis buffer (CLB) prepared shortly before use (150 mM NaCl, 10 mM Tris, 20 μM EGTA, 0.5 M TRITON-X 114, 1 mM CaCl$_2$ and protease inhibitors 1 μM pepstatin A, 200 μM PMSF, 1 mM N-α-p-tosyl-L-lysine chloromethyl ketone (TLCK), and 10 μM leupeptin. Cell pellets in CLB were sheared through 25 gauge needles using 3 ml syringes to obtain clear lysis. 20 μl aliquots of resuspended cell lysate were transferred to separate microfuge tubes for SDS-PAGE analysis and scintillation counter assessment (Beckman Instruments Inc. Irvine, Calif.). Radiolabeled lysates were diluted to 6 ml in CLB and passed through control and experimental SP-A columns (see below) in parallel.

Purification of SP-A Binding Proteins

A 20×1.2 cm control glass column was packed with 3 ml uncoupled SEPHAROSE, another identical (experimental) column was packed with 3 ml SEPHAROSE coupled to SP-A Coupling of SP-A to SEPHAROSE CL-4B was performed as follows: A total of 1.5 mg of SP-A was coupled to 2 g of CNBr-activated SEPHAROSE CL-4B according to the manufacturer's instructions except the coupling buffer was 10 mM sodium bicarbonate, pH 8.3. SP-A coupled SEPHAROSE was stored in 5 ml of 5 mM Tris pH 7.5, containing 1 mM NaN$_3$. Columns were equilibrated with 50 ml CLB prior to addition of radiolabeled cell lysates. Radiolabeled cell lysates were collected and reapplied to each column 3-4 times. After samples were added, columns were washed with 10 times volume of packed material to remove unbound proteins. *M pneumoniae* SP-A-binding proteins were eluted using a NaCl gradient (0.2 to 3 M NaCl) containing 10 mM EDTA. Eluates were collected as 1 ml fractions, and 20 μl from each fraction was assayed for specific activity with a scintillation counter.

SDS-PAGE and Autoradiogram.

Fractions eluted from columns were individually dialyzed/desalted against PBS and concentrated by an Amicon concentrator/lyophilizer to $\frac{1}{30}^{th}$ of original volume. Samples were resolved in 12% SDS-PAGE and stained with COOMASSIE brilliant blue or transferred to nitrocellulose and exposed to Kodak XRP-40 X-ray film (Kodak, Rochester, N.Y.) for 4-8 days.

MALDI-TOF Protein Sequencing.

SDS-polyacrylamide gels containing *M pneumoniae* SP-A binding proteins were stained with COOMASSIE brilliant blue and washed thoroughly in distilled water. Individual protein bands were excised from acrylamide gels and subjected to MALDI-TOF by the microsequencing facility at Baylor College of Medicine (Houston, Tex.).

Bacterial Strains, Plasmids and DNA Manipulations.

*Escherichia coli* INVαF' [F' endA1rec1hsdR17supE44gyrA96lacZM15 (lacZYAargF)] (Invitrogen) and *E. coli* BL21(DE3) [F' ompT hsdS ($r_B^-m_B^-$) gal dcm λ(DE3) pLysS] were grown in Luria Bertani (LB) broth and used to clone and express mycoplasma CARDS toxin genes. For DNA manipulations, the following vectors were used: pCR2.1 (Ap$^r$, Km$^r$ TA cloning vector [Invitrogen]) and pET19b (Ap$^r$, N-terminal His$^{10}$ tag, expression vector [Novagen]). Plasmid DNA was purified using the QIAprep spin protocol according to the manufacturer (Qiagen).

SOE-PCR

In attempting to determine precise binding motifs of *M. pneumoniae* SP-A binding proteins, both full size and truncated overexpressed proteins are employed. Initially, the number of truncated proteins will depend upon the number and location of UGA codons. Should the possibility arise that SP-A binding motifs are located in UGA-coded regions of a protein, this issue will be addressed using full-size proteins, or protease-digested peptide fragments, or synthetic peptides as described herein. UGA usage problems in genes encoding SP-A binding proteins, as well as other mycoplasma proteins, are known. In such proteins, the UGA codons in the corresponding genes are modified by site-directed mutagenesis to express full size proteins. PCR-based "splicing by overlap extension" (SOE) methods are employed to mutagenize UGA in these genes. This method is based on the principle that two overlapping complementary ends may prime on each other and be extended to yield a hybrid product, and a second PCR with two primers annealing at the non-overlapping ends will amplify this hybrid. An example of a stepwise strategy for SOE-PCR is as follows. 1. 'a' and 'd' are primers for a gene and 'b' and 'c' are primers to mutagenize the UGA region. 2. Amplification carried out with primers 'a' and 'b' and using genomic DNA as template gives a DNA fragment "AB" of the gene. 3. Amplification carried out with primers 'c' and 'd' and using genomic DNA as template will give DNA fragment "CD" of the gene. 4. Amplification with primers 'a' and 'd' and using DNA fragments "AB"+"CD" as templates will give the UGA modified mutant gene fragment. The overlapping primers covering the UGA codon in the genes are modified as UGG, a codon that still codes for tryptophan, and the primer sets depend upon the number of UGAs to be mutated in each gene. In all cases, genomic DNA of *M. pneumoniae* is used as template, and AccuTaq polymerase mix (Sigma) is used to amplify DNA fragments.

Immunoblot Assay

Mycoplasma total proteins or purified recombinant CARDS protein were resolved on 4-12% SDS-polyacrylamide gels (NuPAGE, InVitrogen) (His-tag released, i.e., minus His tag) and transferred electrophoretically to nitrocellulose membranes (Towbin et al., 1979). Membranes were blocked for two hours with 5% (wt/vol) BLOTTO [nonfat dry milk in TBS containing 0.1% TWEEN-20 (TBST)], followed by three washes with TBST, and incubated with *M. pneumoniae* infected patient sera (1:50 to 1:100 in 2% blotto) at RT for 2 h. Then, individual membranes were washed three times (15 min per wash) in TBST and incubated for 2 h (ambient temperature) with alkaline phosphatase-conjugated goat anti-human IgG Abs at a dilution of 1:2000 in TBST, which were washed 5 additional times with TBST, then color developed with BCIP/NBT tablets (Sigma).

FIG. 1 is an immunoblot of sera from three patients, RJ, 1970 and MJ, infected with *Mycoplasma pneumoniae*. Purified M *pneumoniae* recombinant CARDS toxin was resolved in 4-12% SDS-PAGE and transferred to nitrocellulose membranes. Membranes were blocked for two hours with 5% BLOTTO and treated with patients' sera for two hours at room temperature. Patients' sera were diluted as follows. RJ and MJ: 1:50, and 1970: 1:100 in 2% BLOTTO. Membranes were washed and treated with alkaline phosphatase-conjugated goat anti-human antibodies diluted 1:2000 in TBS-T and two hours and color developed. Patients RJ and MJ died within about three weeks of infection and patient 1970 was hospitalized with mycoplasmal pneumonia and recovered. A 68 kDa MW recombinant CARDS toxin is indicated by the arrow; higher molecular weight and diffuse bands represent His-tagged subpopulation of recombinant CARDS toxin. Detection of antibodies to the CARDS toxin indicates in situ synthesis of CARDS toxin during infection and its immunogenicity.

Additional Studies on Patients Infected with *M. pneumoniae*.

In further studies, acute and convalescent sera were collected from patients with *Mycoplasma pneumoniae*-diagnosed respiratory infections that ranged from tracheobronchitis to bronchopneumonia. Two or three blood samples were obtained from each patient. The first blood sample was collected during the acute phase of the disease, approximately two weeks following exposure to *M. pneumoniae*. The second and third "convalescent" serum samples were obtained 14 and 28 days later, respectively. Control baseline serum samples were obtained from pregnant women attending the University of Texas Health Science Center at San Antonio OB-GYN clinic.

All serum samples were assessed by immunoblotting against total *M. pneumoniae* proteins. Specifically, to detect CARDS toxin protein in patients' sera, *M. pneumoniae* total cell preparations of different clinical isolated (RJ1, J1, S1 and L2) and laboratory strain (B9) were dissolved in 150 μl SDS sample buffer, boiled for two minutes and separated by SDS-PAGE using 4-12% NuPAGE SDS-polyacrylamide gels. Proteins were transferred to nitrocellulose membranes (Shleicher & Schull, Dassel, Germany) by electroblotting. Membranes were blocked for one hour at room temperature with blocking buffer (20 mM Tris-base, 150 mM NaCl, 3% skim milk powder) and incubated with anti-CARDS Toxin mouse polyclonal antibodies diluted 1:2000 in antibody buffer (20 mM Tris-base, 150 mM NaCl, 3% skim milk powder) for one hour at 37° C. Bound IgG was detected with alkaline phosphatase (AP)-conjugated goat-antimouse IgG diluted 1:3000. Membranes were developed for 1-5 minutes with nitroblue tetrazolium (NBT) and 5-bromo-4-chloro-3-indolyl phosphate p-toluidium (BCIP) solution. Results of the immunoblotting show a colored band of 68 kDa molecular weight on each membrane and thus demonstrate the presence of the CARDS toxin protein in each clinical isolate at concentrations that appear to vary among individuals.

Additional immunoblot analyses were carried out to detect antibodies to CARDS toxin in infected patients' sera wherein *M. pneumoniae* recombinant 68 kDa CARDS (rCARDS) toxin (3 μg) or the N terminal domain of CARDS toxin, rD1 (1 μg) as described herein was dissolved in 150 μA LDS sample buffer (NuPAGE), boiled for two minutes and separated by SDS-PAGE using 4-12% NuPAGE SDS-polyacrylamide gels. Proteins were transferred to nitrocellulose membranes (Schleicher & Schull, Dassel, Germany) by electroblotting and membranes were blocked for one hour at room temperature with blocking buffer (20 mM Tris-base, 150 mM NaCl, 3% skim milk powder). Membranes were cut into 3 mm strips and incubated with human serum samples diluted 1:200 in buffer (20 mM Tris-base, 150 mM NaCl, 3% skim milk powder) for one hour at 37° C. Serum samples were from M pneumonia-infected patients designated patients 1 and 2 and the first serum samples were collected during the acute phase of disease (designated 1-1 and 2-1, respectively). The second serum samples (1-2 and 2-2) and third serum samples (1-3 and 2-3) were obtained 14 and 28 days later, respectively.

Bound IgG was detected with alkaline phosphatase (AP)-conjugated goat-antihuman IgG diluted 1:3000. Individual strips were developed for 1-5 minutes with nitroblue tetrazolium (NBT) and 5-bromoL4-chloro-3-indolyl phosphate p-toluidium (BCIP) solution. Results of the immunoblotting showed a colored band of 68 kDa molecular weight on each membrane containing rCARDs toxin and colored bands of 32 kDa and 28 kDa on each membrane containing the D1 domain, thus demonstrating seroconversion in these patients and detection of antibodies to the CARDS toxin, either as a recombinant protein or as the D1 domain. In the latter assay, the color intensity of each band appears to increase in the samples in a manner consistent with the time course of collection from the patient during the course of the disease (i.e., 1-1<1-2<1-3) (FIG. 3).

ELISAs were also carried out on the samples collected from patients 1 and 2 described above (i.e., samples 1-1, 1-2, 1-3, 2-1, 2-2, and 2-3). In these assays, washing at each stage was performed at least three times with PBS and sera and antibodies were diluted in 1% BSA in PBS. Each well of IMMULON 4 HBX Immunoplates (Dynox) was coated overnight at 4° C. with 50 μl of rCARDS toxin/D1 (1 μg/well) diluted in carbonate/bicarbonate buffer (32 mM $Na_2CO_3$, 64 mM NaHCO$_3$). Individual plates were washed, 100 µl of 1 mg/ml (wt/vol) BSA in PBS was added to each well, and incubation continued for two hours at room temperature. After washing, 50 µl of diluted human serum samples (1/50 to 1/3200) were added to each well, and plates were incubated for two hours at room temperature. Then, plates were washed, and 50 µl of diluted (1:1000) alkaline phosphatase (AP)-conjugated goat-antihuman IgG (Zymed) was added to each well. Plates were incubated for 1.5 hours at room temperature, washed and 50 µl of substrate solution [p-nitrophenyl phosphate (PNPP)/0.1M Tris pH 9.6] was added and plates were incubated at room temperature for 30-60 minutes. Absorbance values at 450 nm were determined for each well.

Figure 3:
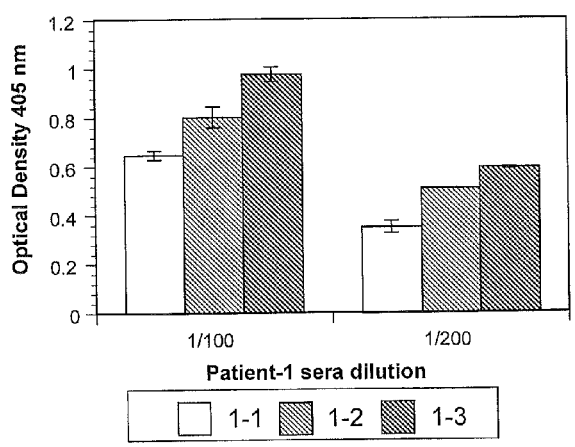
FIGS. 3A-B show an ELISA and an immunoblot employing rD1 as antigen that demonstrates production of anti-CARDS antibodies in sequential serum samples of two patients infected with *Mycoplasma pneumoniae*.
Figure 3:
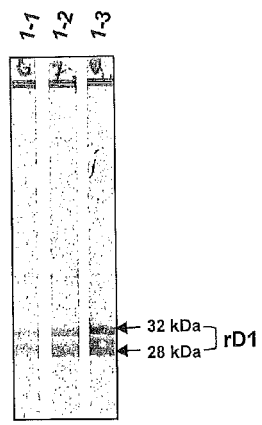
Figure 3:
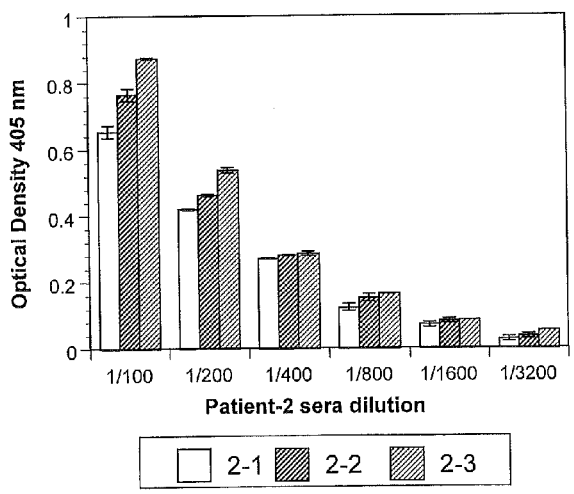
Figure 3:
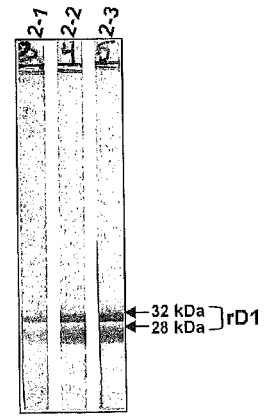

The results for patient 1 with serum dilutions of 1/100 and 1/200 and rD1 as the antigen showed a decrease in optical density at the greater dilution of serum and a stepwise increase in optical density in the samples collected sequentially during the course of disease (i.e., 1-1<1-2<1-3) (FIG. 3A). This stepwise increase correlates with the increased color intensity observed with these serum samples in the immunoblot assay (FIG. 3A). Similar results were obtained with sequential serum samples from patient 1 when rCARDS Toxin was used as the antigen.

The results for patient 2 with serum dilutions of 1/100, 1/200, 1/400, 1/800, 1/1600 and 1/3200 and rD1 as the antigen showed a decrease in optical density as the dilution of serum increased and a stepwise increase in optical density in the samples collected sequentially during the course of disease (i.e., 2-1<2-2<2-3) (FIG. 3B). This stepwise increase correlates with the increased color intensity observed with these serum samples in the immunoblot assay (FIG. 3B). Similar results were obtained with sequential serum samples from patient 2 when rCARDS Toxin was used as the antigen.

Additional studies were conducted wherein each well of an IMMULON 4 HBX Immunoplate (Dynox) was coated overnight at 4° C. with 50 µl of rCARDS toxin (1, 2 or 3 µg/well) diluted in carbonate/bicarbonate buffer. After washing, 50 µl of diluted human serum samples (1/200 dilution of convalescent serum 1-3 as described above) was added to each well and plates were incubated for two hours at room temperature prior to detection of bound IgG. Negative patient serum control was also included. The results showed an optical density around 1.8 and 1.9±SE for all three concentrations of rCARDS toxin and an optical density of the negative control around 0.6 and 0.7±SE for all concentrations of toxin.

A further study was carried out as described above, except that each well of IMMULON 4 HBX Immunoplates (Dynox) was coated overnight at 4° C. with 50 µl of CARDS rD1 domain diluted as follows: 1, 2, 3, 4, 5 or 6 µg/well, in carbonate-bicarbonate buffer. Negative patient serum control was also included. The results show an optical density between 1.0 and 1.2±SE for all six concentrations of rD1 domain and an optical density of the negative control of 0.2±SE or less for all concentrations of rD1.

Overall, these immunoblot and ELISA studies demonstrate that both CARDS toxin and antibodies to CARDS toxin can be detected according to the methods of this invention and that the assays can be performed with as little as 1 µg of toxin either as the recombinant protein or as the D1 domain. These studies also indicate that the D1 domain may be a better target in an ELISA format, with lower background levels.

Identification of *Mycoplasma pneumoniae* by PCR in Sputum Samples Using CARDS Toxin as a Target DNA Molecule In this assay, phosphate buffered saline (PBS), with and without saliva, was mixed with a cell suspension (cells grown 2-3 days at 37° C. in SP-4 medium; total cells ~$1\times10^9$) of *M. pneumoniae* S1 cells in a 1:1 ratio and centrifuged. The pellet was resuspended in 200 μl of water and incubated at 4° C. for 20 minutes. The sample was then boiled at 100° C. for 15 minutes. 37-40 μl of this sample was used for PCR in a total reaction volume of 50 μl. The samples were serially diluted $10^{-1}$ to $10^{-9}$ in PBS. PCR conditions were 95° C. for five minutes; 94° C. for one minute; 55° C. for one minute; 72° C. for one minute and 72° C. for 10 minutes, for 30 cycles. The amplification primer set was Primer 12a forward: (nts. 1197-1220; 24 bp) 5' gcttgttctggaataccaagagtg 3' (SEQ ID NO:23) and Primer 15a reverse: (nts. 1541-1564; 24 bp) 5' ccattctacccaatcccagctgta 3' (SEQ ID NO:26). The product size of the amplicon was 368 base pairs. Detection was by ethidium bromide staining or autoradiography with a $^{32}P$-labeled probe. The probe used to detect the amplicon by autoradiography was Primer 14a forward: (nts 1371-1429; 59 bp) 5' gctggtattggaggggttattactataccccacaattaagtggttggtcttatcagatg 3' (SEQ ID NO:25). Results of this study demonstrate that *M. pneumoniae* nucleic acid can be detected in the presence or absence of saliva and that one mycoplasma cell can be identified using this primer/probe set.

Cloning and Sequencing of CARDS

Based on the published genome sequence of *M. pneumoniae* M129/B9 (Himmelreich et al., 1996, SEQ ID NO:7), the complete open reading frame of cards was analyzed. Translation of nucleotide sequences to amino acids revealed the existence of eight TGA codons within the coding region of cards. Start and stop codons and the eight intervening TGA codons are indicated in bolded text.

tttttaattt gtaaaatttc attttttaaa aatgccaaat cctgttagat ttgtttaccg tgttgatttg agaagccctg aagaaatttt tgaacatggc ttttcaactt taggtgatgt gagaaatttc tttgaacaca ttctctccac taattttggt agaagctatt ttatttccac ttcagaaaca cccacagcag ctattcgctt ctttggtagc tggttacggg aatatgtacc agagcacccc agaagggctt acttatatga aattcgtgcc gaccaacact tttacaatgc ccgcgccact ggggagaact tgttagattt aatgcgtcaa agacaagtag tatttgactc tggtgatcga gaaatggcac aaatgggaat tagagcttta cgcacttcct ttgcgtatca acgtgaatgg tttaccgatg gtccaattgc agcagctaat gtccgtagtg cttgactagt agatgctgtt cccgttgaac ctggtcatgc tcaccacccg gctggtcgtg ttgtagagac tactagaatt aatgaaccgg aaatgcacaa ccctcattat caagagctgc aaacccaagc caatgatcaa ccatgattgc caacaccagg aatagctact cctgtacatt tatcaattcc -continued

```
ccaagcagct tccgttgctg atgtttcgga aggtacttcc gcttcgctat cgtttgcgtg ccctgattga agtccacctt ctagtaatgg tgaaaatccg ctagacaaat gcattgcgga aaagattgat aactataacc tacaatcctt accacagtac gctagcagtg taaaggaact ggaagataca ccagtatacc taaggggaat taaaacgcaa aaaaccttta tgttacaagc agatccgcaa aataacaatg tcttttggt cgaagtaaac cccaaacaaa agtccagctt tccccaaacc atcttctttt gggatgttta tcaacgaatt tgtctcaagg atttaactgg tgcacaaatc agtctttcgc ttactgcctt tactactcag tatgctggtc agctcaaagt gcaccttagt gttagcgcgg ttaatgccgt gaaccaaaag tgaaaaatga caccgcaaga cattgcaata actcagtttc gggtctcctc tgaactgtta ggtcaaactg aaaatggctt gttctgaaat accaagagtg gtggttcaca acacgatttg tatgtatgtc ctttgaaaaa tccacctagt gatttggaag aattacaaat aattgttgat gaatgtacta cccatgcgca gtttgttact atgcgtgcag ctagcacctt ctttgttgat gttcagctag gctggtattg aaggggttat tactataccc cacaattaag tggttgatct tatcagatga aaacaccaga tggacagata ttctatgatc taaaaacttc gaaaatcttc tttgtccagg acaaccaaaa cgtgttcttt ctccataata aactcaacaa acaaactggt tacagctggg attgagtaga atggctaaaa catgacatga atgaggacaa agacgaaaac tttaaatggt acttttcgcg tgatgacctt accattcctt ccgttgaagg gcttaacttc cgccacattc gctgttacgc tgacaaccag cagttaaagg tgatcataag cggttcacgt tggggcggtt ggtactccac ttacgataaa gttgaaagta atgtcgaaga taagattttg gtcaaagatg gttttgatcg cttttagcga ttaagcttta acgtcactgt tttgctctaa tgttagaagc aaagatcttg
```

The entire cards sequence was amplified using forward primer 5'-tttttacatatgccaaatcctgtt-3' (primer 1, SEQ ID NO:12) and reverse primer 5'-gatcgatttagcgaggatccttaacg-3' (primer 2, SEQ ID NO:64), which produces NdeI and BamHI (underlined) sites at 5' and 3' ends of the cards ORF, respectively. Both fragments were ligated into the pCR 2.1 vector and transformed into E. coli INVaF' cells for automated sequencing using M13 forward and reverse primers.

Site-directed mutagenesis of the cards gene to permit expression of total recombinant CARDS protein was necessary, which required the correction of TGAs to TGGs in order to encode tryptophan in E. coli. Therefore, specific primers were designed as indicated below. Primers below are also used to generate specific CARDS domains for generating specific antibody probes.

CARDS: Oligonucleotide Sequences within Selected (above) Nucleotide Sequence.

Pri 1-16: Modified oligonucleotide sequence* to amplify the cards sequence. * modified nucleotides are given in bold. Complementary oligonucleotide sequence are given underneath the reverse primers (2, 3, 5, 7, 9, 11, 13 and 15)

MPN372: 23 tttttaaaaatgccaaatcctgtt 46 (SEQ ID NO: 28)
Pri-1: 1 tttttacatatgccaaatcctgtt 24 (SEQ ID NO: 12)

MPN372: 458 aatgtccgtagtgcttgact 477 (SEQ ID NO: 29)
Pri-3: 20 aatgtccgtagtgcttggct 1 (SEQ ID NO: 30)
ttacaggcatcacgaaccga (SEQ ID NO: 31)

MPN372: 469 tgcttgactagtagatgctgtt 490 (SEQ ID NO: 32)
Pri-4: 1 tgcttggctagtagatgctgtt 22 (SEQ ID NO: 33)

MPN372: 613 atgattgccaacaccagg 630 (SEQ ID NO: 34)
Pri-5: 18 atggttgccaacaccagg 1 (SEQ ID NO: 35)
taccaacggttgtggtcc (SEQ ID NO: 36)

MPN372: 610 accatgattgccaacacc 627 (SEQ ID NO: 37)
Pri-6: 1 accatggttgccaacacc 18 (SEQ ID NO: 38)

MPN372: 722 cctgattgaagtccacctt 740 (SEQ ID NO: 39)
Pri-7: 19 cctgattggagtccacctt 1 (SEQ ID NO: 40)
ggactaacctcaggtggaa (SEQ ID NO: 41)

MPN372: 717 cgtgccctgattgaagtc 734 (SEQ ID NO: 42)
Pri-8: 1 cgtgccctgattggagtc 18 (SEQ ID NO: 43)

MPN372: 1117 aaagtgaaaaatgacaccge 1136 (SEQ ID NO: 44)
Pri-9: 20 aaagtggaaaatgacaccge 1 (SEQ ID NO: 45)
tttcaccttttactgtggcg (SEQ ID NO: 46)

-continued

```
MPN372:  1115  caaaagtgaaaaatgacacc  1134   (SEQ ID NO: 47)
Pri-10:     1  caaaagtggaaaatgacacc    20   (SEQ ID NO: 48)

MPN372:  1192  aaatggcttgttctgaaatacc  1213  (SEQ ID NO: 49)
Pri-11:    22  aaatggcttgttctggaatacc     1  (SEQ ID NO: 50)
               tttaccgaacaagaccttatgg        (SEQ ID NO: 22)

MPN372:  1197  gcttgttctgaaataccaagagt  1219 (SEQ ID NO: 51)
Pri-12:     1  gcttgttctggaataccaagagt    23 (SEQ ID NO: 52)

MPN372:  1368  taggctggtattgaaggggt  1387   (SEQ ID NO: 53)
Pri-13:    20  taggctggtattggaggggt     1   (SEQ ID NO: 54)
               atccgaccataacctcccca          (SEQ ID NO: 55)

MPN372:  1374  ggtattgaaggggttattactataccccacaattaagtggttgatcttatcagatg  1429
Pri-14:     1  ggtattggaggggttattactataccccacaattaagtggttgtcttatcagatg      56  (SEQ ID NOS: 56 and 57)

MPN372:  1541  tacagctgggattgagtagaa  1561  (SEQ ID NO: 58)
Pri-15:    21  tacagctgggattgggtagaa     1  (SEQ ID NO: 59)
               atgtcgaccctaacccatctt         (SEQ ID NO: 60)

MPN372:  1541  tacagctgggattgagtagaa  1561  (SEQ ID NO: 61)
Pri-16:     1  tacagctgggattgggtagaa    21  (SEQ ID NO: 62)

MPN372:  1796  gatcgcttttagcgattaagctttaacg  1824  (SEQ ID NO: 63)
Pri-2:     28  gatcgcttttagcgaggatcctttaacg     1  (SEQ ID NO: 64)
               ctagcgaaaatcgctcctaggaaattgc         (SEQ ID NO: 13)
```

Sequence of *M. pneumoniae* CARDS.

The cards gene of *M. pneumoniae* reference strain M129/B9 and clinical isolates (S1, L2, JL and RJL1) were cloned in a PCRII vector individually and sequenced.

M129/B9 represents the reference strain and S1, L2, RJL1 and JL are clinical isolates from patients in San Antonio and Dallas.

All clinical isolates have the same mutation at nucleotide $1112^{(T \to G)}$ from the ATG start codon, which differs from the published reference strain. However, in clinical isolate S1 three additional nucleotide changes occur at nucleotide base positions $113^{(T \to C)}$, $922^{(T \to C)}$ and $1172^{(T \to C)}$.

The following nucleotide changes were detected in the other clinical isolates:

L2: $734^{(A \to G)}$ and $1112^{(T \to G)}$.
JL: $1112^{(T \to G)}$.
RJL1: $1112^{(T \to G)}$ and $1174^{(T \to C)}$.

Coding Sequence of S1 (*Mycoplasma pneumoniae* Clinical Isolate)

Bolded gs shown were introduced by site directed mutagenesis in order to express CARDS protein in *E. coli*.

```
S1 Nucleotide sequence
                                                          (SEQ ID NO: 8)
atgccaaatc ctgttagatt tgtttaccgt gttgatttga gaagccctga agaaatttt    60 gaacatggct tttcaacttt aggtgatgtg agaaatttct ttgaacacat tccctccact  120
aattttggta gaagctattt tatttccact tcagaaacac ccacagcagc tattcgcttc  180
tttggtagct ggttacggga atatgtacca gagcacccca gaagggctta cttatatgaa  240
attcgtgccg accaacactt ttacaatgcc cgcgccactg gggagaactt gttagattta  300
atgcgtcaaa gacaagtagt atttgactct ggtgatcgag aaatggcaca atgggaatt   360 agagctttac gcacttcctt tgcgtatcaa cgtgaatggt ttaccgatgg tccaattgca  420
gcagctaatg tccgtagtgc ttggctagta gatgctgttc ccgttgaacc tggtcatgct  480
caccacccgg ctggtcgtgt tgtagagact actagaatta atgaaccgga aatgcacaac  540
cctcattatc aagagctgca aacccaagcc aatgatcaac catggttgcc aacaccagga  600
atagctactc ctgtacattt atcaattccc caagcagctt ccgttgctga tgtttcggaa  660
ggtacttccg cttcgctatc gtttgcgtgc cctgattgga gtccaccttc tagtaatggt  720
gaaaatccgc tagacaaatg cattgcggaa aagattgata actataacct acaatcctta  780
ccacagtacg ctagcagtgt aaaggaactg gaagatacac cagtatacct aagggaatt   840 aaaacgcaaa aaacctttat gttacaagca gatccgcaaa ataacaatgt ctttttggtc  900
gaagtaaacc ccaaacaaaa gcccagcttt ccccaaacca tcttcttttg ggatgtttat  960
caacgaattt gtctcaagga tttaactggt gcacaaatca gtctttcgct tactgccttt 1020
actactcagt atgctggtca gctcaaagtg caccttagtg ttagcgcggt taatgccgtg 1080
```

```
                                  -continued
aaccaaaagt ggaaaatgac accgcaagac agtgcaataa ctcagtttcg ggtctcctct 1140
gaactgttag gtcaaactga aaatggcttg tcctggaata ccaagagtgg tggttcacaa 1200
cacgatttgt atgtatgtcc tttgaaaaat ccacctagtg atttggaaga attacaaata 1260
attgttgatg aatgtactac ccatgcgcag tttgttacta tgcgtgcagc tagcaccttc 1320
tttgttgatg ttcagctagg ctggtattgg aggggttatt actataccc acaattaagt 1380 ggttggtctt atcagatgaa acaccagatg gacagatat tctatgatct aaaaacttcg 1440
aaaatcttct ttgtccagga caccaaaac gtgttctttc tccataataa actcaacaaa 1500
caaactggtt acagctggga ttgggtagaa tggctaaaac atgacatgaa tgaggacaaa 1560
gacgaaaact ttaaatggta cttttcgcgt gatgacctta ccattccttc cgttgaaggg 1620
cttaacttcc gccacattcg ctgttacgct gacaaccagc agttaaaggt gatcataagc 1680
ggttcacgtt ggggcggttg gtactccact tacgataaag ttgaaagtaa tgtcgaagat 1740
aagattttgg tcaaagatgg ttttgatcgc ttt                              1773
```

Below are the amino acid sequences of individual clinical isolates.

```
JL
                                                      (SEQ ID NO: 3)
MPNPVRFVYR VDLRSPEEIF EHGFSTLGDV RNFFEHILST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN

PHYQELQTQA NDQPWLPTPG IATPVHLSIP QAASVADVSE GTSASLSFAC PDWSPPSSNG

ENPLDKCIAE KIDNYNLQSL PQYASSVKEL EDTPVYLRGI KTQKTFMLQA DPQNNNVFLV

EVNPKQKSSF PQTIFFWDVY QRICLKDLTG AQISLSLTAF TTQYAGQLKV HLSVSAVNAV

NQKWKMTPQD SAITQFRVSS ELLGQTENGL FWNTKSGGSQ HDLYVCPLKN PPSDLEELQI

IVDECTTHAQ FVTMRAASTF FVDVQLGWYW RGYYYTPQLS GWSYQMKTPD GQIFYDLKTS

KIFFVQDNQN VFFLHNKLNK QTGYSWDWVE WLKHDMNEDK DENFKWYFSR DDLTIPSVEG

LNFRHIRCYA DNQQLKVIIS GSRWGGWYST YDKVESNVED KILVKDGFDR F*
RJL1
                                                      (SEQ ID NO: 4)
MPNPVRFVYR VDLRSPEEIF EHGFSTLGDV RNFFEHILST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN

PHYQELQTQA NDQPWLPTPG IATPVHLSIP QAASVADVSE GTSASLSFAC PDWSPPSSNG

ENPLDKCIAE KIDNYNLQSL PQYASSVKEL EDTPVYLRGI KTQKTFMLQA DPQNNNVFLV

EVNPKQKSSF PQTIFFWDVY QRICLKDLTG AQISLSLTAF TTQYAGQLKV HLSVSAVNAV

NQKWKMTPQD SAITQFRVSS ELLGQTENGL FRNTKSGGSQ HDLYVCPLKN PPSDLEELQI

IVDECTTHAQ FVTMRAASTF FVDVQLGWYW RGYYYTPQLS GWSYQMKTPD GQIFYDLKTS

KIFFVQDNQN VFFLHNKLNK QTGYSWDWVE WLKHDMNEDK DENFKWYFSR DDLTIPSVEG

LNFRHIRCYA DNQQLKVIIS GSRWGGWYST YDKVESNVED KILVKDGFDR F*
L2
                                                      (SEQ ID NO: 5)
MPNPVRFVYR VDLRSPEEIF EHGFSTLGDV RNFFEHILST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN
```

-continued

```
PHYQELQTQA NDQPWLPTPG IATPVHLSIP QAASVADVSE GTSASLSFAC PDWSPPSSNG

ENPLGKCIAE KIDNYNLQSL PQYASSVKEL EDTPVYLRGI KTQKTFMLQA DPQNNNVFLV

EVNPKQKSSF PQTIFFWDVY QRICLKDLTG AQISLSLTAF TTQYAGQLKV HLSVSAVNAV

NQKWKMTPQD SAITQFRVSS ELLGQTENGL FWNTKSGGSQ HDLYVCPLKN PPSDLEELQI

IVDECTTHAQ FVTMRAASTF FVDVQLGWYW RGYYYTPQLS GWSYQMKTPD GQIFYDLKTS

KIFFVQDNQN VFFLHNKLNK QTGYSWDWVE WLKHDMNEDK DENFKWYFSR DDLTIPSVEG

LNFRHIRCYA DNQQLKVIIS GSRWGGWYST YDKVESNVED KILVKDGFDR F*

S1                                                    (SEQ ID NO: 2)
MPNPVRFVYR VDLRSPEEIF EHGFSTLGDV RNFFEHIPST NFGRSYFIST SETPTAAIRF

FGSWLREYVP EHPRRAYLYE IRADQHFYNA RATGENLLDL MRQRQVVFDS GDREMAQMGI

RALRTSFAYQ REWFTDGPIA AANVRSAWLV DAVPVEPGHA HHPAGRVVET TRINEPEMHN

PHYQELQTQA NDQPWLPTPG IATPVHLSIP QAASVADVSE GTSASLSFAC PDWSPPSSNG

ENPLDKCIAE KIDNYNLQSL PQYASSVKEL EDTPVYLRGI KTQKTFMLQA DPQNNNVFLV

EVNPKQKPSF PQTIFFWDVY QRICLKDLTG AQISLSLTAF TTQYAGQLKV HLSVSAVNAV

NQKWKMTPQD SAITQFRVSS ELLGQTENGL SWNTKSGGSQ HDLYVCPLKN PPSDLEELQI

IVDECTTHAQ FVTMRAASTF FVDVQLGWYW RGYYYTPQLS GWSYQMKTPD GQIFYDLKTS

KIFFVQDNQN VFFLHNKLNK QTGYSWDWVE WLKHDMNEDK DENFKWYFSR DDLTIPSVEG

LNFRHIRCYA DNQQLKVIIS GSRWGGWYST YDKVESNVED KILVKDGFDR F*
```

These sequence data are summarized below.
1. Translation of the nucleotide sequence of the clinical isolates showed changes in amino acid positions at 38, 245, 308, 371, 391 and 392.
2. All the clinical isolates have changes at amino acid position $371^{Ile \to Ser}$.
3. JL had only one change at aa position $371^{Ile \to Ser}$.
4. RJL1 had one more additional change (comparing to JL) at aa position $392^{Trp \to Arg}$.
5. L2 had one more additional change (comparing to JL) at aa position $245^{Asp \to Gly}$.
6. S1 had three additional changes (comparing to JL) at aa positions $38^{Leu \to Pro}$, $308^{Ser \to Pro}$ and $391^{Phe \to Ser}$.

Expression and Purification of Recombinant CARDS Protein.

DNA fragments were generated by digesting plasmid pCR-cards with NdeI and BamHI and ligated into pET19b to generate pET-cards. The plasmid was transformed into competent E. coli BL21 (DE3) cells grown to a density of $2 \times 10^9$ cells/ml at 37° C. in standard LB broth containing 100 µg/ml ampicillin (Sigma-Aldrich). Induction of recombinant protein synthesis was accomplished by addition of 100 µM of isopropyl thio β-galactopyranoside (Sigma-Aldrich), and bacteria were incubated for 3 h at 37° C. under aeration at 220 rpm. Cells from 1 ml samples were pelleted, resuspended in 250 µl of sample buffer (4% SDS, 125 mM Tris [pH 6.8], 10% □-ME, 10% glycerol, 0.2% bromophenol blue), and heated to 95° C. for 5 min. 10 µl aliquots of test samples were analyzed on 12% SDS/polyacrylamide gels. Recombinant colonies were screened for resistance to ampicillin and expression of a protein product of the correct size, and one recombinant clone from each construct was selected for further study. Verification of specific clones was achieved by restriction digestion and limited DNA sequencing. Fusion proteins were purified from recombinant E. coli under native condition by nickel affinity chromatography using the manufacturer's protocol (Qiagen).

Preparation of Antisera Against Recombinant Mycoplasma Proteins.

Mice were immunized subcutaneously with 50-100 µg of recombinant total CARDS protein suspended in complete Freund's adjuvant (no peptides or truncated domains). Individual mice were boosted three times with the same amount of recombinant antigen in incomplete Freund's adjuvant at 14-day intervals. Serum samples were collected and used for immunological characterization. Monoclonal antibodies were produced using recombinant CARDS toxin and hybridoma supernatants were screened for immunoreactivity with CARDS protein and truncated peptides.

Full length recombinant CARDS Toxin (rTOX) and the amino terminal D1 domain of recombinant CARDS Toxin (rD1) were separated on 4-12% preparative gels, transferred to nitrocellulose and reacted with various concentrations (1:2, 1:10 and 1:50 or 1:100) of primary mouse antibodies against rTOX or rD1 (Monoclonal antibodies 11D1-2H10, isotype 1gGg1 and monoclonal antibody 19C4-2G10-1E1-2B9, isotype IgG3). Membranes were washed and reacted with alkaline phosphatase-conjugated goat anti-mouse IgG. Blots were washed again, followed by color development with NBT-BCIP reagent. Both antibodies bound a protein of approximately 70 kDa MW in membranes containing rTOX and both antibodies bound peptides of 28 kDa MW and 32 kDa MW in membranes containing rD1.

Primers Designed to Express Specific Domains of CARDS

Introduced restriction sites are indicated by underline. Changes in nucleotide sequences are given in bold.

| | | |
|---|---|---|
| tttttacatatgccaaatcctgtt | Primer 1 | (SEQ ID NO: 12) |
| tttttacatatgccaaatcctgttag | Primer 1a | (SEQ ID NO: 72) |
| ggatcctctacgcaatgcatttgtctag | 372D1R | (SEQ ID NO: 65) |
| catatgccaacaccaggaatagctactc | 372D2F | (SEQ ID NO: 66) |
| ggatccactaccagcctagctgaac . . . | 372D2R | (SEQ ID NO: 67) |
| catatgggtcagctcaaagtgcaccttag | 372D3F | (SEQ ID NO: 68) |
| gatcgcttttagcgaggatcctttaacg | Primer 2 | (SEQ ID NO: 64) |

Amplified region of CARDS toxin nucleic acid encoding D1

(SEQ ID NO: 74)

```
1 atgccaaatc ctgttagatt tgtttaccgt gttgatttga aagccctga agaaatttt    60
  gaacatggct tttcaacttt aggtgatgtg agaaatttct tgaacacat tctctccact   120
  aattttggta aagctatttt tatttccact tcagaaacac ccacagcagc tattcgcttc   180
  tttggtagct ggttacggga atatgtacca gagcaccca aagggctta cttatatgaa    240
  attcgtgccg accaacactt ttacaatgcc cgcgccactg gggagaactt gttagattta   300
  atgcgtcaaa gacaagtagt atttgactct ggtgatcgag aaatggcaca atgggaatt    360
  agagctttac gcacttcctt tgcgtatcaa cgtgaatggt ttaccgatgg tccaattgca   420
  gcagctaatg tccgtagtgc ttggctagta gatgctgttc ccgttgaacc tggtcatgct   480
  caccacccgg ctggtcgtgt tgtagagact actagaatta atgaaccgga aatgcacaac   540
  cctcattatc aagagctgca aacccaagcc aatgatcaac catggttgcc aacaccagga   600
  atagctactc ctgtacattt atcaattccc caagcagctt ccgttgctga tgtttcggaa   660
  ggtacttccg cttcgctatc gtttgcgtgc cctgattgga gtccaccttc tagtaatggt   720
  gaaaatccgc tagacaaatg cattgcg                                       747
```

Domains Expected to be Expressed in *E. coli* Using the above Primers.

Overlapping amino acids within domains are indicated by underline.

```
Domain 1:
Primer 1 and 372D1R
                                                      (SEQ ID NO: 69)
    1 MPNPVRFVYR VDLRSPEEIF EHGFSTLGDV RNFFEHILST NFGRSYFIST
   51 SETPTAAIRF FGSWLREYVP EHPRRAYLYE IRADQHFYNA RATGENLLDL
  101 MRQRQVVFDS GDREMAQMGI RALRTSFAYQ REWFTDGPIA AANVRSAWLV
  151 DAVPVEPGHA HHPAGRVVET TRINEPEMHN PHYQELQTQA NDQPWLPTPG
  201 IATPVHLSIP QAASVADVSE GTSASLSFAC PDWSPPSSNG ENPLDKCIA
      Theoretical pI/Mw: 5.54/28127.37

Domain 1 with His tag (underlined)
                                                      (SEQ ID NO: 75)
      MGHHHHHHHHHHSSGHIDDDDKH
    1 MPNPVRFVYR VDLRSPEEIF EHGFSTLGDV RNFFEHILST NFGRSYFIST
   51 SETPTAAIRF FGSWLREYVP EHPRRAYLYE IRADQHFYNA RATGENLLDL
  101 MRQRQVVFDS GDREMAQMGI RALRTSFAYQ REWFTDGPIA AANVRSAWLV
  151 DAVPVEPGHA HHPAGRVVET TRINEPEMHN PHYQELQTQA NDQPWLPTPG
  201 IATPVHLSIP QAASVADVSE GTSASLSFAC PDWSPPSSNG ENPLDKCIA
      Theoretical pI/Mw with the tag: 5.95/30894.20
Domain 2:
372D2F and 372D2R
                                                      (SEQ ID NO: 70)
      PWLPTPG
  201 IATPVHLSIP QAASVADVSE GTSASLSFAC PDWSPPSSNG ENPLDKCIAE
  251 KIDNYNLQSL PQYASSVKEL EDTPVYLRGI KTQKTFMLQA DPQNNNVFLV
```

```
301 EVNPKQKSSF PQTIFFWDVY QRICLKDLTG AQISLSLTAF TTQYAGQLKV

351 HLSVSAVNAV NQKWKMTPQD IAITQFRVSS ELLGQTENGL FWNTKSGGSQ

401 HDLYVCPLKN PPSDLEELQI IVDECTTHAQ FVTMRAASTF FVDVQLGWY
    Theoretical pI/Mw: 5.05/28378.10

Domain 3:
372D3F and Primer 2
                                                  (SEQ ID NO: 71)
    AGQLKV
351 HLSVSAVNAV NQKWKMTPQD IAITQFRVSS ELLGQTENGL FWNTKSGGSQ

401 HDLYVCPLKN PPSDLEELQI IVDECTTHAQ FVTMRAASTF FVDVQLGWYW

451 RGYYYTPQLS GWSYQMKTPD GQIFYDLKTS KIFFVQDNQN VFFLHNKLNK

501 QTGYSWDWVE WLKHDMNEDK DENFKWYFSR DDLTIPSVEG LNFRHIRCYA

551 DNQQLKVIIS GSRWGGWYST YDKVESNVED KILVKDGFDR F
    Theoretical pI/Mw: 5.69/28966.52
```

Production of Recombinant N Terminal Domain of CARDS Toxin rD1

To produce rD1, the D1 PCR fragment (SEQ ID NO:74) encoding the cards first 249 amino acids (SEQ ID NO:69) was cloned into the *E. coli* His[10]-tagged expression vector, pET19b (Novagen), using NdeI and BamHI restriction sites incorporated into the oligonucleotide primers used to amplify this nucleic acid 5' tUttacatatgccaaatectgttag 3' (SEQ ID NO:72) and 5' ggatectctacgcaatgcatttgtetag 3' (SEQ ID NO:65). Because the NdeI site in the vector overlaps an ATG start codon, cloning the D1 fragment into this site places the fragment in perfect register with the vector-derived His-tagged ribosome binding site. The amino acid sequence of the expressed protein with the His tag is shown in SEQ ID NO:75.

After cloning the D1 PCR fragment into pET19b and confirming the identify of the cloned fragment by DNA sequencing, a recombinant plasmid was used to transform *E. coli* strain BL21 (λDE3). Transformants were grown to mid-log phase before inducing D1 expression by addition of IPTG to a final concentration of 1 mM. After four hours, cells were harvested by centrifugation at 8000 g for 15 minutes at 4° C. and the pellet was resuspended in 50 mM phosphate buffer ph 8.0, containing 300 mM NaCl, 10 in M imidazole and complete, EDTA-free protease inhibitor (Sigma). Cells were disrupted by sonication; cellular debris and membranes were pelleted by centrifugation at 16000 g for 30 minutes and discarded; the supernatant was mixed with Ni-NTA agarose slurry and left on a rocker at room temperature for one hour; and then the slurry was loaded into a column. The Ni-NTA agarose packed column was extensively washed with 10 mM imidazole, 20 mM imidazole, and 50 mM imidazole in the same buffer used for pellet resuspension. Finally, D1 was purified in a single step elution with 250 mM imidazole in the same buffer. Fractions containing purified protein were desalted using P10 columns (Amersham Biosciences) with TG buffer (20 mM Tris-C1, pH 7.4, 5% glycerol) and concentrated using YM-10 (Amicon) membranes. Protein concentrations were estimated using a BCA protein assay kit (Pierce) and the protein was aliquoted and stored at −80° C.

Cytopathology in Chinese Hamster Ovary (CHO) Cells

Cells were seeded into 25 cm² cell culture flasks and incubation was continued until monolayer confluence was achieved. Then, recombinant CARDS protein (20 μg/ml or 40 μg/ml) was added for 24 hours. Monolayers were photographed on an Olympus CK40 microscope at 20× magnification.

In CHO cells, the recombinant toxin causes cytopathology with an associated "foamy" appearance, rounding of cells and cell detachment from monolayers.

Figure 2:
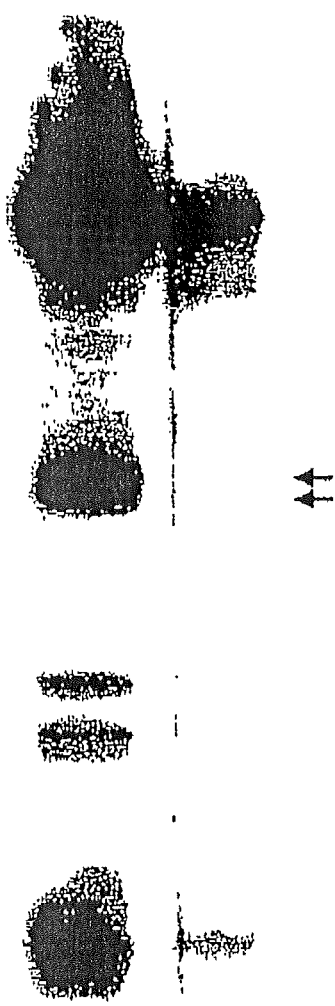
FIG. 2 shows ADP-ribosylation of G proteins in HEp-2 cells following incubation with CARDS protein. Lane 1: HEp-2 cells in medium alone followed by preparation of cell free extract and addition of CARDS protein. Lane 2: HEp-2 cells pretreated with CARDS protein, followed by preparation of cell free extract and addition of CARDS protein. The marked reduction in ADP-ribosylation of specific proteins in the CARDS protein-pretreated cells is indicated by arrows.; Also, ADP-ribosylation of other Hep-2 cell proteins is diminished (lane 2).

ADP-Ribosylation of G Proteins Following Incubation of Cards Protein with HEp-2 Cells Confluent HEp-2 cells were incubated with medium alone or in the presence of 40 μg/ml CARDS protein for 16 hours at 37° C. Cells were washed and incubated with fresh medium at 37° C. for four hours. Cell free extracts (CFE) were prepared and assayed for ADP-ribosylation (CFE were incubated with 40 μg/ml CARDS protein for one hour with 0.1 μM [$^{32}$P]NAD in 100 mM Tris pH 7.5, 20 mM DTT). The reaction mixture was precipitated with 10% TCA and proteins were resolved in a 4-15% gradient gel by SDS-PAGE and transferred to nitrocellulose membrane for autoradiography. As shown in the autoradiogram in FIG. 2, the CARDS exotoxin exhibits ADP ribosylating activity.

Animal Model of *M. pneumoniae* Infection

Sera from mice infected with *M. pneumoniae* have been shown to seroconvert to the CARDS toxin. These mice will be used as an animal model to further assess the role of the CARDS Toxin in infection and disease progression.

Summary of Antibody Studies

*Mycoplasma pneumoniae* (Mp) is the causative agent of acute and chronic respiratory infections and accounts for 20-30% of community acquired pneumonia. *Mycoplasma pneumoniae* is the etiologic agent of primary atypical pneumonia and is also associated with exacerbation of chronic obstructive pulmonary disease and extrapulmonary manifestations. CARDS (Community Acquired Respiratory Distress Syndrome) toxin is a unique virulence determinant of *M. pneumoniae* that exhibits both ADP ribosylating and vacuolating activities. This toxin causes pulmonary inflammation and airway dysfunction after binding and entering airway epithelial cells, similar to that observed during *M. pneumoniae* infection in humans.

Figure 4:
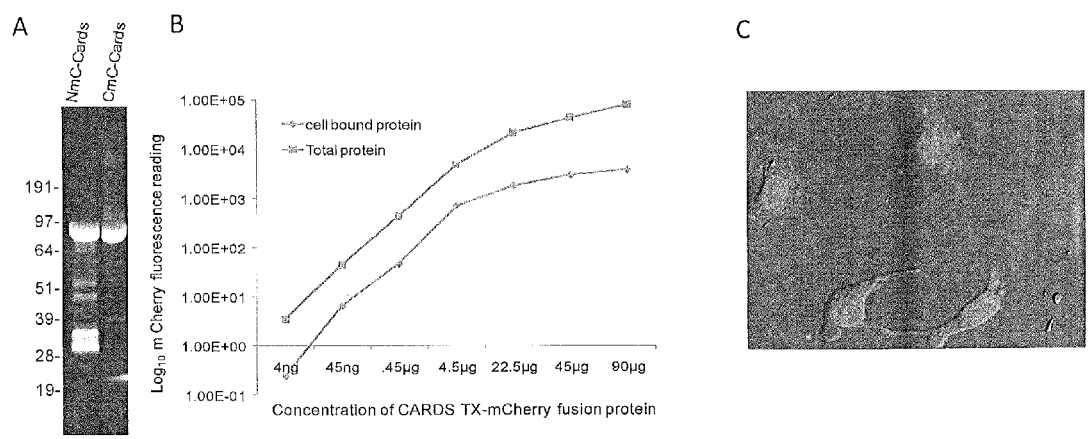
FIGS. 4A-C show the characterization of mCherry coupled CARDS toxin binding. A) Fluorescence of mCherry conjugated CARDS toxin on UV-transilluminator. mCherry conjugated at amino terminal (NmC-CARDS) of CARDS toxin and coupled at carboxyl regions of CARDS toxin (CmC-CARDS). B). Fluorescence of total versus bound CmC-CARDS toxin. C) Direct fluorescence image of CmC-CARDS toxin binding to A549 cells fixed and DAPI stained.
Figure 6:
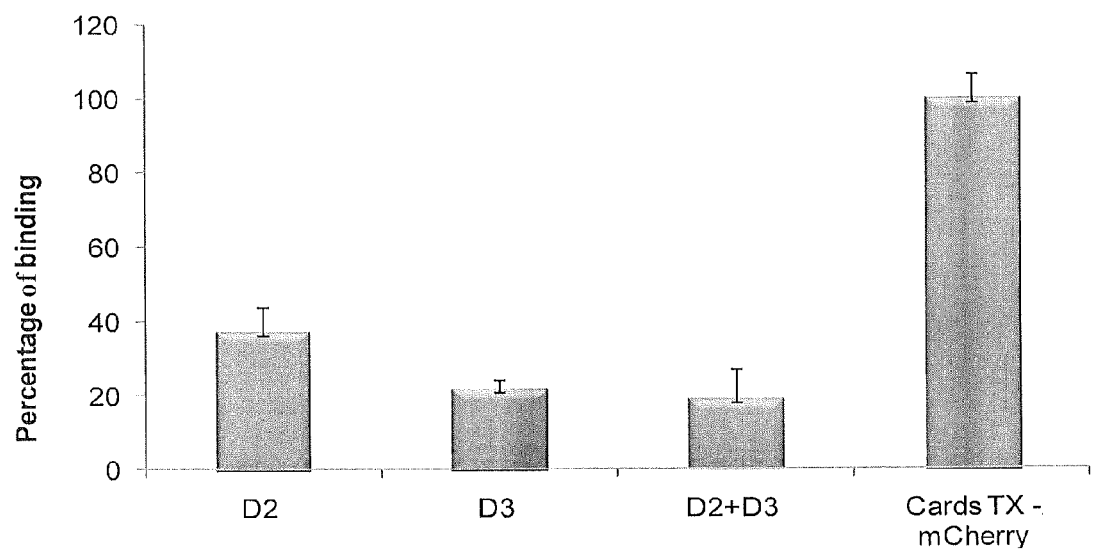
FIG. 6 shows binding of CARDS toxin (CmC-CARDS) to HeLa cells in the presence of anti-CARDS toxin monoclonal antibodies. CARDS TX tagged with mCherry was incubated with monoclonal antibodies for 10 minutes at room temperature, prior to addition to HeLa cells at 4° C. for 30 minutes. Monolayers were washed with PBS three times to remove unbound toxin, and mCherry fluorescence was measured. Values show the percentage of binding in triplicate wells±S.D. Note monoclonal antibody blocking by D2 and D3 (amino acid epitopes are described herein).
Figure 7:
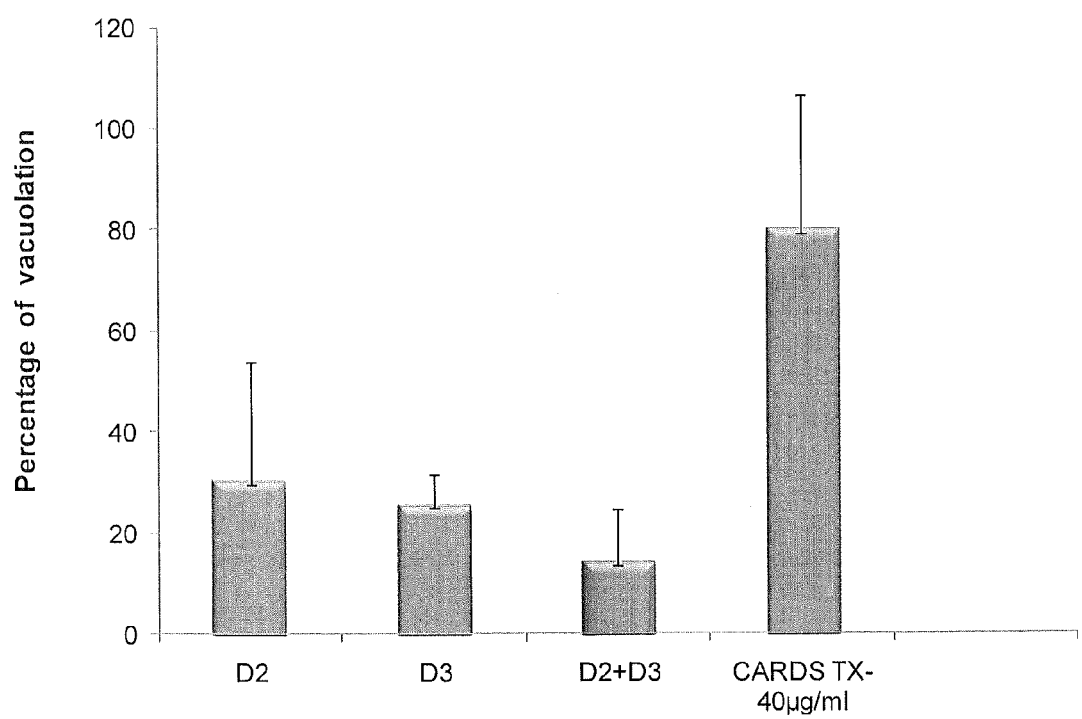
FIG. 7 shows neutralization of vacuolization by monoclonal antibodies. Monoclonal antibodies were mixed with purified rCARDS toxin and incubated at room temperature for 10 minutes prior to addition to HeLa cells. After incubation for 24 h at 37° C., vacuolation was quantitated by neutral red uptake. Values show the percentage of vacuolation in triplicate wells±S.D.
Figure 9A:
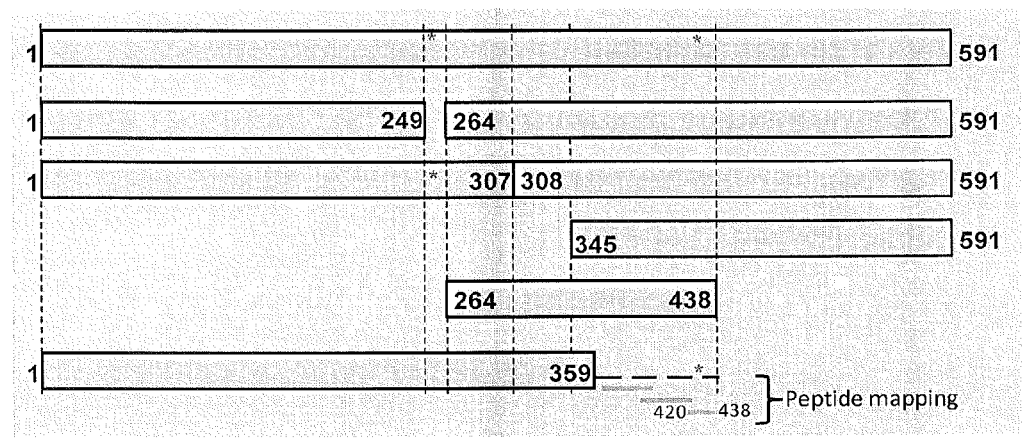
FIGS. 9A-B show epitope mapping of antibodies that block the binding of CARDS toxin to mammalian cells, A). Based on immunoreactivity of the mAbs, the epitope regions of CARDS toxin that are recognized by the monoclonal antibodies were identified using truncated proteins and by partial peptide array. B) Direct fluorescence image of toxin blocked by M713A9. Binding of CmC-CARDS to A549 cells. Binding of CmC-CARDS to A549 cells after treating with non-specific antibody (left panel) or M713A9 (D2 monoclonal antibody, right panel). Note absence of toxin binding and internalization (no red staining) on right.
Figure 9B:
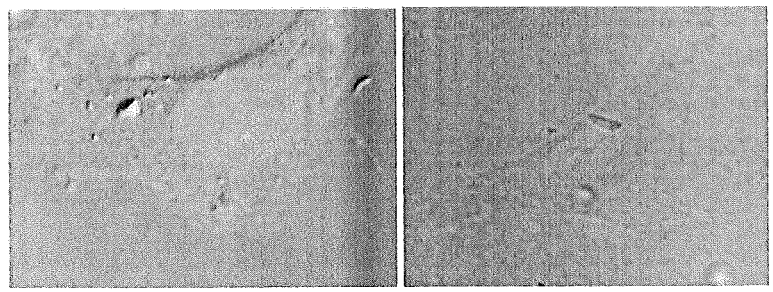

In the studies described below, monoclonal antibodies against full length and truncated CARDS toxin-related proteins were generated and analyzed for their neutralizing potential. Among the various CARDS toxin-reactive antibodies tested, two monoclonal antibodies were identified that reduced the binding and vacuolating activities of CARDS toxin by ~80% (FIGS. 6-7). Clearly, the reduction in binding of CARDS toxin to human cells (using the assay described in FIG. 4) directly correlated with markedly diminished vacuolization. The effectiveness of these two monoclonal antibodies is reinforced as shown in FIG. 5, in which rabbit polyclonal antibody generated against full-length CARDS toxin also reduced CARDS toxin binding by ~80%. The two neutralizing monoclonal antibodies were further characterized by epitope mapping using synthetic peptides of CARDS toxin, and the precise amino acid sequences were identified (FIG. 8). These observations are consistent with data presented in FIG. 5 where only rabbit polyclonal antibodies against full-length CARDS toxin (which contains the key CARDS toxin neutralizing epitopes indicated in FIG. 8) were effective in neutralizing CARDS toxin binding and vacuolization (compare FIG. 5 truncated amino acid sequences with FIG. 8 neutralizing epitope sequences). The findings of this study provide tools for understanding the structural and functional properties of CARDS toxin and uncovering small molecule therapeutic and vaccine targets for controlling and preventing *M. pneumoniae*- and CARDS toxin-mediated pathologies.

Expression and Purification of N- and C-Terminal mCherry Conjugated CARDS Toxin and its Binding Properties In order to characterize the antibodies which block/neutralize the binding and internalization of CARDS toxin, CARDS toxin (*M. pneumoniae* exotoxin) was coupled to mCherry fluorescence protein by overlap extension PCR and recombinant CARDS toxin was expressed. To generate the most useful and functional recombinant CARDS toxin protein, mCherry was conjugated individually to the amino terminal (NmC-CARDS) and the carboxyl (CmC-CARDS) regions of CARDS toxin and the CARDS toxin-mCherry conjugate was expressed in *E. coli* BL2; both recombinant proteins exhibited the red color. Upon purification, each protein fluoresced on UV-exposed Nu-PAGE gels; however, the carboxyl coupling (CmC-CARDS) gave stable protein (FIG. 4A, single band). A549 human airway cells grown in 96 well plates (lumino/flourimeter compatible) were examined for the binding of CmC-CARDS toxin. Based on different CmC-CARDS protein concentrations and fluorescence readings, a standard graph was established (FIG. 4B). After specified times of incubation of CmC-CARDS with A549 cells, plates were washed to remove unbound CmC-CARDS, and bound CARDS toxin concentrations were determined by estimating the fluorescence intensity (FIG. 4B). In addition, as shown in FIG. 4C, CmC-CARDS binding to A549 cells was visualized very clearly using direct fluorescence. Altogether, CmC-CARDS can serve to screen and characterize antibodies reactive against CARDS toxin that block/neutralize the binding and internalization of CARDS toxin.

Epitope Mapping of CARDs Toxin Monoclonal Antibodies.

After isotyping individual mAbs, they were screened against different truncations of CARDS toxin. Once initial immunoreactive domains were determined for each monoclonal and polyclonal antibody reagent using ELISA and immunoblots, partial peptide arrays representing specific toxin domains were used to further define epitopes (FIGS. 6 and 8) Also, these antibodies were screened for their blocking/neutralizing activities by specific published assays (FIGS. 6-8). As a result, two monoclonal hybridoma subclones (M713A9 and M108A8) were identified that produced blocking/neutralizing antibodies which epitope mapped between regions aa249-272 (D2; M713A9) and aa421-438 (D3; M108B6). These antibodies (Fab fragments) can be used in co-crystallography studies with CARDS toxin to visualize conformational changes that lead to blocking/neutralizing phenotype.

These studies demonstrate that monoclonal antibodies D2 and D3 specific to CARDS toxin epitopes inhibit CARDS toxin binding to mammalian cells and reduce vacuolating activity. These monoclonal antibodies are useful for therapeutic use and studies (vaccine candidates and drug design) and for structural and functional analyses of CARDS toxin. The identification of neutralizing antibodies that alter the cell binding and vacuolating activities of the CARDS toxin allows for therapeutic approaches to alleviate the pathologic conditions caused by CARDS toxin. Importantly, neutralizing antibodies to these same epitopes have been identified in humans who are convalescing from acute *M. pneumoniae* infections, suggesting that these antibodies interfere with disease progression and are protective.

Generation of an Extensive Repertoire of Monoclonal Antibodies Reactive Against Full-Length and Individual Domains of Cards TX for Further Identification and Characterization of Neutralizing and Blocking Domains.

The studies described above demonstrated the existence of blocking/neutralizing antibodies to CARDS TX domains and allowed for screening for the existence of these specific antibodies in patients who were acutely infected with *M. pneumoniae*-(tracheobronchitis and community acquired pneumonia; i.e., not patients with asthma symptoms), as compared to asthma patients using ELISA and blocking and neutralizing assays. Fifteen acutely infected *M. pneumoniae* patient sera from the repository and 55 asthma patient sera were screened for immunoreactivity to these two blocking/neutralizing domains (D2 and D3). Remarkably, 12/15 acutely infected patient sera possessed high titer antibodies to the CARDS TX 'blocking/neutralizing epitopes' while only 3/55 chronic asthmatics exhibited similar immunoreactivity. This impressive finding indicates that asthmatics may not be able to generate neutralizing antibodies to CARDS toxin, thereby lacking an adequate protective immune response, This effort allows for the following of antibody profiling in patient populations longitudinally and to predict outcomes of susceptibility and progression of airway inflammation in children and adult populations. Subsequent epitope mapping and utilization of the mouse model of infection will assist in further identifying mechanisms of protective immunity.

Panels of monoclonal antibody reagents against individual truncations and overlapping peptides of CARDS toxin will be assembled to expand the identification of neutralizing and blocking domains. These antibodies will be screened, for example, against recombinant CARDS toxin truncations and 17-mer and/or 18-mer overlapping biotinylated CARDS toxin-related peptides as described herein. Biotinylated peptides will improve the selection and screening processes as ELISA wells will be coated with streptavidin, and biotinylated peptides will bind better and with improved conformation. The impact of antibody isotype on neutralization and blocking assays in vitro will be assessed and an examination of how these antibodies reduce inflammation and protection in vivo will be carried out. This will allow for the selection of monoclonal antibodies with the highest neutralizing and blocking ability for detailed CARDS toxin epitope mapping.

Although the present process has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents and publications in their entireties are incorporated by reference into this application in order to more fully describe the state of the art to which this invention pertains.

TABLE 1

| Sequence | SEQ ID NO: |
|---|---|
| MPNPVRFVYRVDLRSPE | 77 |
| VYRVDLRSPEEIFEHGF | 78 |
| SPEEIFEHGFSTLGDVR | 79 |
| HGFSTLGDVRNFFEHIL | 80 |
| DVRNFFEHILSTNFGRS | 81 |
| HILSTNFGRSYFISTSE | 82 |
| GRSYFISTSETPTAAIR | 83 |
| TSETPTAAIRFFGSWLR | 84 |
| AIRFFGSWLREYVPEHPR | 85 |
| WLREYVPEHPRRAYLYE | 86 |
| EHPRRAYLYEIRADQHF | 87 |
| LYEIRADQHFYNARATG | 88 |
| QHFYNARATGENLLDLM | 89 |
| ATGENLLDLMRQRQVVF | 90 |
| DLMRQRQVVFDSGDREM | 91 |
| VVFDSGDREMAQMGIRA | 92 |
| REMAQMGIRALRTSFAY | 93 |
| IRALRTSFAYQREWFTD | 94 |
| FAYQREWFTDGPIAAAN | 95 |
| FTDGPIAAANVRSAWLV | 96 |
| AANVRSAWLVDAVPVEPG | 97 |
| WLVDAVPVEPGHAHHPA | 98 |
| VEPGHAHHPAGRVVETT | 99 |
| HPAGRVVETTRINEPEM | 100 |
| ETTRINEPEMHNPHYQE | 101 |
| PEMHNPHYQELQTQAND | 102 |
| YQELQTQANDQPWLPTPG | 103 |
| ANDQPWLPTPGIATPVH | 104 |
| PTPGIATPVHLSIPQAA | 105 |
| PVHLSIPQAASVADVSE | 106 |
| QAASVADVSEGTSASLS | 107 |
| VSEGTSASLSFACPDWS | 108 |
| SLSFACPDWSPPSSNGE | 109 |
| DWSPPSSNGENPLDKCI | 110 |
| NGENPLDKCIAEKIDNY | 111 |
| KCIAEKIDNYNLQSLPQ | 112 |
| DNYNLQSLPQYASSVKE | 113 |
| LPQYASSVKELEDTPVY | 114 |
| VKELEDTPVYLRGIKTQ | 115 |

TABLE 1-continued

| Sequence | SEQ ID NO: |
|---|---|
| PVYLRGIKTQKTFMLQA | 116 |
| KTQKTFMLQADPQNNNV | 117 |
| LQADPQNNNVFLVEVNPK | 118 |
| NNVFLVEVNPKQKSSFPQ | 119 |
| VNPKQKSSFPQTIFFWD | 120 |
| SFPQTIFFWDVYQRICL | 121 |
| FWDVYQRICLKDLTGAQ | 122 |
| ICLKDLTGAQISLSLTA | 123 |
| GAQISLSLTAFTTQYAG | 124 |
| LTAFTTQYAGQLKVHLS | 125 |
| YAGQLKVHLSVSAVNAV | 126 |
| HLSVSAVNAVNQKWKMT | 127 |
| NAVNQKWKMTPQDIAIT | 128 |
| KMTPQDIAITQFRVSSE | 129 |
| AITQFRVSSELLGQTEN | 130 |
| SSELLGQTENGLFWNTK | 131 |
| TENGLFWNTKSGGSQHD | 132 |
| NTKSGGSQHDLYVCPLK | 133 |
| QHDLYVCPLKNPPSDLE | 134 |
| PLKNPPSDLEELQIIVD | 135 |
| DLEELQIIVDECTTHAQ | 136 |
| IVDECTTHAQFVTMRAA | 137 |
| HAQFVTMRAASTFFVDV | 138 |
| RAASTFFVDVQLGWYWR | 139 |
| VDVQLGWYWRGYYYTPQ | 140 |
| YWRGYYYTPQLSGWSYQ | 141 |
| TPQLSGWSYQMKTPDGQ | 142 |
| SYQMKTPDGQIFYDLKT | 143 |
| DGQIFYDLKTSKIFFVQ | 144 |
| LKTSKIFFVQDNQNVFF | 145 |
| FVQDNQNVFFLHNKLNK | 146 |
| VFFLHNKLNKQTGYSWD | 147 |
| LNKQTGYSWDWVEWLKH | 148 |
| SWDWVEWLKHDMNEDKD | 149 |
| LKHDMNEDKDENFKWYF | 150 |
| DKDENFKWYFSRDDLTI | 151 |
| WYFSRDDLTIPSVEGLN | 152 |
| LTIPSVEGLNFRHIRCY | 153 |

TABLE 1-continued

| Sequence | SEQ ID NO: |
|---|---|
| GLNFRHIRCYADNQQLK | 154 |
| RCYADNQQLKVIISGSR | 155 |
| QLKVIISGSRWGGWYST | 156 |
| GSRWGGWYSTYDKVESN | 157 |
| YSTYDKVESNVEDKILV | 158 |
| ESNVEDKILVKDGFDRF | 159 |
| ILVKDGFDRF | 160 |

TABLE 2

| Amino Acid | | | Codons | | | | |
|---|---|---|---|---|---|---|---|
| Alanine | Ala | A | GCA | GCC | GCG | GCT | |
| Cysteine | Cys | C | TGC | TGT | | | |
| Aspartic acid | Asp | D | GAC | GAT | | | |
| Glutamic acid | Glu | E | GAA | GAG | | | |
| Phenylalanine | Phe | F | TTC | TTT | | | |
| Glycine | Gly | G | GGA | GGC | GGG | GGT | |
| Histidine | His | H | CAC | CAT | | | |
| Isoleucine | Ile | I | ATA | ATC | ATT | | |
| Lysine | Lys | K | AAA | AAG | | | |
| Leucine | Leu | L | TTA | TTG | CTA | CTC | CTG | CTT |
| Methionine | Met | M | ATG | | | | |
| Asparagine | Asn | N | AAC | AAT | | | |
| Proline | Pro | P | CCA | CCC | CCG | CCT | |
| Glutamine | Gln | Q | CAA | CAG | | | |
| Arginine | Arg | R | AGA | AGG | CGA | CGC | CGG | CGT |
| Serine | Ser | S | AGC | ACT | TCA | TCC | TCG | TCT |
| Threonine | Thr | T | ACA | ACC | ACG | ACT | |
| Valine | Val | V | GTA | GTC | GTG | GTT | |
| Tryptophan | Trp | W | TGG | | | | |
| Tyrosine | Tyr | Y | TAC | TAT | | | |

What is claimed is:

1. An isolated monoclonal antibody or fragment thereof that specifically binds an epitope within amino acids 249-272 of SEQ ID NO:1 of *Mycoplasma pneumoniae* exotoxin.

2. The monoclonal antibody of claim 1, coupled to a detectable group.

3. The monoclonal antibody of claim 1, coupled to a therapeutic group.

4. The monoclonal antibody of claim 1, wherein the antibody is humanized.

5. A pharmaceutical formulation comprising the monoclonal antibody of claim 1 in a pharmaceutically acceptable carrier.

* * * * *

UNITED STATES PATENT AND TRADEMARK OFFICE
CERTIFICATE OF CORRECTION

PATENT NO. : 8,586,046 B2
APPLICATION NO. : 13/339866
DATED : November 19, 2013
INVENTOR(S) : Baseman et al.

It is certified that error appears in the above-identified patent and that said Letters Patent is hereby corrected as shown below:

In the Specification
Column 1, Lines 17-19: Delete the paragraph below in its entirety:
"The present invention relates to *Mycoplasma* pneumoniae exotoxins, peptides thereof and antibodies thereto, and their use in diagnostic and therapeutic methods."

Column 22, Line 9: Correct "according to Table"
to read -- according to Table 2. --

Column 45, Lines 46-47:
Correct "or tissue type.
Standard methods are known"
to read as one continuous paragraph as below:
-- or tissue type. Standard methods are known --

Column 55, Line 37: Correct "5'-tttttacatatgccaaatcctgtt-3'"
to read -- 5'-tttttacatatgccaaatcctgtt-3' --

Column 55, Line 38: Correct "5'-gatcgatttagcgaggatccttaacg-3'"
to read -- 5'-gatcgcttttagcgaggatcctttaacg-3' --

Column 55, Item SEQ ID NO: 44:
Correct "MPN372: 1117 aaagtgaaaaatgacaccge 1136 (SEQ ID NO: 44)"
to read -- MPN372: 1117 aaagtgaaaaatgacaccgc 1136 (SEQ ID NO: 44) --

Column 55, Item SEQ ID NO: 45:
Correct "Pri-9: 20 aaagtggaaaatgacaccge 1 (SEQ ID NO: 45)"
to read -- Pri-9: 20 aaagtggaaaatgacaccgc 1 (SEQ ID NO: 45) --

Signed and Sealed this
Fourteenth Day of October, 2014

Michelle K. Lee
*Deputy Director of the United States Patent and Trademark Office*

CERTIFICATE OF CORRECTION (continued)
U.S. Pat. No. 8,586,046 B2

Column 64, Item SEQ ID NO: 69, Location 191:
    Correct "NDQ*P$_W$LPTPG*"
    to read -- NDQ*PWLPTPG* --

Column 64, Item SEQ ID NO: 69, Location 231:
    Correct "*PD$_W$SPPSSNG*"
    to read -- *PDWSPPSSNG* --

Column 64, Item SEQ ID NO: 75, Location 191:
    Correct "NDQ*P$_W$LPTPG*"
    to read -- NDQ*PWLPTPG* --

Column 64, Item SEQ ID NO: 75, Location 231:
    Correct "*PD$_W$SPPSSNG*"
    to read -- *PDWSPPSSNG* --

Column 64, Item SEQ ID NO: 70:
    Correct "*P$_W$LPTPG*"
    to read -- *PWLPTPG* --

Column 64, Item SEQ ID NO: 70, Location 231:
    Correct "*PD$_W$SPPSSNG*"
    to read -- *PDWSPPSSNG* --

Column 65, Item SEQ ID NO: 70, Location 361:
    Correct "*NQK$_W$KMTPQD*"
    to read -- *NQKWKMTPQD* --

Column 65, Item SEQ ID NO: 70, Location 391:
    Correct "*F$_W$NTKSGGSQ*"
    to read -- *FWNTKSGGSQ* --

Column 65, Item SEQ ID NO: 71, Location 361:
    Correct "*NQK$_W$KMTPQD*"
    to read -- *NQKWKMTPQD* --

Column 65, Item SEQ ID NO: 71, Location 391:
    Correct "*F$_W$NTKSGGSQ*"
    to read -- *FWNTKSGGSQ* --